(12) United States Patent
Ebert et al.

(10) Patent No.: US 7,989,189 B2
(45) Date of Patent: Aug. 2, 2011

(54) MUTANT GTP CYCLOHYDROLASE II ENZYMES

(75) Inventors: Sybille Ebert, Biberach (DE); Hans-Peter Hohnmann, Loerrach (DE); Martin Lehmann, Grenzach-Wyhlen (DE); Nigel John Mouncey, Binningen (CH); Markus Wyss, Liestal (CH)

(73) Assignee: DSM IP Assets B.V., Te Heerlen (NL)

( * ) Notice: Subject to any disclaimer, the term of this patent is extended or adjusted under 35 U.S.C. 154(b) by 143 days.

(21) Appl. No.: 11/631,542

(22) PCT Filed: Jul. 7, 2005

(86) PCT No.: PCT/EP2005/007320
§ 371 (c)(1),
(2), (4) Date: Nov. 13, 2007

(87) PCT Pub. No.: WO2006/003015
PCT Pub. Date: Jan. 12, 2006

(65) Prior Publication Data
US 2008/0193998 A1    Aug. 14, 2008

(30) Foreign Application Priority Data

Jul. 7, 2004 (EP) .................................... 04015584

(51) Int. Cl.
C12P 17/00 (2006.01)
C12P 21/04 (2006.01)
C07H 21/04 (2006.01)
C12N 9/14 (2006.01)
C12N 15/00 (2006.01)
C12N 1/20 (2006.01)
C12Q 1/00 (2006.01)
C12Q 1/68 (2006.01)

(52) U.S. Cl. ............... 435/117; 435/4; 435/6; 435/69.1; 435/71.1; 435/252.3; 435/195; 435/440; 435/320.1; 536/23.2

(58) Field of Classification Search .......... None
See application file for complete search history.

(56) References Cited

U.S. PATENT DOCUMENTS 5,821,090 A    10/1998  Revuelta Doval et al.
6,322,995 B1   11/2001  Hohmann et al.

OTHER PUBLICATIONS

Branden et al. Introduction to Protein Structure, Garland Publishing Inc., New York, p. 247, 1991.*
Gusarov et al. UniProtKB—Accession T50543—2000.*
Protein Puprification Handbook—2001.*
Gusarov et al. Riboflavin biosynthetic genes in *Bacillus amyloliquefaciens*: primary structure, organization and regulation of activity. Mol Biol (Mosk). May-Jun. 1997;31(3):446-53.*
Richter et al., "Biosynthesis of Riboflavin: Cloning, Sequencing, Mapping, and Expression of the Gene Coding for GTP Cyclohydrolase II in *Escherichia coli*," J. Bact., vol. 175, No. 13, pp. 4045-4051, XP002095462 ISSN: 0021-9193 (1993).
Herz et al., "Biosynthesis of riboflavin in plants. The ribA gene of *Arabidopsis thaliana* specifies a bifunctional GTP cyclohydrolase II/3,4-di-hydroxy-2-butanone 4-phosphate synthase," Phytochem., vol. 53, No. 7, pp. 723-731, XP004291367 ISSN: 0031-9422 (2000).
Huembelin et al., "GTP cyclohydrolase II and 3,4-diydroxy-2-butanone 4-phosphate synthase are rate-limiting enzymes in riboflavin synthesis of an industrial *Bacillus subtilis* strain used for riboflavin production," J. Ind. Microbiol. & Tech., vol. 22, No. 1, pp. 1-7, XP002348036 ISSN 1367-5435 (1999).
Kaiser et al., "Biosynthesis of vitamin B2. An essential zinc ion at the catalytic site of GTP cyclohydrolase II," Eur. J. Biochem., vol. 269, No. 21, pp. 5264-5270, XP002348037 ISSN: 0014-2956 (2002).
Bacher et al., "Biosynthesis of Riboflavin: GTP Cyclohydrolase II, Deaminase, And Reductase," Methods in Enzymology, vol. 280, pp. 382-389, XP009030498 ISSN: 0076-6879 (1997).
Ritz et al., "Biosynthesis of riboflavin: Studies on the mechanism of GTP cyclohydrolase II," J. Biol. Chem., vol. 276, No. 25, pp. 22273-22277, XP002233121 ISSN: 0021-9258 (2001).

* cited by examiner

*Primary Examiner* — Yong D Pak
(74) *Attorney, Agent, or Firm* — Hoxie & Associates LLC

(57) ABSTRACT

The present invention relates to modified GTP cyclohydrolase II enzymes that display increased specific activity, and to polynucleotides encoding them. The invention further pertains to vectors comprising these polynucleotides and host cells containing such vectors. The invention provides a method for producing the modified enzyme and a method for producing riboflavin, a riboflavin precursor, FMN, FAD, or a derivative thereof.

4 Claims, No Drawings

SEQUENCE LISTING

<160> NUMBER OF SEQ ID NOS: 43

<210> SEQ ID NO 1
<211> LENGTH: 1197
<212> TYPE: DNA
<213> ORGANISM: Bacillus subtilis

<400> SEQUENCE: 1

```
atgtttcatc cgatagaaga agcactggac gctttaaaaa aaggcgaagt catcatcgtt      60
gtagatgatg aagacagaga aaatgaagga gactttgtgg ctcttgccga gcatgcaacg     120
ccggaagtca ttaactttat ggcgacacat gggagaggac tgatctgcac gccgctcagt     180
gaggaaatcg cagacaggct tgatcttcac cctatggttg agcataatac agactctcac     240
cacactgcat ttaccgtaag catagaccat cgtgaaacga agacaggtat cagcgctcaa     300
gaaagatctt ttaccgttca agcattgctg gacagcaaat ccgtgccatc tgattttcag     360
cgtccggggc acatttttcc actgattgcg aaaaaggag gtgtcctgaa aagagcgggc     420
catacagaag ctgctgttga tcttgctgaa gcttgtggat ctccaggagc cggcgtcatt     480
tgtgaaatta tgaatgaaga cggaacgatg gcgagagtgc ctgagctcat gaaattgcg      540 aaaaagcatc aattaaaaat gatcaccatt aaggatttga ttcaataccg ttacaatctg     600
acaacacttg tcgagcgtga agttgacatt acgctgccta ctgattttgg gacatttaag     660
gtttatggat acacaaatga ggtagatgga aaagagcatg tcgcatttgt gatgggagat     720
gtgccgttcg gagaagaacc ggtattggtc cgggtgcatt cagaatgtct cacaggtgac     780
gtgtttggct ctcatcgctg tgattgcgga ccgcagctgc acgccgcgct gaaccaaatt     840
```

```
gccgcagaag gccgtggagt gctcctgtac ttgcgccaag aaggacgagg catcggttta    900
atcaataaat taaaagctta taagcttcag gaacaaggct atgacaccgt agaagccaat    960
gaggcgcttg gattcttgcc ggatcttcgc aactatggca tcggagcaca aattttacgc   1020
gacctcggtg tccggaatat gaagcttttg acgaataatc cgcgaaaaat cgcaggcctt   1080
gaaggctacg gactcagtat ttcagaaaga gtgccgcttc aaatggaggc gaaagaacac   1140
aataaaaaat atttgcaaac caaaatgaac aagctaggtc atttacttca tttctaa      1197
```

<210> SEQ ID NO 2
<211> LENGTH: 398
<212> TYPE: PRT
<213> ORGANISM: Bacillus subtilis

<400> SEQUENCE: 2

```
Met Phe His Pro Ile Glu Glu Ala Leu Asp Ala Leu Lys Lys Gly Glu
1               5                   10                  15

Val Ile Ile Val Val Asp Asp Glu Asp Arg Glu Asn Glu Gly Asp Phe
            20                  25                  30

Val Ala Leu Ala Glu His Ala Thr Pro Glu Val Ile Asn Phe Met Ala
        35                  40                  45

Thr His Gly Arg Gly Leu Ile Cys Thr Pro Leu Ser Glu Glu Ile Ala
    50                  55                  60

Asp Arg Leu Asp Leu His Pro Met Val Glu His Asn Thr Asp Ser His
65                  70                  75                  80

His Thr Ala Phe Thr Val Ser Ile Asp His Arg Glu Thr Lys Thr Gly
                85                  90                  95

Ile Ser Ala Gln Glu Arg Ser Phe Thr Val Gln Ala Leu Leu Asp Ser
            100                 105                 110

Lys Ser Val Pro Ser Asp Phe Gln Arg Pro Gly His Ile Phe Pro Leu
        115                 120                 125

Ile Ala Lys Lys Gly Gly Val Leu Lys Arg Ala Gly His Thr Glu Ala
    130                 135                 140

Ala Val Asp Leu Ala Glu Ala Cys Gly Ser Pro Gly Ala Gly Val Ile
145                 150                 155                 160

Cys Glu Ile Met Asn Glu Asp Gly Thr Met Ala Arg Val Pro Glu Leu
                165                 170                 175

Ile Glu Ile Ala Lys Lys His Gln Leu Lys Met Ile Thr Ile Lys Asp
            180                 185                 190

Leu Ile Gln Tyr Arg Tyr Asn Leu Thr Thr Leu Val Glu Arg Glu Val
        195                 200                 205

Asp Ile Thr Leu Pro Thr Asp Phe Gly Thr Phe Lys Val Tyr Gly Tyr
    210                 215                 220

Thr Asn Glu Val Asp Gly Lys Glu His Val Ala Phe Val Met Gly Asp
225                 230                 235                 240

Val Pro Phe Gly Glu Glu Pro Val Leu Val Arg Val His Ser Glu Cys
                245                 250                 255

Leu Thr Gly Asp Val Phe Gly Ser His Arg Cys Asp Cys Gly Pro Gln
            260                 265                 270

Leu His Ala Ala Leu Asn Gln Ile Ala Ala Glu Gly Arg Gly Val Leu
        275                 280                 285

Leu Tyr Leu Arg Gln Glu Gly Arg Gly Ile Gly Leu Ile Asn Lys Leu
    290                 295                 300

Lys Ala Tyr Lys Leu Gln Glu Gln Gly Tyr Asp Thr Val Glu Ala Asn
305                 310                 315                 320
```

```
Glu Ala Leu Gly Phe Leu Pro Asp Leu Arg Asn Tyr Gly Ile Gly Ala
            325                 330                 335

Gln Ile Leu Arg Asp Leu Gly Val Arg Asn Met Lys Leu Leu Thr Asn
            340                 345                 350

Asn Pro Arg Lys Ile Ala Gly Leu Glu Gly Tyr Gly Leu Ser Ile Ser
            355                 360                 365

Glu Arg Val Pro Leu Gln Met Glu Ala Lys Glu His Asn Lys Lys Tyr
        370                 375                 380

Leu Gln Thr Lys Met Asn Lys Leu Gly His Leu Leu His Phe
385                 390                 395

<210> SEQ ID NO 3
<211> LENGTH: 1239
<212> TYPE: DNA
<213> ORGANISM: Bacillus subtilis

<400> SEQUENCE: 3
atgagaggat ctcaccatca ccatcaccat gggatcgatc atatgtttca tccgatagaa      60
gaagcactgg acgctttaaa aaaggcgaa gtcatcatcg ttgtagatga tgaagacaga     120
gaaaatgaag gagactttgt ggctcttgcc gagcatgcaa cgccggaagt cattaacttt     180
atggcgacac atgggagagg actgatctgc acgccgctca gtgaggaaat cgcagacagg     240
cttgatcttc accctatggt tgagcataat acagactctc accacactgc atttaccgta     300
agcatagacc atcgtgaaac gaagacaggt atcagcgctc aagaaagatc ttttaccgtt     360
caagcattgc tggacagcaa atccgtgcca tctgattttc agcgtccggg gcacattttt     420
ccactgattg cgaaaaaagg aggtgtcctg aaaagagcgg ccatacaga gctgctgtt      480 gatcttgctg aagcttgtgg atctccagga gccggcgtca tttgtgaaat tatgaatgaa     540
gacggaacga tggcgagagt gcctgagctc attgaaattg cgaaaaagca tcaattaaaa     600
atgatcacca ttaaggattt gattcaatac cgttacaatc tgacaacact tgtcgagcgt     660
gaagttgaca ttacgctgcc tactgatttt gggacattta aggtttatgg atacacaaat     720
gaggtagatg gaaaagagca tgtcgcattt gtgatggag atgtgccgtt cggagaagaa     780
ccggtattgg tccgggtgca ttcagaatgt ctcacaggtg acgtgtttgg ctctcatcgc     840
tgtgattgcg accgcagct gcacgccgcg ctgaaccaaa ttgccgcaga aggccgtgga     900
gtgctcctgt acttgcgcca agaaggacga ggcatcggtt taatcaataa attaaaagct     960
tataagcttc aggaacaagg ctatgacacc gtagaagcca atgaggcgct tggattcttg    1020
ccggatcttc gcaactatgg catcggagca caaatttac gcgacctcgg tgtccggaat    1080
atgaagcttt tgacgaataa tccgcgaaaa atcgcaggcc ttgaaggcta cggactcagt    1140
atttcagaaa gagtgccgct tcaaatggag gcgaagaac acaataaaaa atatttgcaa    1200
accaaaatga caagctagg tcatttactt catttctaa                            1239

<210> SEQ ID NO 4
<211> LENGTH: 412
<212> TYPE: PRT
<213> ORGANISM: Bacillus subtilis

<400> SEQUENCE: 4

Met Arg Gly Ser His His His His His His Gly Ile Asp His Met Phe
1               5                   10                  15

His Pro Ile Glu Glu Ala Leu Asp Ala Leu Lys Lys Gly Glu Val Ile
            20                  25                  30
```

Ile Val Val Asp Asp Glu Asp Arg Glu Asn Glu Gly Asp Phe Val Ala
            35                  40                  45

Leu Ala Glu His Ala Thr Pro Glu Val Ile Asn Phe Met Ala Thr His
 50                  55                  60

Gly Arg Gly Leu Ile Cys Thr Pro Leu Ser Glu Ile Ala Asp Arg
 65                  70                  75                  80

Leu Asp Leu His Pro Met Val Glu His Asn Thr Asp Ser His Thr
                     85                  90                  95

Ala Phe Thr Val Ser Ile Asp His Arg Glu Thr Lys Thr Gly Ile Ser
                    100                 105                 110

Ala Gln Glu Arg Ser Phe Thr Val Gln Ala Leu Leu Asp Ser Lys Ser
                115                 120                 125

Val Pro Ser Asp Phe Gln Arg Pro Gly His Ile Phe Pro Leu Ile Ala
            130                 135                 140

Lys Lys Gly Gly Val Leu Lys Arg Ala Gly His Thr Glu Ala Ala Val
145                 150                 155                 160

Asp Leu Ala Glu Ala Cys Gly Ser Pro Gly Ala Gly Val Ile Cys Glu
                    165                 170                 175

Ile Met Asn Glu Asp Gly Thr Met Ala Arg Val Pro Glu Leu Ile Glu
                180                 185                 190

Ile Ala Lys Lys His Gln Leu Lys Met Ile Thr Ile Lys Asp Leu Ile
            195                 200                 205

Gln Tyr Arg Tyr Asn Leu Thr Thr Leu Val Glu Arg Glu Val Asp Ile
        210                 215                 220

Thr Leu Pro Thr Asp Phe Gly Thr Phe Lys Val Tyr Gly Tyr Thr Asn
225                 230                 235                 240

Glu Val Asp Gly Lys Glu His Val Ala Phe Val Met Gly Asp Val Pro
                    245                 250                 255

Phe Gly Glu Glu Pro Val Leu Val Arg Val His Ser Gly Cys Leu Thr
                260                 265                 270

Gly Asp Val Phe Gly Ser His Arg Cys Asp Cys Gly Pro Gln Leu His
            275                 280                 285

Ala Ala Leu Asn Gln Ile Ala Ala Glu Gly Arg Gly Val Leu Leu Tyr
290                 295                 300

Leu Arg Gln Glu Gly Arg Gly Ile Gly Leu Ile Asn Lys Leu Lys Ala
305                 310                 315                 320

Tyr Lys Leu Gln Glu Gln Gly Tyr Asp Thr Val Glu Ala Asn Glu Ala
                325                 330                 335

Leu Gly Phe Leu Pro Asp Leu Arg Asn Tyr Gly Ile Gly Ala Gln Ile
            340                 345                 350

Leu Arg Asp Leu Gly Val Arg Asn Met Lys Leu Leu Thr Asn Asn Pro
        355                 360                 365

Arg Lys Ile Ala Gly Leu Glu Gly Tyr Gly Leu Ser Ile Ser Glu Arg
    370                 375                 380

Val Pro Leu Gln Met Glu Ala Lys Glu His Asn Lys Lys Tyr Leu Gln
385                 390                 395                 400

Thr Lys Met Asn Lys Leu Gly His Leu Leu His Phe
                405                 410

<210> SEQ ID NO 5
<211> LENGTH: 1239
<212> TYPE: DNA
<213> ORGANISM: Bacillus subtilis

```
<400> SEQUENCE: 5
atgagaggat ctcaccatca ccatcaccat gggatcgatc atatgtttca tccgatagaa     60
gaagcactgg acgctttaaa aaaaggcgaa gtcatcatcg ttgtagatga tgaagacaga    120
gaaaatgaag gagactttgt ggctcttgcc gagcatgcaa cgccggaagt cattaacttt    180
atggcgacac atgggagagg actgatctgc acgccgctca gtgaggaaat cgcagacagg    240
cttgatcttc accctatggt tgagcataat acagactctc accacactgc atttaccgta    300
agcatagacc atcgtgaaac gaagacaggt atcagcgctc aagaaagatc ttttaccgtt    360
caagcattgc tggacagcaa atccgtgcca tctgattttc agcgtccggg gcacattttt    420
ccactgattg cgaaaaaagg aggtgtcctg aaaagagcgg ccatacaga gctgctgtt     480
gatcttgctg aagcttgtgg atctccagga gccggcgtca tttgtgaaat tatgaatgaa    540
gacggaacga tggcgagagt gcctgagctc attgaaattg cgaaaaagca tcaattaaaa    600
atgatcacca ttaaggattt gattcaatgc cgttacaatc tgacaacact tgtcgagcgt    660
gaagttgaca ttacgctgcc tactgatttt gggacattta aggtttatgg atacacaaat    720
gaggtagatg gaaaagagca tgtcgcattt gtgatgggag atgtgccgtt cggagaagaa    780
ccggtattgg tccgggtgca ttcagaatgt ctcacaggtg acgtgtttgg ctctcatcgc    840
tgtgattgcg gaccgcagct gcacgccacg ctgaaccaaa ttgccgcaga aggccgtgga    900
gtgctcctgt acttgcgcca agaaggacga ggcatcggtt aatcaataa attaaaagct    960
tataagcttc aggaacaagg ctatgacacc gtagaagcca atgaggcgct tggattcttg   1020
ccggatcttc gcaactatgg catcggagca caaattttac gcgacctcgg tgtccggaat   1080
atgaagcttt tgacgaataa tccgcgaaaa atcgcaggcc ttgaaggcta cggactcagt   1140
atttcagaaa gagtgccgct tcaaatggag gcgaaagaac acaataaaaa atatttgcaa   1200
accaaaatga acaagctagg tcatttactt catttctaa                          1239

<210> SEQ ID NO 6
<211> LENGTH: 412
<212> TYPE: PRT
<213> ORGANISM: Bacillus subtilis

<400> SEQUENCE: 6

Met Arg Gly Ser His His His His His His Gly Ile Asp His Met Phe
1               5                   10                  15

His Pro Ile Glu Glu Ala Leu Asp Ala Leu Lys Lys Gly Glu Val Ile
            20                  25                  30

Ile Val Val Asp Asp Glu Asp Arg Glu Asn Glu Gly Asp Phe Val Ala
        35                  40                  45

Leu Ala Glu His Ala Thr Pro Glu Val Ile Asn Phe Met Ala Thr His
    50                  55                  60

Gly Arg Gly Leu Ile Cys Thr Pro Leu Ser Glu Glu Ile Ala Asp Arg
65                  70                  75                  80

Leu Asp Leu His Pro Met Val Glu His Asn Thr Asp Ser His His Thr
                85                  90                  95

Ala Phe Thr Val Ser Ile Asp His Arg Glu Thr Lys Thr Gly Ile Ser
            100                 105                 110

Ala Gln Glu Arg Ser Phe Thr Val Gln Ala Leu Leu Asp Ser Lys Ser
        115                 120                 125

Val Pro Ser Asp Phe Gln Arg Pro Gly His Ile Phe Pro Leu Ile Ala
    130                 135                 140
```

Lys Lys Gly Gly Val Leu Lys Arg Ala Gly His Thr Glu Ala Ala Val
145                 150                 155                 160

Asp Leu Ala Glu Ala Cys Gly Ser Pro Gly Ala Gly Val Ile Cys Glu
                165                 170                 175

Ile Met Asn Glu Asp Gly Thr Met Ala Arg Val Pro Glu Leu Ile Glu
            180                 185                 190

Ile Ala Lys Lys His Gln Leu Lys Met Ile Thr Ile Lys Asp Leu Ile
        195                 200                 205

Gln Cys Arg Tyr Asn Leu Thr Thr Leu Val Glu Arg Glu Val Asp Ile
    210                 215                 220

Thr Leu Pro Thr Asp Phe Gly Thr Phe Lys Val Tyr Gly Tyr Thr Asn
225                 230                 235                 240

Glu Val Asp Gly Lys Glu His Val Ala Phe Val Met Gly Asp Val Pro
                245                 250                 255

Phe Gly Glu Glu Pro Val Leu Val Arg Val His Ser Glu Cys Leu Thr
            260                 265                 270

Gly Asp Val Phe Gly Ser His Arg Cys Asp Cys Gly Pro Gln Leu His
        275                 280                 285

Ala Thr Leu Asn Gln Ile Ala Ala Glu Gly Arg Gly Val Leu Leu Tyr
    290                 295                 300

Leu Arg Gln Glu Gly Arg Gly Ile Gly Leu Ile Asn Lys Leu Lys Ala
305                 310                 315                 320

Tyr Lys Leu Gln Glu Gln Gly Tyr Asp Thr Val Glu Ala Asn Glu Ala
                325                 330                 335

Leu Gly Phe Leu Pro Asp Leu Arg Asn Tyr Gly Ile Gly Ala Gln Ile
            340                 345                 350

Leu Arg Asp Leu Gly Val Arg Asn Met Lys Leu Leu Thr Asn Asn Pro
        355                 360                 365

Arg Lys Ile Ala Gly Leu Glu Gly Tyr Gly Leu Ser Ile Ser Glu Arg
    370                 375                 380

Val Pro Leu Gln Met Glu Ala Lys Glu His Asn Lys Lys Tyr Leu Gln
385                 390                 395                 400

Thr Lys Met Asn Lys Leu Gly His Leu Leu His Phe
                405                 410

<210> SEQ ID NO 7
<211> LENGTH: 1239
<212> TYPE: DNA
<213> ORGANISM: Bacillus subtilis

<400> SEQUENCE: 7
atgagaggat ctcaccatca ccatcaccat gggatcgatc atatgtttca tccgatagaa      60
gaagcactgg acgctttaaa aaaaggcgaa gtcatcatcg ttgtagatga tgaagacaga     120
gaaaatgaag gagactttgt ggctcttgcc gagcatgcaa cgccggaagt cattaacttt     180
atggcgacac atgggagagg actgatctgc acgccgctca gtgaggaaat cgcagacagg     240
cttgatcttc accctatggt tgagcataat acagactctc accacactgc atttaccgta     300
agcatagacc atcgtgaaac gaagacaggt atcagcgctc aagaaagatc tttaccgtt     360 caagcattgc tggacagcaa atccgtgcca tctgattttc agcgtccggg gcacattttt     420
ccactgattg cgaaaaaagg aggtgtcctg aaaagagcgg ccatacaga agctgctgtt      480 gatcttgctg aagcttgtgg atctccagga gccggcgtca tttgtgaaat tatgaatgaa     540
gacggaacga tggcgagagt gcctgagctc attgaaattg cgaaaaagca tcaattaaaa     600
atgatcacca ttaaggattt gattcaatgc cgttacaatc tgacaacact tgtcgagcgt     660

-continued

```
gaagttgaca ttacgctgcc tactgatttt gggacattta aggtttatgg atacacaaat    720
gaggtagatg gaaaagagca tgtcgcattt gtgatgggag atgtgccgtt cggagaagaa    780
ccggtattgg tccgggtgca ttcagaatgt ctcacaggtg acgcgtttgg ctctcatcgc    840
tgtgattgcg gaccgcagct gcacgccgcg ctgaaccaaa ttgccgcaga aggccgtgga    900
gtgctcctgt acttgcgcca agaaggacga ggcatcggtt taatcaataa attaaaagct    960
tataagcttc aggaacaagg ctatgacacc gtagaagcca atgaggcgct tggattcttg   1020
ccggatcttc gcaactatgg catcggagca caaattttac gcgacctcgg tgtccggaat   1080
atgaagcttt tgacgaataa tccgcgaaaa atcgcaggcc ttgaaggcta cggactcagt   1140
atttcagaaa gagtgccgct tcaaatggag gcgaaagaac acaataaaaa atatttgcaa   1200
accaaaatga acaagctagg tcatttactt catttctaa                          1239
```

<210> SEQ ID NO 8
<211> LENGTH: 412
<212> TYPE: PRT
<213> ORGANISM: Bacillus subtilis

<400> SEQUENCE: 8

```
Met Arg Gly Ser His His His His His His Gly Ile Asp His Met Phe
1               5                   10                  15

His Pro Ile Glu Glu Ala Leu Asp Ala Leu Lys Lys Gly Glu Val Ile
            20                  25                  30

Ile Val Val Asp Asp Glu Asp Arg Glu Asn Glu Gly Asp Phe Val Ala
        35                  40                  45

Leu Ala Glu His Ala Thr Pro Glu Val Ile Asn Phe Met Ala Thr His
    50                  55                  60

Gly Arg Gly Leu Ile Cys Thr Pro Leu Ser Glu Glu Ile Ala Asp Arg
65                  70                  75                  80

Leu Asp Leu His Pro Met Val Glu His Asn Thr Asp Ser His His Thr
                85                  90                  95

Ala Phe Thr Val Ser Ile Asp His Arg Glu Thr Lys Thr Gly Ile Ser
            100                 105                 110

Ala Gln Glu Arg Ser Phe Thr Val Gln Ala Leu Leu Asp Ser Lys Ser
        115                 120                 125

Val Pro Ser Asp Phe Gln Arg Pro Gly His Ile Phe Pro Leu Ile Ala
    130                 135                 140

Lys Lys Gly Gly Val Leu Lys Arg Ala Gly His Thr Glu Ala Ala Val
145                 150                 155                 160

Asp Leu Ala Glu Ala Cys Gly Ser Pro Gly Ala Gly Val Ile Cys Glu
                165                 170                 175

Ile Met Asn Glu Asp Gly Thr Met Ala Arg Val Pro Glu Leu Ile Glu
            180                 185                 190

Ile Ala Lys Lys His Gln Leu Lys Met Ile Thr Ile Lys Asp Leu Ile
        195                 200                 205

Gln Cys Arg Tyr Asn Leu Thr Thr Leu Val Glu Arg Glu Val Asp Ile
    210                 215                 220

Thr Leu Pro Thr Asp Phe Gly Thr Phe Lys Val Tyr Gly Tyr Thr Asn
225                 230                 235                 240

Glu Val Asp Gly Lys Glu His Val Ala Phe Val Met Gly Asp Val Pro
                245                 250                 255

Phe Gly Glu Glu Pro Val Leu Val Arg Val His Ser Glu Cys Leu Thr
            260                 265                 270
```

```
Gly Asp Ala Phe Gly Ser His Arg Cys Asp Cys Gly Pro Gln Leu His
                275                 280                 285

Ala Ala Leu Asn Gln Ile Ala Ala Glu Gly Arg Gly Val Leu Leu Tyr
290                 295                 300

Leu Arg Gln Glu Gly Arg Gly Ile Gly Leu Ile Asn Lys Leu Lys Ala
305                 310                 315                 320

Tyr Lys Leu Gln Glu Gln Gly Tyr Asp Thr Val Glu Ala Asn Glu Ala
                325                 330                 335

Leu Gly Phe Leu Pro Asp Leu Arg Asn Tyr Gly Ile Gly Ala Gln Ile
                340                 345                 350

Leu Arg Asp Leu Gly Val Arg Asn Met Lys Leu Leu Thr Asn Asn Pro
                355                 360                 365

Arg Lys Ile Ala Gly Leu Glu Gly Tyr Gly Leu Ser Ile Ser Glu Arg
370                 375                 380

Val Pro Leu Gln Met Glu Ala Lys Glu His Asn Lys Lys Tyr Leu Gln
385                 390                 395                 400

Thr Lys Met Asn Lys Leu Gly His Leu Leu His Phe
                405                 410

<210> SEQ ID NO 9
<211> LENGTH: 1239
<212> TYPE: DNA
<213> ORGANISM: Bacillus subtilis

<400> SEQUENCE: 9
atgagaggat ctcaccatca ccatcaccat gggatcgatc atatgtttca tccgatagaa      60
gaagcactgg acgctttaaa aaaaggcgaa gtcatcatcg ttgtagatga tgaagacaga     120
gaaaatgaag gagactttgt ggctcttgcc gagcatgcaa cgccggaagt cattaacttt     180
atggcgacac atgggagagg actgatctgc acgccgctca gtgaggaaat cgcagacagg     240
cttgatcttc accctatggt tgagcataat acagactctc accacactgc atttaccgta     300
agcatagacc atcgtgaaac gaagacaggt atcagcgctc aagaaagatc ttttaccgtt     360
caagcattgc tggacagcaa atccgtgcca tctgattttc agcgtccggg gcacattttt     420
ccactgattg cgaaaaaagg aggtgtcctg aaaagagcgg ccatacaga agctgctgtt      480 gatcttgctg aagcttgtgg atctccagga gccggcgtca tttgtgaaat tatgaatgaa     540
gacggaacga tggcgagagt gcctgagctc attgaaattg cgaaaaagca tcaattaaaa     600
atgatcacca ttaaggattt gattcaatac cgttacaatc tgacaacact tgtcgagcgt     660
gaagttgaca ttacgctgcc tactgatttt gggacattta aggtttatgg atacacaaat     720
gaggtagatg gaaaagagca tgtcgcattt gtgatgggag atgtgccgtt cggagaagaa     780
ccggtattgg tccgggtgca ttcagaatgt ctcacaggtg acgtgtttgg ctctcatcgc     840
tgtgattgcg gaccgcagct gcacgccgcg ctgaaccaaa ttgccgcaga aggccgtgga     900
gtgctcctgt acttgcgcca agaaggacga ggcatcggtt aatcaataa attaaaagct      960 tataagcttc aggaacaagg ctatgacacc gtagaagcca atgaggcgct tggattcttg    1020
ccggatcttc gcaactatgg catcggagca caaattttac gcgacctcgg tgtccggaat    1080
ataaagcttt tgacgaataa tccgcgaaaa atcgcaggcc ttgaaggcta cggactcagt    1140
atttcagaaa gagtgccgct tcaaatggag gcgaagaac acaataaaaa atatttgcaa    1200
accaaaatga acaagctagg tcatttactt catttctaa                            1239
```

```
<210> SEQ ID NO 10
<211> LENGTH: 412
<212> TYPE: PRT
<213> ORGANISM: Bacillus subtilis

<400> SEQUENCE: 10

Met Arg Gly Ser His His His His His His Gly Ile Asp His Met Phe
1               5                   10                  15

His Pro Ile Glu Glu Ala Leu Asp Ala Leu Lys Lys Gly Glu Val Ile
            20                  25                  30

Ile Val Val Asp Asp Glu Asp Arg Glu Asn Glu Gly Asp Phe Val Ala
        35                  40                  45

Leu Ala Glu His Ala Thr Pro Glu Val Ile Asn Phe Met Ala Thr His
    50                  55                  60

Gly Arg Gly Leu Ile Cys Thr Pro Leu Ser Glu Glu Ile Ala Asp Arg
65                  70                  75                  80

Leu Asp Leu His Pro Met Val Glu His Asn Thr Asp Ser His His Thr
                85                  90                  95

Ala Phe Thr Val Ser Ile Asp His Arg Glu Thr Lys Thr Gly Ile Ser
            100                 105                 110

Ala Gln Glu Arg Ser Phe Thr Val Gln Ala Leu Leu Asp Ser Lys Ser
        115                 120                 125

Val Pro Ser Asp Phe Gln Arg Pro Gly His Ile Phe Pro Leu Ile Ala
    130                 135                 140

Lys Lys Gly Gly Val Leu Lys Arg Ala Gly His Thr Glu Ala Ala Val
145                 150                 155                 160

Asp Leu Ala Glu Ala Cys Gly Ser Pro Gly Ala Gly Val Ile Cys Glu
                165                 170                 175

Ile Met Asn Glu Asp Gly Thr Met Ala Arg Val Pro Glu Leu Ile Glu
            180                 185                 190

Ile Ala Lys Lys His Gln Leu Lys Met Ile Thr Ile Lys Asp Leu Ile
        195                 200                 205

Gln Tyr Arg Tyr Asn Leu Thr Thr Leu Val Glu Arg Glu Val Asp Ile
    210                 215                 220

Thr Leu Pro Thr Asp Phe Gly Thr Phe Lys Val Tyr Gly Tyr Thr Asn
225                 230                 235                 240

Glu Val Asp Gly Lys Glu His Val Ala Phe Val Met Gly Asp Val Pro
                245                 250                 255

Phe Gly Glu Glu Pro Val Leu Val Arg Val His Ser Glu Cys Leu Thr
            260                 265                 270

Gly Asp Val Phe Gly Ser His Arg Cys Asp Cys Gly Pro Gln Leu His
        275                 280                 285

Ala Ala Leu Asn Gln Ile Ala Ala Glu Gly Arg Gly Val Leu Leu Tyr
    290                 295                 300

Leu Arg Gln Glu Gly Arg Gly Ile Gly Leu Ile Asn Lys Leu Lys Ala
305                 310                 315                 320

Tyr Lys Leu Gln Glu Gln Gly Tyr Asp Thr Val Glu Ala Asn Glu Ala
                325                 330                 335

Leu Gly Phe Leu Pro Asp Leu Arg Asn Tyr Gly Ile Gly Ala Gln Ile
            340                 345                 350

Leu Arg Asp Leu Gly Val Arg Asn Ile Lys Leu Leu Thr Asn Asn Pro
        355                 360                 365

Arg Lys Ile Ala Gly Leu Glu Gly Tyr Gly Leu Ser Ile Ser Glu Arg
    370                 375                 380
```

Val Pro Leu Gln Met Glu Ala Lys Glu His Asn Lys Lys Tyr Leu Gln
385                 390                 395                 400

Thr Lys Met Asn Lys Leu Gly His Leu Leu His Phe
            405                 410

<210> SEQ ID NO 11
<211> LENGTH: 1239
<212> TYPE: DNA
<213> ORGANISM: Bacillus subtilis

<400> SEQUENCE: 11
atgagaggat ctcaccatca ccatcaccat gggatcgatc atatgtttca tccgatagaa      60
gaagcactgg acgctttaaa aaaaggcgaa gtcatcatcg ttgtagatga tgaagacaga     120
gaaaatgaag gagactttgt ggctcttgcc gagcatgcaa cgccggaagt cattaacttt     180
atggcgacac atgggagagg actgatctgc acgccgctca gtgaggaaat cgcagacagg     240
cttgatcttc accctatggt tgagcataat acagactctc accacactgc atttaccgta     300
agcatagacc atcgtgaaac gaagacaggt atcagcgctc aagaaagatc ttttaccgtt     360
caagcattgc tggacagcaa atccgtgcca tctgattttc agcgtccggg gcacattttt     420
ccactgattg cgaaaaaagg aggtgtcctg aaaagagcgg ccatacagaa gctgctgtt      480
gatcttgctg aagcttgtgg atctccagga gccggcgtca tttgtgaaat tatgaatgaa     540
gacggaacga tggcgagagt gcctgagctc attgaaattg cgaaaaagca tcaattaaaa     600
atgatcacca ttaaggattt gattcaatgc cgttacaatc tgacaacact tgtcgagcgt     660
gaagttgaca ttacgctgcc tactgatttt gggacattta aggtttatgg atacacaaat     720
gaggtagatg aaaagagcca tgtcgcattt gtgatgggag atgtgccgtt cggagaagaa     780
ccggtattgg tccgggtgca ttcagaatgt ctcacaggtg acgtgtttgg ctctcatcgc     840
tgtgattgcg gaccgcagct gcacgccacg ctgaaccaaa ttgccacaga aggccgtgga     900
gtgctcctgt acttgcgcca agaaggacga ggcatcggtt taatcaataa attaaaagct     960
tataagcttc aggaacaagg ctatgacacc gtagaagcca atgaggcgct tggattcttg    1020
ccggatcttc gcaactatgg catcggagca caaattttac gcgacctcgg tgtccggaat    1080
atgaagcttt tgacgaataa tccgcgaaaa atcgcaggcc ttgaaggcta cggactcagt    1140
atttcagaaa gagtgccgct tcaaatggag gcgaaagaac acaataaaaa atatttgcaa    1200
accaaaatga caagctagg tcatttactt catttctaa                            1239

<210> SEQ ID NO 12
<211> LENGTH: 412
<212> TYPE: PRT
<213> ORGANISM: Bacillus subtilis

<400> SEQUENCE: 12

Met Arg Gly Ser His His His His His His Gly Ile Asp His Met Phe
1               5                   10                  15

His Pro Ile Glu Glu Ala Leu Asp Ala Leu Lys Lys Gly Glu Val Ile
            20                  25                  30

Ile Val Val Asp Asp Glu Asp Arg Glu Asn Glu Gly Asp Phe Val Ala
        35                  40                  45

Leu Ala Glu His Ala Thr Pro Glu Val Ile Asn Phe Met Ala Thr His
    50                  55                  60

Gly Arg Gly Leu Ile Cys Thr Pro Leu Ser Glu Glu Ile Ala Asp Arg
65                  70                  75                  80

```
Leu Asp Leu His Pro Met Val Glu His Asn Thr Asp Ser His His Thr
                85                  90                  95

Ala Phe Thr Val Ser Ile Asp His Arg Glu Thr Lys Thr Gly Ile Ser
            100                 105                 110

Ala Gln Glu Arg Ser Phe Thr Val Gln Ala Leu Leu Asp Ser Lys Ser
        115                 120                 125

Val Pro Ser Asp Phe Gln Arg Pro Gly His Ile Phe Pro Leu Ile Ala
    130                 135                 140

Lys Gly Gly Val Leu Lys Arg Ala Gly His Thr Glu Ala Ala Val
145                 150                 155                 160

Asp Leu Ala Glu Ala Cys Gly Ser Pro Ala Gly Val Ile Cys Glu
                165                 170                 175

Ile Met Asn Glu Asp Gly Thr Met Ala Arg Val Pro Glu Leu Ile Glu
            180                 185                 190

Ile Ala Lys Lys His Gln Leu Lys Met Ile Thr Ile Lys Asp Leu Ile
        195                 200                 205

Gln Cys Arg Tyr Asn Leu Thr Thr Leu Val Glu Arg Glu Val Asp Ile
    210                 215                 220

Thr Leu Pro Thr Asp Phe Gly Thr Phe Lys Val Tyr Gly Tyr Thr Asn
225                 230                 235                 240

Glu Val Asp Gly Lys Glu His Val Ala Phe Val Met Gly Asp Val Pro
                245                 250                 255

Phe Gly Glu Glu Pro Val Leu Val Arg Val His Ser Glu Cys Leu Thr
            260                 265                 270

Gly Asp Val Phe Gly Ser His Arg Cys Asp Cys Gly Pro Gln Leu His
        275                 280                 285

Ala Thr Leu Asn Gln Ile Ala Thr Glu Gly Arg Gly Val Leu Leu Tyr
    290                 295                 300

Leu Arg Gln Glu Gly Arg Gly Ile Gly Leu Ile Asn Lys Leu Lys Ala
305                 310                 315                 320

Tyr Lys Leu Gln Glu Gln Gly Tyr Asp Thr Val Glu Ala Asn Glu Ala
                325                 330                 335

Leu Gly Phe Leu Pro Asp Leu Arg Asn Tyr Gly Ile Gly Ala Gln Ile
            340                 345                 350

Leu Arg Asp Leu Gly Val Arg Asn Met Lys Leu Leu Thr Asn Asn Pro
        355                 360                 365

Arg Lys Ile Ala Gly Leu Glu Gly Tyr Gly Leu Ser Ile Ser Glu Arg
    370                 375                 380

Val Pro Leu Gln Met Glu Ala Lys Glu His Asn Lys Lys Tyr Leu Gln
385                 390                 395                 400

Thr Lys Met Asn Lys Leu Gly His Leu Leu His Phe
                405                 410

<210> SEQ ID NO 13
<211> LENGTH: 1239
<212> TYPE: DNA
<213> ORGANISM: Bacillus subtilis

<400> SEQUENCE: 13
atgagaggat ctcaccatca ccatcaccat gggatcgatc atatgtttca tccgatagaa      60
gaagcactgg acgctttaaa aaaaggcgaa gtcatcatcg ttgtagatga tgaagacaga     120
gaaaatgaag gagactttgt ggctcttgcc gagcatgcaa cgccggaagt cattaacttt     180
atggcgacac atgggagagg actgatctgc acgccgctca gtgaggaaat cgcagacagg     240
cttgatcttc accctatggt tgagcataat acagactctc accacactgc atttaccgta     300
```

-continued

```
agcatagacc atcgtgaaac gaagacaggt atcagcgctc aagaaagatc ttttaccgtt    360
caagcattgc tggacagcaa atccgtgcca tctgattttc agcgtccggg gcacattttt    420
ccactgattg cgaaaaaagg aggtgtcctg aaaagagcgg ccatacaga agctgctgtt     480 gatcttgcta agcttgtgg atctccagga gccggcgtca tttgtgaaat tatgaatgaa     540
gacggaacga tggcgagagt gcctgagctc attgaaattg cgaaaaagca tcaattaaaa    600
atgatcacca ttaaggattt gattcaatgc cgttacaatc tgacaacact tgtcgagcgt    660
gaagttgaca ttacgctgcc tactgatttt gggacattta aggtttatgg atacacaaat    720
gaggtagatg aaaagagca tgtcgcattt gtgatgggag atgtgccgtt cggagaagaa     780
ccggtattgg tccgggtgca ttcagaatgt ctcacaggtg acgtgtttgg ctctcatcgc    840
tgtgattgcg gaccgcagct gcacgccacg ctgaaccaaa ttgccacaga aggccgtgga    900
gtgctcctgt acttgcgcca agaaggacga ggcatcggtt taatcaataa attaaaagct    960
tataagcttc aggaacaagg ctatgacacc gtagaagcca atgaggcgct tggattcttg   1020
ccggatcttc gcaactatgg catcggagca caaattttac gcgacctcgg tgtccggaat   1080
ataaagcttt tgacgaataa tccgcgaaaa atcgcaggcc ttgaaggcta cggactcagt   1140
atttcagaaa gagtgccgct tcaaatggag gcgaaagaac acaataaaaa atatttgcaa   1200
accaaaatga caagctagg tcatttactt catttctaa                           1239
```

<210> SEQ ID NO 14
<211> LENGTH: 412
<212> TYPE: PRT
<213> ORGANISM: Bacillus subtilis

<400> SEQUENCE: 14

Met Arg Gly Ser His His His His His His Gly Ile Asp His Met Phe
1               5                   10                  15

His Pro Ile Glu Glu Ala Leu Asp Ala Leu Lys Lys Gly Glu Val Ile
            20                  25                  30

Ile Val Val Asp Asp Glu Asp Arg Glu Asn Glu Gly Asp Phe Val Ala
        35                  40                  45

Leu Ala Glu His Ala Thr Pro Glu Val Ile Asn Phe Met Ala Thr His
    50                  55                  60

Gly Arg Gly Leu Ile Cys Thr Pro Leu Ser Glu Glu Ile Ala Asp Arg
65                  70                  75                  80

Leu Asp Leu His Pro Met Val Glu His Asn Thr Asp Ser His His Thr
                85                  90                  95

Ala Phe Thr Val Ser Ile Asp His Arg Glu Thr Lys Thr Gly Ile Ser
            100                 105                 110

Ala Gln Glu Arg Ser Phe Thr Val Gln Ala Leu Leu Asp Ser Lys Ser
        115                 120                 125

Val Pro Ser Asp Phe Gln Arg Pro Gly His Ile Phe Pro Leu Ile Ala
    130                 135                 140

Lys Lys Gly Gly Val Leu Lys Arg Ala Gly His Thr Glu Ala Ala Val
145                 150                 155                 160

Asp Leu Ala Glu Ala Cys Gly Ser Pro Gly Ala Gly Val Ile Cys Glu
                165                 170                 175

Ile Met Asn Glu Asp Gly Thr Met Ala Arg Val Pro Glu Leu Ile Glu
            180                 185                 190

Ile Ala Lys Lys His Gln Leu Lys Met Ile Thr Ile Lys Asp Leu Ile
        195                 200                 205

```
Gln Cys Arg Tyr Asn Leu Thr Thr Leu Val Glu Arg Glu Val Asp Ile
            210                 215                 220

Thr Leu Pro Thr Asp Phe Gly Thr Phe Lys Val Tyr Gly Tyr Thr Asn
225                 230                 235                 240

Glu Val Asp Gly Lys Glu His Val Ala Phe Val Met Gly Asp Val Pro
                245                 250                 255

Phe Gly Glu Pro Val Leu Val Arg Val His Ser Glu Cys Leu Thr
            260                 265                 270

Gly Asp Val Phe Gly Ser His Arg Cys Asp Cys Gly Pro Gln Leu His
            275                 280                 285

Ala Thr Leu Asn Gln Ile Ala Thr Glu Gly Arg Gly Val Leu Leu Tyr
290                 295                 300

Leu Arg Gln Glu Gly Arg Gly Ile Gly Leu Ile Asn Lys Leu Lys Ala
305                 310                 315                 320

Tyr Lys Leu Gln Glu Gln Gly Tyr Asp Thr Val Glu Ala Asn Glu Ala
                325                 330                 335

Leu Gly Phe Leu Pro Asp Leu Arg Asn Tyr Gly Ile Gly Ala Gln Ile
            340                 345                 350

Leu Arg Asp Leu Gly Val Arg Asn Ile Lys Leu Leu Thr Asn Asn Pro
355                 360                 365

Arg Lys Ile Ala Gly Leu Glu Gly Tyr Gly Leu Ser Ile Ser Glu Arg
370                 375                 380

Val Pro Leu Gln Met Glu Ala Lys Glu His Asn Lys Lys Tyr Leu Gln
385                 390                 395                 400

Thr Lys Met Asn Lys Leu Gly His Leu Leu His Phe
                405                 410

<210> SEQ ID NO 15
<211> LENGTH: 1239
<212> TYPE: DNA
<213> ORGANISM: Bacillus subtilis

<400> SEQUENCE: 15
atgagaggat ctcaccatca ccatcaccat gggatcgatc atatgtttca tccgatagaa      60
gaagcactgg acgctttaaa aaaaggcgaa gtcatcatcg ttgtagatga tgaagacaga     120
gaaaatgaag gagactttgt ggctcttgcc gagcatgcaa cgccggaagt cattaacttt     180
atggcgacac atgggagagg actgatctgc acgccgctca gtgaggaaat cgcagacagg     240
cttgatcttc accctatggt tgagcataat acagactctc accacactgc atttaccgta     300
agcatagacc atcgtgaaac gaagacaggt atcagcgctc aagaaagatc ttttaccgtt     360
caagcattgc tggacagcaa atccgtgcca tctgattttc agcgtccggg gcacattttt     420
ccactgattg cgaaaaaagg aggtgtcctg aaaagagcgg ccatacaga agctgctgtt     480 gatcttgctg aagcttgtgg atctccagga gccggcgtca tttgtgaaat tatgaatgaa     540
gacggaacga tggcgagagt gcctgagctc attgaaattg cgaaaaagca tcaattaaaa     600
atgatcacca ttaaggattt gattcaatgc cgttacaatc tgacaacact tgtcgagcgt     660
gaagttgaca ttacgctgcc tactgatttt gggacattta aggtttatgg atacacaaat     720
gaggtagatg gaaaagagca tgtcgcattt gtgatgggag atgtgccgtt cggagaagaa     780
ccggtattgg tccgggtgca ttcagaatgt ctcacaggtg acgtgtttgg ctctcatcgc     840
tgtgattgcg gaccgcagct gcacgccacg ctgaaccgaa ttgccacaga aggccgtgga     900
gtgctcctgt acttgcgcca agaaggacga ggcatcggtt taatcaataa attaaaagct     960
tataagcttc aggaacaagg ctatgacacc gtagaagcca atgaggcgct tggattcttg    1020
```

```
ccggatcttc gcaactatgg catcggagca caaattttac gcgacctcgg tgtccggaat    1080
ataaagcttt tgacgaataa tccgcgaaaa atcgcaggcc ttgaaggcta cggactcagt    1140
atttcagaaa gagtgccgct tcaaatggag gcgaaagaac acaataaaaa atatttgcaa    1200
accaaaatga acaagctagg tcatttactt catttctaa                           1239
```

<210> SEQ ID NO 16
<211> LENGTH: 412
<212> TYPE: PRT
<213> ORGANISM: Bacillus subtilis

<400> SEQUENCE: 16

```
Met Arg Gly Ser His His His His His His Gly Ile Asp His Met Phe
1               5                   10                  15

His Pro Ile Glu Glu Ala Leu Asp Ala Leu Lys Lys Gly Glu Val Ile
            20                  25                  30

Ile Val Val Asp Asp Glu Asp Arg Glu Asn Glu Gly Asp Phe Val Ala
        35                  40                  45

Leu Ala Glu His Ala Thr Pro Glu Val Ile Asn Phe Met Ala Thr His
    50                  55                  60

Gly Arg Gly Leu Ile Cys Thr Pro Leu Ser Glu Ile Ala Asp Arg
65                  70                  75                  80

Leu Asp Leu His Pro Met Val Glu His Asn Thr Asp Ser His His Thr
                85                  90                  95

Ala Phe Thr Val Ser Ile Asp His Arg Glu Thr Lys Thr Gly Ile Ser
            100                 105                 110

Ala Gln Glu Arg Ser Phe Thr Val Gln Ala Leu Leu Asp Ser Lys Ser
        115                 120                 125

Val Pro Ser Asp Phe Gln Arg Pro Gly His Ile Phe Pro Leu Ile Ala
    130                 135                 140

Lys Lys Gly Gly Val Leu Lys Arg Ala Gly His Thr Glu Ala Ala Val
145                 150                 155                 160

Asp Leu Ala Glu Ala Cys Gly Ser Pro Gly Ala Gly Val Ile Cys Glu
                165                 170                 175

Ile Met Asn Glu Asp Gly Thr Met Ala Arg Val Pro Glu Leu Ile Glu
            180                 185                 190

Ile Ala Lys Lys His Gln Leu Lys Met Ile Thr Ile Lys Asp Leu Ile
        195                 200                 205

Gln Cys Arg Tyr Asn Leu Thr Thr Leu Val Glu Arg Glu Val Asp Ile
    210                 215                 220

Thr Leu Pro Thr Asp Phe Gly Thr Phe Lys Val Tyr Gly Tyr Thr Asn
225                 230                 235                 240

Glu Val Asp Gly Lys Glu His Val Ala Phe Val Met Gly Asp Val Pro
                245                 250                 255

Phe Gly Glu Glu Pro Val Leu Val Arg Val His Ser Glu Cys Leu Thr
            260                 265                 270

Gly Asp Val Phe Gly Ser His Arg Cys Asp Cys Gly Pro Gln Leu His
        275                 280                 285

Ala Thr Leu Asn Arg Ile Ala Thr Glu Gly Arg Gly Val Leu Leu Tyr
    290                 295                 300

Leu Arg Gln Glu Gly Arg Gly Ile Gly Leu Ile Asn Lys Leu Lys Ala
305                 310                 315                 320

Tyr Lys Leu Gln Glu Gln Gly Tyr Asp Thr Val Glu Ala Asn Glu Ala
                325                 330                 335
```

-continued

```
Leu Gly Phe Leu Pro Asp Leu Arg Asn Tyr Gly Ile Gly Ala Gln Ile
                340                 345                 350

Leu Arg Asp Leu Gly Val Arg Asn Ile Lys Leu Leu Thr Asn Asn Pro
            355                 360                 365

Arg Lys Ile Ala Gly Leu Glu Gly Tyr Gly Leu Ser Ile Ser Glu Arg
    370                 375                 380

Val Pro Leu Gln Met Glu Ala Lys Glu His Asn Lys Lys Tyr Leu Gln
385                 390                 395                 400

Thr Lys Met Asn Lys Leu Gly His Leu Leu His Phe
                405                 410
```

<210> SEQ ID NO 17
<211> LENGTH: 1239
<212> TYPE: DNA
<213> ORGANISM: Bacillus subtilis

<400> SEQUENCE: 17

| | | |
|---|---|---|
| atgagaggat ctcaccatca ccatcaccat gggatcgatc atatgtttca tccgatagaa | 60 |
| gaagcactgg acgctttaaa aaaaggcgaa gtcatcatcg ttgtagatga tgaagacaga | 120 |
| gaaaatgaag gagactttgt ggctcttgcc gagcatgcaa cgccggaagt cattaacttt | 180 |
| atggcgacac atgggagagg actgatctgc acgccgctca gtgaggaaat cgcagacagg | 240 |
| cttgatcttc accctatggt tgagcataat acagactctc accacactgc atttaccgta | 300 |
| agcatagacc atcgtgaaac gaagacaggt atcagcgctc aagaaagatc ttttaccgtt | 360 |
| caagcattgc tggacagcaa atccgtgcca tctgattttc agcgtccggg gcacattttt | 420 |
| ccactgattg cgaaaaaagg aggtgtcctg aaaagagcgg ccatacaga agctgctgtt | 480 |
| gatcttgctg aagcttgtgg atctccagga gccggcgtca tttgtgaaat tatgaatgaa | 540 |
| gacggaacga tggcgagagt gcctgagctc attgaaattg cgaaaaagca tcaattaaaa | 600 |
| atgatcacca ttaaggattt gattcaatgc cgttacaatc tgacaacact tgtcgagcgt | 660 |
| gaagttgaca ttacgctgcc tactgatttt gggacattta aggtttatgg atacacaaat | 720 |
| gaggtagatg gaaagagca tgtcgcattt gtgatgggag atgtgccgtt cggagaagaa | 780 |
| ccggtattgt tccgggtgca ttcagaatgt ctcacaggtg acgtgttggg ctctcatcgc | 840 |
| tgtgattgcg gaccgcagct gcacgccact ctgaaccgaa ttgccacaga aggccgtgga | 900 |
| gtgctcctgt acttgcgcca agaaggacga ggcatcggtt taatcaataa attaaaagct | 960 |
| tataggcttc aggaacaagg ctatgacacc gtagaagcca atgaggcgct tggattcttg | 1020 |
| ccggatcttc gcaactatgg catcggagca caaattttac gcgacctcgg tgtccggaat | 1080 |
| ataaagcttt tgacgaataa tccgcgaaaa atcgcaggcc ttgaaggcta cggactcagt | 1140 |
| atttcagaaa gagtgccgct tcaaatggag gcgaaagaac acaataaaaa atatttgcaa | 1200 |
| accaaaatga caagctagg tcatttactt catttctaa | 1239 |

<210> SEQ ID NO 18
<211> LENGTH: 412
<212> TYPE: PRT
<213> ORGANISM: Bacillus subtilis

<400> SEQUENCE: 18

```
Met Arg Gly Ser His His His His His His Gly Ile Asp His Met Phe
1               5                   10                  15

His Pro Ile Glu Glu Ala Leu Asp Ala Leu Lys Lys Gly Glu Val Ile
            20                  25                  30
```

```
Ile Val Val Asp Asp Glu Asp Arg Glu Asn Glu Gly Asp Phe Val Ala
             35                  40                  45

Leu Ala Glu His Ala Thr Pro Glu Val Ile Asn Phe Met Ala Thr His
 50                  55                  60

Gly Arg Gly Leu Ile Cys Thr Pro Leu Ser Glu Glu Ile Ala Asp Arg
 65                  70                  75                  80

Leu Asp Leu His Pro Met Val Glu His Asn Thr Asp Ser His His Thr
                 85                  90                  95

Ala Phe Thr Val Ser Ile Asp His Arg Glu Thr Lys Thr Gly Ile Ser
                100                 105                 110

Ala Gln Glu Arg Ser Phe Thr Val Gln Ala Leu Leu Asp Ser Lys Ser
            115                 120                 125

Val Pro Ser Asp Phe Gln Arg Pro Gly His Ile Phe Pro Leu Ile Ala
130                 135                 140

Lys Lys Gly Gly Val Leu Lys Arg Ala Gly His Thr Glu Ala Ala Val
145                 150                 155                 160

Asp Leu Ala Glu Ala Cys Gly Ser Pro Gly Ala Gly Val Ile Cys Glu
                165                 170                 175

Ile Met Asn Glu Asp Gly Thr Met Ala Arg Val Pro Glu Leu Ile Glu
                180                 185                 190

Ile Ala Lys Lys His Gln Leu Lys Met Ile Thr Ile Lys Asp Leu Ile
            195                 200                 205

Gln Cys Arg Tyr Asn Leu Thr Thr Leu Val Glu Arg Glu Val Asp Ile
210                 215                 220

Thr Leu Pro Thr Asp Phe Gly Thr Phe Lys Val Tyr Gly Tyr Thr Asn
225                 230                 235                 240

Glu Val Asp Gly Lys Glu His Val Ala Phe Val Met Gly Asp Val Pro
                245                 250                 255

Phe Gly Glu Glu Pro Val Leu Val Arg Val His Ser Glu Cys Leu Thr
                260                 265                 270

Gly Asp Val Phe Gly Ser His Arg Cys Asp Cys Gly Pro Gln Leu His
            275                 280                 285

Ala Thr Leu Asn Arg Ile Ala Thr Glu Gly Arg Gly Val Leu Leu Tyr
290                 295                 300

Leu Arg Gln Glu Gly Arg Gly Ile Gly Leu Ile Asn Lys Leu Lys Ala
305                 310                 315                 320

Tyr Arg Leu Gln Glu Gln Gly Tyr Asp Thr Val Glu Ala Asn Glu Ala
                325                 330                 335

Leu Gly Phe Leu Pro Asp Leu Arg Asn Tyr Gly Ile Gly Ala Gln Ile
                340                 345                 350

Leu Arg Asp Leu Gly Val Arg Asn Ile Lys Leu Leu Thr Asn Asn Pro
            355                 360                 365

Arg Lys Ile Ala Gly Leu Glu Gly Tyr Gly Leu Ser Ile Ser Glu Arg
370                 375                 380

Val Pro Leu Gln Met Glu Ala Lys Glu His Asn Lys Lys Tyr Leu Gln
385                 390                 395                 400

Thr Lys Met Asn Lys Leu Gly His Leu Leu His Phe
                405                 410

<210> SEQ ID NO 19
<211> LENGTH: 1239
<212> TYPE: DNA
<213> ORGANISM: Bacillus subtilis
```

-continued

<400> SEQUENCE: 19

```
atgagaggat ctcaccatca ccatcaccat gggatcgatc atatgtttca tccgatagaa      60
gaagcactgg acgctttaaa aaaggcgaaa gtcatcatcg ttgtagatga tgaagacaga     120
gaaaatgaag gagactttgt ggctcttgcc gagcatgcaa cgccggaagt cattaacttt     180
atggcgacac atgggagagg actgatctgc acgccgctca gtgaggaaat cgcagacagg     240
cttgatcttc accctatggt tgagcataat acagactctc accacactgc atttaccgta     300
agcatagacc atcgtgaaac gaagacaggt atcagcgctc aagaaagatc ttttaccgtt     360
caagcattgc tggacagcaa atccgtgcca tctgattttc agcgtccggg gcacattttt     420
ccactgattg cgaaaaaagg aggtgtcctg aaaagagcgg ccatacaga agctgctgtt      480
gatcttgctg aagcttgtgg atctccagga gccggcgtca tttgtgaaat tatgaatgaa     540
gacggaacga tggcgagagt gcctgagctc attgaaattg cgaaaaagca tcaattaaaa     600
atgatcacca ttaaggattt gattcaatac cgttacaatc tgacaacact tgtcgagcgt     660
gaagttgaca ttacgctgcc tactgatttt gggacatttg aggtttatgg atacacaaat     720
gaggtagatg aaaagagca tgtcgcattt gtgatgggag atgtgccgtt cggagaagaa     780
ccggtattgg tccgggtgca ttcagaatgt ctcacaggtg acgtgtttgg ctctcatcgc     840
tgtgattgcg caccgcagct gcacgccgcg ctgaaccaaa ttgccgcaga aggccgtgga     900
gtgctcctgt acttgcgcca agaaggacga ggcatcggtt taatcaataa attaaaagct     960
tataagcttc aggaacaagg ctatgacacc gtagaagcca atgaggcgct tggattcttg    1020
ccggatcttc gcaactatgg catcggagca caaattttac gcgacctcgg tgtccggaat    1080
atgaagcttt tgacgaataa tccgcgaaaa atcgcaggcc ttgaaggcta cggactcagt    1140
atttcagaaa gagtgccgct tcaaatggag gcgaaagaac acaataaaaa atatttgcaa    1200
accaaaatga acaagctagg tcatttactt catttctaa                           1239
```

<210> SEQ ID NO 20
<211> LENGTH: 412
<212> TYPE: PRT
<213> ORGANISM: Bacillus subtilis

<400> SEQUENCE: 20

```
Met Arg Gly Ser His His His His His His Gly Ile Asp His Met Phe
1               5                   10                  15

His Pro Ile Glu Glu Ala Leu Asp Ala Leu Lys Lys Gly Glu Val Ile
            20                  25                  30

Ile Val Val Asp Asp Glu Asp Arg Glu Asn Glu Gly Asp Phe Val Ala
        35                  40                  45

Leu Ala Glu His Ala Thr Pro Glu Val Ile Asn Phe Met Ala Thr His
    50                  55                  60

Gly Arg Gly Leu Ile Cys Thr Pro Leu Ser Glu Glu Ile Ala Asp Arg
65                  70                  75                  80

Leu Asp Leu His Pro Met Val Glu His Asn Thr Asp Ser His Thr
                85                  90                  95

Ala Phe Thr Val Ser Ile Asp His Arg Glu Thr Lys Thr Gly Ile Ser
            100                 105                 110

Ala Gln Glu Arg Ser Phe Thr Val Gln Ala Leu Leu Asp Ser Lys Ser
        115                 120                 125

Val Pro Ser Asp Phe Gln Arg Pro Gly His Ile Phe Pro Leu Ile Ala
    130                 135                 140
```

```
Lys Lys Gly Gly Val Leu Lys Arg Ala Gly His Thr Glu Ala Ala Val
145                 150                 155                 160

Asp Leu Ala Glu Ala Cys Gly Ser Pro Gly Ala Gly Val Ile Cys Glu
            165                 170                 175

Ile Met Asn Glu Asp Gly Thr Met Ala Arg Val Pro Glu Leu Ile Glu
        180                 185                 190

Ile Ala Lys Lys His Gln Leu Lys Met Ile Thr Ile Lys Asp Leu Ile
    195                 200                 205

Gln Tyr Arg Tyr Asn Leu Thr Thr Leu Val Glu Arg Glu Val Asp Ile
210                 215                 220

Thr Leu Pro Thr Asp Phe Gly Thr Phe Glu Val Tyr Gly Tyr Thr Asn
225                 230                 235                 240

Glu Val Asp Gly Lys Glu His Val Ala Phe Val Met Gly Asp Val Pro
                245                 250                 255

Phe Gly Glu Glu Pro Val Leu Val Arg Val His Ser Glu Cys Leu Thr
            260                 265                 270

Gly Asp Val Phe Gly Ser His Arg Cys Asp Cys Ala Pro Gln Leu His
        275                 280                 285

Ala Ala Leu Asn Gln Ile Ala Ala Glu Gly Arg Gly Val Leu Leu Tyr
290                 295                 300

Leu Arg Gln Glu Gly Arg Gly Ile Gly Leu Ile Asn Lys Leu Lys Ala
305                 310                 315                 320

Tyr Lys Leu Gln Glu Gln Gly Tyr Asp Thr Val Glu Ala Asn Glu Ala
                325                 330                 335

Leu Gly Phe Leu Pro Asp Leu Arg Asn Tyr Gly Ile Gly Ala Gln Ile
            340                 345                 350

Leu Arg Asp Leu Gly Val Arg Asn Met Lys Leu Leu Thr Asn Asn Pro
        355                 360                 365

Arg Lys Ile Ala Gly Leu Glu Gly Tyr Gly Leu Ser Ile Ser Glu Arg
370                 375                 380

Val Pro Leu Gln Met Glu Ala Lys Glu His Asn Lys Lys Tyr Leu Gln
385                 390                 395                 400

Thr Lys Met Asn Lys Leu Gly His Leu Leu His Phe
                405                 410

<210> SEQ ID NO 21
<211> LENGTH: 1239
<212> TYPE: DNA
<213> ORGANISM: Bacillus subtilis

<400> SEQUENCE: 21
atgagaggat ctcaccatca ccatcaccat gggatcgatc atatgtttca tccgatagaa      60
gaagcactgg acgctttaaa aaaaggcgaa gtcatcatcg ttgtagatga tgaagacaga     120
gaaaatgaag gagactttgt ggctcttgcc gagcatgcaa cgccggaagt cattaacttt     180
atggcgacac atgggagagg actgatctgc acgccgctca gtgaggaaat cgcagacagg     240
cttgatcttc accctatggt tgagcataat acagactctc accacactgc atttaccgta     300
agcatagacc atcgtgaaac gaagacaggt atcagcgctc aagaaagatc ttttaccgtt     360
caagcattgc tggacagcaa atccgtgcca tctgattttc agcgtccggg gcacattttt     420
ccactgattg cgaaaaaagg aggtgtcctg aaaagagcgg ccatacaga agctgctgtt      480 gatcttgctg aagcttgtgg atctccagga gccggcgtca tttgtgaaat tatgaatgaa     540
gacggaacga tggcgagagt gcctgagctc attgaaattg cgaaaaagca tcaattaaaa     600
atgatcacca ttaaggattt gattcaatgc cgttacaatc tgacaacact tgtcgagcgt     660
```

-continued

```
gaagttgaca ttacgctgcc tactgatttt gggacattta aggtttatgg atacacaaat    720
gaggtagatg gaaaagagca tgtcgcattt gtgatgggag atgtgccgtt cggagaagaa    780
ccggtattgg tccgggtgca ttcagaatgt ctcacaggtg acgtgtttgg ctctcatcgc    840
tgtgattgcg gaccgcagct gcacgccacg ctgaaccgaa ttgccacaga aggccgtgga    900
gtgctcctgt acttgcgcca agaaggacga ggcatcggtt taatcaataa attaaaagct    960
tataggcttc aggaacaagg ctatgacacc gtagaagcca atgaggcgct tggatacttg   1020
ccggatcttc gcaactatgg catcggagca caaattttac gcgacctcgg tgtccggaat   1080
ataaagcttt tgacgaataa tccgcgaaaa atcgcaggcc ttgaaggcta cggactcagt   1140
atttcagaaa gagtgccgct tcaaatggag gcgaaagaac acaataaaaa atatttgcaa   1200
accaaaatga acaagctagg tcatttactt catttctaa                          1239
```

<210> SEQ ID NO 22
<211> LENGTH: 412
<212> TYPE: PRT
<213> ORGANISM: Bacillus subtilis

<400> SEQUENCE: 22

```
Met Arg Gly Ser His His His His His Gly Ile Asp His Met Phe
1               5                   10                  15

His Pro Ile Glu Glu Ala Leu Asp Ala Leu Lys Lys Gly Glu Val Ile
            20                  25                  30

Ile Val Val Asp Asp Glu Asp Arg Glu Asn Glu Gly Asp Phe Val Ala
        35                  40                  45

Leu Ala Glu His Ala Thr Pro Glu Val Ile Asn Phe Met Ala Thr His
    50                  55                  60

Gly Arg Gly Leu Ile Cys Thr Pro Leu Ser Glu Ile Ala Asp Arg
65                  70                  75                  80

Leu Asp Leu His Pro Met Val Glu His Asn Thr Asp Ser His Thr
                85                  90                  95

Ala Phe Thr Val Ser Ile Asp His Arg Glu Thr Lys Thr Gly Ile Ser
            100                 105                 110

Ala Gln Glu Arg Ser Phe Thr Val Gln Ala Leu Leu Asp Ser Lys Ser
        115                 120                 125

Val Pro Ser Asp Phe Gln Arg Pro Gly His Ile Phe Pro Leu Ile Ala
    130                 135                 140

Lys Lys Gly Gly Val Leu Lys Arg Ala Gly His Thr Glu Ala Ala Val
145                 150                 155                 160

Asp Leu Ala Glu Ala Cys Gly Ser Pro Gly Ala Gly Val Ile Cys Glu
                165                 170                 175

Ile Met Asn Glu Asp Gly Thr Met Ala Arg Val Pro Glu Leu Ile Glu
            180                 185                 190

Ile Ala Lys Lys His Gln Leu Lys Met Ile Thr Ile Lys Asp Leu Ile
        195                 200                 205

Gln Cys Arg Tyr Asn Leu Thr Thr Leu Val Glu Arg Glu Val Asp Ile
    210                 215                 220

Thr Leu Pro Thr Asp Phe Gly Thr Phe Lys Val Tyr Gly Tyr Thr Asn
225                 230                 235                 240

Glu Val Asp Gly Lys Glu His Val Ala Phe Val Met Gly Asp Val Pro
                245                 250                 255

Phe Gly Glu Glu Pro Val Leu Val Arg Val His Ser Glu Cys Leu Thr
            260                 265                 270
```

```
Gly Asp Val Phe Gly Ser His Arg Cys Asp Cys Gly Pro Gln Leu His
            275                 280                 285

Ala Thr Leu Asn Arg Ile Ala Thr Glu Gly Arg Gly Val Leu Leu Tyr
    290                 295                 300

Leu Arg Gln Glu Gly Arg Gly Ile Gly Leu Ile Asn Lys Leu Lys Ala
305                 310                 315                 320

Tyr Arg Leu Gln Glu Gln Gly Tyr Asp Thr Val Glu Ala Asn Glu Ala
                325                 330                 335

Leu Gly Tyr Leu Pro Asp Leu Arg Asn Tyr Ile Gly Ala Gln Ile
                340                 345                 350

Leu Arg Asp Leu Gly Val Arg Asn Ile Lys Leu Leu Thr Asn Asn Pro
    355                 360                 365

Arg Lys Ile Ala Gly Leu Glu Gly Tyr Gly Leu Ser Ile Ser Glu Arg
    370                 375                 380

Val Pro Leu Gln Met Glu Ala Lys Glu His Asn Lys Lys Tyr Leu Gln
385                 390                 395                 400

Thr Lys Met Asn Lys Leu Gly His Leu Leu His Phe
                405                 410
```

<210> SEQ ID NO 23
<211> LENGTH: 1239
<212> TYPE: DNA
<213> ORGANISM: Bacillus subtilis

<400> SEQUENCE: 23

| | | |
|---|---|---|
| atgagaggat ctcaccatca ccatcaccat gggatcgatc atatgtttca tccgatagaa | 60 |
| gaagcactgg acgctttaaa aaaaggcgaa gtcatcatcg ttgtagatga tgaagacaga | 120 |
| gaaaatgaag gagactttgt ggctcttgcc gagcatgcaa cgccggaagt cattaacttt | 180 |
| atggcgacac atgggagagg actgatctgc acgccgctca gtgaggaaat cgcagacagg | 240 |
| cttgatcttc accctatggt tgagcataat acagactctc accacactgc atttaccgta | 300 |
| agcatagacc atcgtgaaac gaagacaggt atcagcgctc aagaaagatc ttttaccgtt | 360 |
| caagcattgc tggacagcaa atccgtgcca tctgattttc agcgtccggg gcacattttt | 420 |
| ccactgattg cgaaaaaagg aggtgtcctg aaaagagcgg ccatacaga agctgctgtt | 480 |
| gatcttgctg aagcttgtgg atctccagga gccggcgtca tttgtgaaat tatgaatgaa | 540 |
| gacggaacga tggcgagagt gcctgagctc attgaaattg cgaaaaagca tcaattaaaa | 600 |
| atgatcacca ttaaggattt gattcaatac cgttacaatc tgacaacact tgtcgagcgt | 660 |
| gaagttgaca ttacgctgcc tactgatttt gggacattta aggtttatgg atacacaaat | 720 |
| gaggtagatg gaaaagagca tgtcgcattt gtgatgggag atgtgccgtt cggagaagaa | 780 |
| ccggtattgg tccgggtgca ttcagaatgt ctcacaggtg acgtgtttgg ctctcatcgc | 840 |
| tgtgattgca gaccgcagct gcacgccgcg ctgaaccaaa ttgccgcaga aggccgtgga | 900 |
| gtgctcctgt acttgcgcca agaaggacga ggcatcggtt aatcaataa attaaaagct | 960 |
| tataagcttc aggaacaagg ctatgacacc gtagaagcca atgaggcgct tggattcttg | 1020 |
| ccggatcttc gcaactatgg catcggagca caaattttac gcgacctcgg tgtccggaat | 1080 |
| atgaagcttt tgacgaataa tccgcgaaaa atcgcaggcc ttgaaggcta cggactcagt | 1140 |
| atttcagaaa gagtgccgct tcaaatggag gcgaagaac acaataaaaa atatttgcaa | 1200 |
| accaaaatga acaagctagg tcatttactt catttctaa | 1239 |

<210> SEQ ID NO 24
<211> LENGTH: 412
<212> TYPE: PRT
<213> ORGANISM: Bacillus subtilis

<400> SEQUENCE: 24

Met Arg Gly Ser His His His His His His Gly Ile Asp His Met Phe
1               5                   10                  15

His Pro Ile Glu Glu Ala Leu Asp Ala Leu Lys Lys Gly Glu Val Ile
            20                  25                  30

Ile Val Val Asp Asp Glu Asp Arg Glu Asn Glu Gly Asp Phe Val Ala
        35                  40                  45

Leu Ala Glu His Ala Thr Pro Glu Val Ile Asn Phe Met Ala Thr His
    50                  55                  60

Gly Arg Gly Leu Ile Cys Thr Pro Leu Ser Glu Ile Ala Asp Arg
65                  70                  75                  80

Leu Asp Leu His Pro Met Val Glu His Asn Thr Asp Ser His His Thr
                85                  90                  95

Ala Phe Thr Val Ser Ile Asp His Arg Glu Thr Lys Thr Gly Ile Ser
            100                 105                 110

Ala Gln Glu Arg Ser Phe Thr Val Gln Ala Leu Leu Asp Ser Lys Ser
        115                 120                 125

Val Pro Ser Asp Phe Gln Arg Pro Gly His Ile Phe Pro Leu Ile Ala
    130                 135                 140

Lys Lys Gly Gly Val Leu Lys Arg Ala Gly His Thr Glu Ala Ala Val
145                 150                 155                 160

Asp Leu Ala Glu Ala Cys Gly Ser Pro Gly Ala Gly Val Ile Cys Glu
                165                 170                 175

Ile Met Asn Glu Asp Gly Thr Met Ala Arg Val Pro Glu Leu Ile Glu
            180                 185                 190

Ile Ala Lys Lys His Gln Leu Lys Met Ile Thr Ile Lys Asp Leu Ile
        195                 200                 205

Gln Tyr Arg Tyr Asn Leu Thr Thr Leu Val Glu Arg Glu Val Asp Ile
    210                 215                 220

Thr Leu Pro Thr Asp Phe Gly Thr Phe Lys Val Tyr Gly Tyr Thr Asn
225                 230                 235                 240

Glu Val Asp Gly Lys Glu His Val Ala Phe Val Met Gly Asp Val Pro
                245                 250                 255

Phe Gly Glu Glu Pro Val Leu Val Arg Val His Ser Glu Cys Leu Thr
            260                 265                 270

Gly Asp Val Phe Gly Ser His Arg Cys Asp Cys Arg Pro Gln Leu His
        275                 280                 285

Ala Ala Leu Asn Gln Ile Ala Ala Glu Gly Arg Gly Val Leu Leu Tyr
    290                 295                 300

Leu Arg Gln Glu Gly Arg Gly Ile Gly Leu Ile Asn Lys Leu Lys Ala
305                 310                 315                 320

Tyr Lys Leu Gln Glu Gln Gly Tyr Asp Thr Val Glu Ala Asn Glu Ala
                325                 330                 335

Leu Gly Phe Leu Pro Asp Leu Arg Asn Tyr Gly Ile Gly Ala Gln Ile
            340                 345                 350

Leu Arg Asp Leu Gly Val Arg Asn Met Lys Leu Leu Thr Asn Asn Pro
        355                 360                 365

Arg Lys Ile Ala Gly Leu Glu Gly Tyr Gly Leu Ser Ile Ser Glu Arg
    370                 375                 380

Val Pro Leu Gln Met Glu Ala Lys Glu His Asn Lys Lys Tyr Leu Gln
385                 390                 395                 400

Thr Lys Met Asn Lys Leu Gly His Leu Leu His Phe
            405                 410

<210> SEQ ID NO 25
<211> LENGTH: 1239
<212> TYPE: DNA
<213> ORGANISM: Bacillus subtilis

<400> SEQUENCE: 25
atgagaggat ctcaccatca ccatcaccat gggatcgatc atatgtttca tccgatagaa      60
gaagcactgg acgcttttaaa aaaaggcgaa gtcatcatcg ttgtagatga tgaagacaga     120
gaaaatgaag gagactttgt ggctcttgcc gagcatgcaa cgccggaagt cattaacttt     180
atggcgacac atgggagagg actgatctgc acgccgctca gtgaggaaat cgcagacagg     240
cttgatcttc accctatggt tgagcataat acagactctc accacactgc atttaccgta     300
agcatagacc atcgtgaaac gaagacaggt atcagcgctc aagaaagatc ttttaccgtt     360
caagcattgc tggacagcaa atccgtgcca tctgattttc agcgtccggg gcacattttt     420
ccactgattg cgaaaaaagg aggtgtcctg aaaagagcgg ccatacagaa gctgctgtt      480 gatcttgctg aagcttgtgg atctccagga gccggcgtca tttgtgaaat tatgaatgaa     540
gacggaacga tggcgagagt gcctgagctc attgaaattg cgaaaaagca tcaattaaaa     600
atgatcacca ttaaggattt gattcaatgc cgttacaatc tgacaacact tgtcgagcgt     660
gaagttgaca ttacgctgcc tactgatttt gggacattta aggtttatgg atacacaaat     720
gaggtagatg aaaagagca tgtcgcattt gtgatgggag atgtgccgtt cggagaagaa     780
ccggtattgg tccgggtgca ttcagaatgt ctcacaggtg acgcgtttgg ctctcatcgc     840
tgtgattgcg gaccgcagct gcacgccacg ctgaaccaaa ttgccgcaga aggccgtgga     900
gtgctcctgt acttgcgcca agaaggacga ggcatcggtt taatcaataa attaaaagct     960
tataagcttc aggaacaagg ctatgacacc gtagaagcca atgaggcgct tggattcttg    1020
ccggatcttc gcaactatgg catcggagca caaatttac gcgacctcgg tgtccggaat    1080
atgaagcttt tgacgaataa tccgcgaaaa atcgcaggcc ttgaaggcta cggactcagt    1140
atttcagaaa gagtgccgct tcaaatggag gcgaaagaac acaataaaaa atatttgcaa    1200
accaaaatga acaagctagg tcatttactt catttctaa                            1239

<210> SEQ ID NO 26
<211> LENGTH: 412
<212> TYPE: PRT
<213> ORGANISM: Bacillus subtilis

<400> SEQUENCE: 26

Met Arg Gly Ser His His His His His His Gly Ile Asp His Met Phe
1               5                   10                  15

His Pro Ile Glu Glu Ala Leu Asp Ala Leu Lys Lys Gly Glu Val Ile
            20                  25                  30

Ile Val Val Asp Asp Glu Asp Arg Glu Asn Glu Gly Asp Phe Val Ala
        35                  40                  45

Leu Ala Glu His Ala Thr Pro Glu Val Ile Asn Phe Met Ala Thr His
    50                  55                  60

Gly Arg Gly Leu Ile Cys Thr Pro Leu Ser Glu Glu Ile Ala Asp Arg
65                  70                  75                  80

```
Leu Asp Leu His Pro Met Val Glu His Asn Thr Asp Ser His His Thr
             85                  90                  95

Ala Phe Thr Val Ser Ile Asp His Arg Glu Thr Lys Thr Gly Ile Ser
            100                 105                 110

Ala Gln Glu Arg Ser Phe Thr Val Gln Ala Leu Leu Asp Ser Lys Ser
        115                 120                 125

Val Pro Ser Asp Phe Gln Arg Pro Gly His Ile Phe Pro Leu Ile Ala
    130                 135                 140

Lys Gly Gly Val Leu Lys Arg Ala Gly His Thr Glu Ala Ala Val
145                 150                 155                 160

Asp Leu Ala Glu Ala Cys Gly Ser Pro Gly Ala Gly Val Ile Cys Glu
                165                 170                 175

Ile Met Asn Glu Asp Gly Thr Met Ala Arg Val Pro Glu Leu Ile Glu
            180                 185                 190

Ile Ala Lys Lys His Gln Leu Lys Met Ile Thr Ile Lys Asp Leu Ile
        195                 200                 205

Gln Cys Arg Tyr Asn Leu Thr Thr Leu Val Glu Arg Glu Val Asp Ile
    210                 215                 220

Thr Leu Pro Thr Asp Phe Gly Thr Phe Lys Val Tyr Gly Tyr Thr Asn
225                 230                 235                 240

Glu Val Asp Gly Lys Glu His Val Ala Phe Val Met Gly Asp Val Pro
                245                 250                 255

Phe Gly Glu Glu Pro Val Leu Val Arg Val His Ser Glu Cys Leu Thr
            260                 265                 270

Gly Asp Ala Phe Gly Ser His Arg Cys Asp Cys Gly Pro Gln Leu His
        275                 280                 285

Ala Thr Leu Asn Gln Ile Ala Ala Glu Gly Arg Gly Val Leu Leu Tyr
    290                 295                 300

Leu Arg Gln Glu Gly Arg Gly Ile Gly Leu Ile Asn Lys Leu Lys Ala
305                 310                 315                 320

Tyr Lys Leu Gln Glu Gln Gly Tyr Asp Thr Val Glu Ala Asn Glu Ala
                325                 330                 335

Leu Gly Phe Leu Pro Asp Leu Arg Asn Tyr Gly Ile Gly Ala Gln Ile
            340                 345                 350

Leu Arg Asp Leu Gly Val Arg Asn Met Lys Leu Leu Thr Asn Asn Pro
        355                 360                 365

Arg Lys Ile Ala Gly Leu Glu Gly Tyr Gly Leu Ser Ile Ser Glu Arg
    370                 375                 380

Val Pro Leu Gln Met Glu Ala Lys Glu His Asn Lys Lys Tyr Leu Gln
385                 390                 395                 400

Thr Lys Met Asn Lys Leu Gly His Leu Leu His Phe
                405                 410

<210> SEQ ID NO 27
<211> LENGTH: 61
<212> TYPE: DNA
<213> ORGANISM: Artificial
<220> FEATURE:
<223> OTHER INFORMATION: Primer RibA 1S

<400> SEQUENCE: 27
atgagaggat ctcaccatca ccatcaccat gggatcgatc atatgtttca tccgatagaa     60
g                                                                    61
```

```
<210> SEQ ID NO 28
<211> LENGTH: 38
<212> TYPE: DNA
<213> ORGANISM: Artificial
<220> FEATURE:
<223> OTHER INFORMATION: Primer RibA 1AS

<400> SEQUENCE: 28
tataattgga tccttagaaa tgaagtaaat gacctagc                                38

<210> SEQ ID NO 29
<211> LENGTH: 54
<212> TYPE: DNA
<213> ORGANISM: Artificial
<220> FEATURE:
<223> OTHER INFORMATION: Primer RibA 2S

<400> SEQUENCE: 29
attaatgaat tcattaaaga ggagaaatta actatgagag gatctcacca tcac              54

<210> SEQ ID NO 30
<211> LENGTH: 31
<212> TYPE: DNA
<213> ORGANISM: Artificial
<220> FEATURE:
<223> OTHER INFORMATION: Primer RibANde+1

<400> SEQUENCE: 30
ggagggtttc atatgtttca tccgatagaa g                                       31

<210> SEQ ID NO 31
<211> LENGTH: 21
<212> TYPE: DNA
<213> ORGANISM: Artificial
<220> FEATURE:
<223> OTHER INFORMATION: Primer RibA4AS

<400> SEQUENCE: 31
taattaagct tggatcctta g                                                  21

<210> SEQ ID NO 32
<211> LENGTH: 906
<212> TYPE: DNA
<213> ORGANISM: Ashbya gossypii

<400> SEQUENCE: 32
atgactgaat acacagtgcc agaagtgagg tgtgtcgcac gcgcgcgcat accgacggta        60
cagggcaccg atgtcttcct ccatctatac cacaactcga tcgacagcaa ggaacaccta       120
gcgattgtct cggcgagaa catacgctcg cggagtctgt tccggtaccg gaaagacgac        180
acgcagcagg cgcggatggt gcggggcgcc tacgtgggcc agctgtaccc cgggcggacc       240
gaggcagacg cggatcggcg tcagggcctg gagctgcggt ttgatgagac agggcagctg       300
gtggtggagc gggcgacgac gtggaccagg gagccgacac tggtgcggct gcactcggag       360
tgttacacgg gcgagacggc gtggagcgcg cggtgcgact gcgggagca gttcgaccag        420 gcgggtaagc tgatggctgc ggcgacagag ggcgaggtgg ttggcggtgc ggggcacggc       480
gtgatcgtgt acctgcggca ggagggccgc ggcatcgggc taggcgagaa gctgaaggcg       540
tacaacctgc aggacctggg cgcggacacg gtgcaggcga acgagctgct caaccaccct      600
gcggacgcgc gcgacttctc gttggggcgc gcaatcctac tggacctcgg tatcgaggac      660
atccggttgc tcacgaataa ccccgacaag gtgcagcagg tgcactgtcc gccggcgcta      720
cgctgcatcg agcgggtgcc catggtgccg ctttcatgga ctcagcccac acagggcgtg      780
```

```
cgctcgcgcg agctggacgg ctacctgcgc gccaaggtcg agcgcatggg gcacatgctg    840
cagcggccgc tggtgctgca cacgtctgcg gcggccgagc tcccccgcgc caacacacac    900
atataa                                                               906
```

<210> SEQ ID NO 33
<211> LENGTH: 301
<212> TYPE: PRT
<213> ORGANISM: Ashbya gossypii

<400> SEQUENCE: 33

```
Met Thr Glu Tyr Thr Val Pro Glu Val Arg Cys Val Ala Arg Ala Arg
1               5                   10                  15

Ile Pro Thr Val Gln Gly Thr Asp Val Phe Leu His Leu Tyr His Asn
            20                  25                  30

Ser Ile Asp Ser Lys Glu His Leu Ala Ile Val Phe Gly Glu Asn Ile
        35                  40                  45

Arg Ser Arg Ser Leu Phe Arg Tyr Arg Lys Asp Asp Thr Gln Gln Ala
    50                  55                  60

Arg Met Val Arg Gly Ala Tyr Val Gly Gln Leu Tyr Pro Gly Arg Thr
65                  70                  75                  80

Glu Ala Asp Ala Asp Arg Arg Gln Gly Leu Glu Leu Arg Phe Asp Glu
                85                  90                  95

Thr Gly Gln Leu Val Val Glu Arg Ala Thr Thr Trp Thr Arg Glu Pro
            100                 105                 110

Thr Leu Val Arg Leu His Ser Glu Cys Tyr Thr Gly Glu Thr Ala Trp
        115                 120                 125

Ser Ala Arg Cys Asp Cys Gly Glu Gln Phe Asp Gln Ala Gly Lys Leu
    130                 135                 140

Met Ala Ala Thr Glu Gly Glu Val Val Gly Ala Gly His Gly
145                 150                 155                 160

Val Ile Val Tyr Leu Arg Gln Glu Gly Arg Gly Ile Gly Leu Gly Glu
                165                 170                 175

Lys Leu Lys Ala Tyr Asn Leu Gln Asp Leu Gly Ala Asp Thr Val Gln
            180                 185                 190

Ala Asn Glu Leu Leu Asn His Pro Ala Asp Ala Arg Asp Phe Ser Leu
        195                 200                 205

Gly Arg Ala Ile Leu Leu Asp Leu Gly Ile Glu Asp Ile Arg Leu Leu
    210                 215                 220

Thr Asn Asn Pro Asp Lys Val Gln Gln Val His Cys Pro Pro Ala Leu
225                 230                 235                 240

Arg Cys Ile Glu Arg Val Pro Met Val Pro Leu Ser Trp Thr Gln Pro
                245                 250                 255

Thr Gln Gly Val Arg Ser Arg Glu Leu Asp Gly Tyr Leu Arg Ala Lys
            260                 265                 270

Val Glu Arg Met Gly His Met Leu Gln Arg Pro Leu Val Leu His Thr
        275                 280                 285

Ser Ala Ala Ala Glu Leu Pro Arg Ala Asn Thr His Ile
    290                 295                 300
```

<210> SEQ ID NO 34
<211> LENGTH: 591
<212> TYPE: DNA
<213> ORGANISM: Escherichia coli

<400> SEQUENCE: 34

```
atgcagctta aacgtgtggc agaagccaaa ctgccaaccc catggggcga tttcctgatg     60
gtgggatttg aagaactggc aaccggacac gatcatgtcg cgctagtcta tggcgatatt    120
tccgggcata ccccggtact tgcgcgcgtc cattccgaat gtctgaccgg tgacgccctg    180
ttcagcttgc gctgcgattg tggcttccag ctcgaagcgg cattgacgca aattgccgag    240
gaaggccgtg gtattttgct gtatcaccgt caggaaggtc gtaacattgg tctgctgaat    300
aaaatccgcg cttacgcact gcaggatcaa ggttacgata ccgtagaggc taaccaccag    360
ttaggcttcg ccgctgatga gcgcgacttc actctttgcg ctgatatgtt caaactcctt    420
ggcgtcaatg aagtccgctt gttaaccaat aacccgaaaa agtcgaaat ctgaccgaa      480
gcagggatta atattgttga acgcgtacca ttgattgtag gtcgtaaccc caataacgaa    540
cattatctcg ataccaaagc cgagaaaatg ggccatttgc tgaacaaata a              591
```

<210> SEQ ID NO 35
<211> LENGTH: 196
<212> TYPE: PRT
<213> ORGANISM: Escherichia coli

<400> SEQUENCE: 35

```
Met Gln Leu Lys Arg Val Ala Glu Ala Lys Leu Pro Thr Pro Trp Gly
 1               5                  10                  15
Asp Phe Leu Met Val Gly Phe Glu Glu Leu Ala Thr Gly His Asp His
                20                  25                  30
Val Ala Leu Val Tyr Gly Asp Ile Ser Gly His Thr Pro Val Leu Ala
            35                  40                  45
Arg Val His Ser Glu Cys Leu Thr Gly Asp Ala Leu Phe Ser Leu Arg
        50                  55                  60
Cys Asp Cys Gly Phe Gln Leu Glu Ala Ala Leu Thr Gln Ile Ala Glu
 65                  70                  75                  80
Glu Gly Arg Gly Ile Leu Leu Tyr His Arg Gln Glu Gly Arg Asn Ile
                 85                  90                  95
Gly Leu Leu Asn Lys Ile Arg Ala Tyr Ala Leu Gln Asp Gln Gly Tyr
            100                 105                 110
Asp Thr Val Glu Ala Asn His Gln Leu Gly Phe Ala Ala Asp Glu Arg
        115                 120                 125
Asp Phe Thr Leu Cys Ala Asp Met Phe Lys Leu Leu Gly Val Asn Glu
    130                 135                 140
Val Arg Leu Leu Thr Asn Asn Pro Lys Lys Val Glu Ile Leu Thr Glu
145                 150                 155                 160
Ala Gly Ile Asn Ile Val Glu Arg Val Pro Leu Ile Val Gly Arg Asn
                165                 170                 175
Pro Asn Asn Glu His Tyr Leu Asp Thr Lys Ala Glu Lys Met Gly His
            180                 185                 190
Leu Leu Asn Lys
        195
```

<210> SEQ ID NO 36
<211> LENGTH: 1269
<212> TYPE: DNA
<213> ORGANISM: Corynebacterium glutamicum

<400> SEQUENCE: 36

```
gtgagtgaac atgagcaggc acacagccaa ttagattctg ttgaagaggc catcgctgac     60
atcgctgcgg gtaaagccgt cgtggtggta gatgatgaag atcgtgaaaa tgaaggcgac    120
```

```
atcatctttg ccgccgaatt agccactcca gaattagtcg ctttcatggt gcgttattcc    180
tcgggataca tctgtgcgcc attaaccgca aaggatgcag atcgtcttga tctgcctccg    240
atgaccgcgc acaatcagga tgcccgcggc accgcttaca ccgtgaccgt tgatgccaac    300
accggcacca caggcatttc tgcaacagac cgcgcccaca ctttgcgctt gcttgctgat    360
ccagaagccg accgcacgga tttcacccgt cccggacacg ttgtgccact gcgtgctcgt    420
gaaggtggcg tcttggtgcg cgctggacac accgaagcag ctgtcgattt ggctcgcgct    480
gcaggcctgc gcccagcagg tgttatctgc gaagtggtca gtgaagagga ccccaccggc    540
atggctcggg ttcctgagct gcgccgcttc tgcgatgagc acgatctgaa gctgatctct    600
attgagcagc tcattgagtg gcgtcgcaag aatgaaattt tggtggagcg ccaggtggaa    660
actgtgctgc ctaccgattt cggcacgttc aaggctgttg gttaccgttc catcatcgat    720
ggcaccgagc ttgttgccat tgttgccggc gacgtggcat ccgacggtgg cgaaaacgtc    780
ctggttcgag tccactctga gtgcttgact ggtgatgttt ttggatcccg cgctgcgac    840
tgtggacagc agctgcacga gtctttgcgc ctgatccagg aagctggtcg gggagtagtg    900
gtgtacatgc gtgggcatga gggacgaggc attggtctgc tcgccaagct acgcgcctac    960
caactccagg atgaaggtgc cgacaccgtc gatgccaacc tcgcacttgg tcttccagcc   1020
gatgcccgcg aatttggcac cagcgcccag attctctacg acttgggtgt gcgctcgctc   1080
aacttgatca gcaacaaccc agccaagaag gtgggacttg aaggccacgg catttccatt   1140
gccagccgaa cccccatccc tgttgctgtt catgaagaca atgttcgata cctgaaaacc   1200
aagcgtgacc gcatgggaca tgacctccca gatgtcgcac tgtgggaaca agagcaccca   1260
gaaaactaa                                                             1269
```

<210> SEQ ID NO 37
<211> LENGTH: 422
<212> TYPE: PRT
<213> ORGANISM: Corynebacterium glutamicum

<400> SEQUENCE: 37

Val Ser Glu His Glu Gln Ala His Ser Gln Leu Asp Ser Val Glu Glu
1               5                   10                  15

Ala Ile Ala Asp Ile Ala Ala Gly Lys Ala Val Val Val Asp Asp
            20                  25                  30

Glu Asp Arg Glu Asn Glu Gly Asp Ile Ile Phe Ala Ala Glu Leu Ala
        35                  40                  45

Thr Pro Glu Leu Val Ala Phe Met Val Arg Tyr Ser Ser Gly Tyr Ile
    50                  55                  60

Cys Ala Pro Leu Thr Ala Lys Asp Ala Asp Arg Leu Asp Leu Pro Pro
65                  70                  75                  80

Met Thr Ala His Asn Gln Asp Ala Arg Gly Thr Ala Tyr Thr Val Thr
                85                  90                  95

Val Asp Ala Asn Thr Gly Thr Thr Gly Ile Ser Ala Thr Asp Arg Ala
            100                 105                 110

His Thr Leu Arg Leu Leu Ala Asp Pro Glu Ala Asp Arg Thr Asp Phe
        115                 120                 125

Thr Arg Pro Gly His Val Val Pro Leu Arg Ala Arg Glu Gly Gly Val
    130                 135                 140

Leu Val Arg Ala Gly His Thr Glu Ala Ala Val Asp Leu Ala Arg Ala
145                 150                 155                 160

Ala Gly Leu Arg Pro Ala Gly Val Ile Cys Glu Val Val Ser Glu Glu
                165                 170                 175

```
Asp Pro Thr Gly Met Ala Arg Val Pro Glu Leu Arg Arg Phe Cys Asp
            180                 185                 190
Glu His Asp Leu Lys Leu Ile Ser Ile Glu Gln Leu Ile Glu Trp Arg
        195                 200                 205
Arg Lys Asn Glu Ile Leu Val Glu Arg Gln Val Glu Thr Val Leu Pro
    210                 215                 220
Thr Asp Phe Gly Thr Phe Lys Ala Val Gly Tyr Arg Ser Ile Ile Asp
225                 230                 235                 240
Gly Thr Glu Leu Val Ala Ile Val Ala Gly Asp Val Ala Ser Asp Gly
                245                 250                 255
Gly Glu Asn Val Leu Val Arg Val His Ser Glu Cys Leu Thr Gly Asp
            260                 265                 270
Val Phe Gly Ser Arg Arg Cys Asp Cys Gly Gln Gln Leu His Glu Ser
        275                 280                 285
Leu Arg Leu Ile Gln Glu Ala Gly Arg Gly Val Val Val Tyr Met Arg
    290                 295                 300
Gly His Glu Gly Arg Gly Ile Gly Leu Leu Ala Lys Leu Arg Ala Tyr
305                 310                 315                 320
Gln Leu Gln Asp Glu Gly Ala Asp Thr Val Asp Ala Asn Leu Ala Leu
                325                 330                 335
Gly Leu Pro Ala Asp Ala Arg Glu Phe Gly Thr Ser Ala Gln Ile Leu
            340                 345                 350
Tyr Asp Leu Gly Val Arg Ser Leu Asn Leu Ile Ser Asn Asn Pro Ala
        355                 360                 365
Lys Lys Val Gly Leu Glu Gly His Gly Ile Ser Ile Ala Ser Arg Thr
    370                 375                 380
Pro Ile Pro Val Ala Val His Glu Asp Asn Val Arg Tyr Leu Lys Thr
385                 390                 395                 400
Lys Arg Asp Arg Met Gly His Asp Leu Pro Asp Val Ala Leu Trp Glu
                405                 410                 415
Gln Glu His Pro Glu Asn
            420

<210> SEQ ID NO 38
<211> LENGTH: 1197
<212> TYPE: DNA
<213> ORGANISM: Bacillus amyloliquefaciens

<400> SEQUENCE: 38
atgtttcatc cgatagaaga ggcattagaa gcgctgaaaa aggtgaagt catcatcgtt     60 gtcgatgatg aagacagaga aaacgaagga gatttcgtag cgctcgctga gcatgctacg    120
cctgaagtgg tgaattttat ggcgacccac gggagaggcc tgatctgcac gccgctttct    180
gaagacatcg ccggccggct ggatcttcat ccaatggtcg atcataatac agactcgcat    240
gagaccgcgt ttacagtcag cattgaccac aagctgacaa aaacgggaat cagcgctcag    300
gaacgttcct ttacgattca ggcgcttttg gacgaagaat ctgtgcctgg cgattttcag    360
cgtccgggtc atattttcc cttaatagca aaaaaggag gcgtcctgaa gcgggcgggc    420
cacacggaag cagccgttga cctggcaaaa gcatgcggtt tcaaggagc ggacgtcatt    480 tgtgaaatta tgaatgaaga cggcacaatg gcgagagtgc ctgagattag cgagattgcg    540
aaaagccacc agctgaaaat gattacgata aagacttaa tagaataccg ctacaacatt    600
acaacacttg tgaacagaga agttgacatt acgctgccga ctgacttcgg cacgttccgg    660
gtttacggat atacaaacga ggtggacgga aaagaacatc tcgcctttgt catgggcgat    720
```

```
gtcccgttta acagcggacc cgttcttgtc agagtgcact cagaatgcct gaccggcgat    780
gtgtttgcat cccaccgctg tgattgcggg cctcagcttc atgccgcgtt gcgccaaatt    840
gccgaagaag gccgcggcgt tctattgtat ttgcgtcagg aaggcagagg aatcggtctc    900
atcaataagc tgaaagcgta tcgattgcag gaacaaggt acgacacggt tgaagcgaac    960
gaagcgctcg gctttctgcc tgacttgcgc aactatggca tcggcgccca gattctccgc   1020
gatttagggg ttcagcatat gaaacttta accaataacc cccggaaaat cgccggcctt   1080
gaagggtacg gactaagcat ttcagatcgg gtgccgcttc aaatggaagc gagtgagcac   1140
aacaagcagt atttacaaac caaaatgaaa aaactcggac acttgcttca tttctaa     1197
```

<210> SEQ ID NO 39
<211> LENGTH: 398
<212> TYPE: PRT
<213> ORGANISM: Bacillus amyloliquefaciens

<400> SEQUENCE: 39

```
Met Phe His Pro Ile Glu Glu Ala Leu Glu Ala Leu Lys Lys Gly Glu
1               5                   10                  15

Val Ile Ile Val Val Asp Asp Glu Asp Arg Glu Asn Glu Gly Asp Phe
            20                  25                  30

Val Ala Leu Ala Glu His Ala Thr Pro Glu Val Val Asn Phe Met Ala
        35                  40                  45

Thr His Gly Arg Gly Leu Ile Cys Thr Pro Leu Ser Glu Asp Ile Ala
    50                  55                  60

Gly Arg Leu Asp Leu His Pro Met Val Asp His Asn Thr Asp Ser His
65                  70                  75                  80

Glu Thr Ala Phe Thr Val Ser Ile Asp His Lys Leu Thr Lys Thr Gly
                85                  90                  95

Ile Ser Ala Gln Glu Arg Ser Phe Thr Ile Gln Ala Leu Leu Asp Glu
            100                 105                 110

Glu Ser Val Pro Gly Asp Phe Gln Arg Pro Gly His Ile Phe Pro Leu
        115                 120                 125

Ile Ala Lys Lys Gly Gly Val Leu Lys Arg Ala Gly His Thr Glu Ala
    130                 135                 140

Ala Val Asp Leu Ala Lys Ala Cys Gly Ser Gln Gly Ala Asp Val Ile
145                 150                 155                 160

Cys Glu Ile Met Asn Glu Asp Gly Thr Met Ala Arg Val Pro Glu Ile
                165                 170                 175

Ser Glu Ile Ala Lys Ser His Gln Leu Lys Met Ile Thr Ile Lys Asp
            180                 185                 190

Leu Ile Glu Tyr Arg Tyr Asn Ile Thr Thr Leu Val Asn Arg Glu Val
        195                 200                 205

Asp Ile Thr Leu Pro Thr Asp Phe Gly Thr Phe Arg Val Tyr Gly Tyr
    210                 215                 220

Thr Asn Glu Val Asp Gly Lys Glu His Leu Ala Phe Val Met Gly Asp
225                 230                 235                 240

Val Pro Phe Asn Ser Gly Pro Val Leu Arg Val His Ser Glu Cys
                245                 250                 255

Leu Thr Gly Asp Val Phe Ala Ser His Arg Cys Asp Cys Gly Pro Gln
            260                 265                 270

Leu His Ala Ala Leu Arg Gln Ile Ala Glu Glu Gly Arg Gly Val Leu
        275                 280                 285

Leu Tyr Leu Arg Gln Glu Gly Arg Gly Ile Gly Leu Ile Asn Lys Leu
    290                 295                 300
```

```
Lys Ala Tyr Arg Leu Gln Glu Gln Gly Tyr Asp Thr Val Glu Ala Asn
305                 310                 315                 320

Glu Ala Leu Gly Phe Leu Pro Asp Leu Arg Asn Tyr Gly Ile Gly Ala
            325                 330                 335

Gln Ile Leu Arg Asp Leu Gly Val Gln His Met Lys Leu Leu Thr Asn
        340                 345                 350

Asn Pro Arg Lys Ile Ala Gly Leu Glu Gly Tyr Gly Leu Ser Ile Ser
    355                 360                 365

Asp Arg Val Pro Leu Gln Met Glu Ala Ser Glu His Asn Lys Gln Tyr
370                 375                 380

Leu Gln Thr Lys Met Lys Lys Leu Gly His Leu Leu His Phe
385                 390                 395

<210> SEQ ID NO 40
<211> LENGTH: 1194
<212> TYPE: DNA
<213> ORGANISM: Bacillus cereus

<400> SEQUENCE: 40
atgtttcatc gtattgaaga agctctagaa gatttaaaaa aaggtaaagt cgttatcgta      60
tgtgatgatg aaaaccgaga aaatgaaggc gatttattg  ctttagcaga gtacattaca     120
ccagaaacaa taattttat  gattacacat ggccgtggtc tcgtttgtgt accgattacg     180
gaaggatacg cagaacgtct acaattagaa ccaatggtat ctcataatac agattcacat     240
catactgcgt ttacagtgag cattgaccat gtctctacaa caacagggat tagcgctcac     300
gaacgtgcaa ctacgataca agaattgtta accccgcat  caaaaggtgc tgatttcaat     360
cgacctggac atatctttcc attaattgcg aaagaaggcg tgtcctgcg  tcgtgcaggt     420 catacagaag ctgctgttga tttagcaaag ctatgcggtg ccgaaccagc tggagttatt     480
tgcgagatta taaatgagga cggcacgatg gcacgtgtac ctgatttaat agaatgcgca     540
aaacaatttg atataaaaat gattacaata gaagatttaa ttgcttaccg ccgccatcat     600
gaaacacttg tgacgagaga agcggaaatt acattaccta cagatttcgg tactttccac     660
gcaattggct attctaactc attagatacg aaagaacata tcgcacttgt aaaaggtgat     720
atttcaacag gtgaaccggt acttgtacgt gttcattctg aatgcttaac aggagatgta     780
ttcggttcac atcgctgcga ttgcggacca caactccatg cagcacttgc tcaaattgag     840
cgtgaaggaa aagtgttct  tctttatatg aggcaagaag aagaggcat  tgggcttctt     900 aataagcttc gtgcttataa attacaagaa gaaggattcg atactgtaga agcaaatgaa     960
aaactcggct ccctgctga  tcttcgtgat tacggtatcg gtgctcaaat attaaaagat    1020
ttaggtttac agagtttacg attattaacg aataacccaa gaaaaattgc tggcttacaa    1080
ggttacgatt tagaagtagt cgagcgtgta ccgttgcaaa tgccagcaaa agaagagaat    1140
aaatcgtatt tacaaacgaa agtaaacaaa ttaggacact tactaaactt ataa           1194

<210> SEQ ID NO 41
<211> LENGTH: 397
<212> TYPE: PRT
<213> ORGANISM: Bacillus cereus

<400> SEQUENCE: 41

Met Phe His Arg Ile Glu Glu Ala Leu Glu Asp Leu Lys Lys Gly Lys
1               5                   10                  15

Val Val Ile Val Cys Asp Asp Glu Asn Arg Glu Asn Glu Gly Asp Phe

```
Ile Ala Leu Ala Glu Tyr Ile Thr Pro Glu Thr Ile Asn Phe Met Ile
         35                  40                  45

Thr His Gly Arg Gly Leu Val Cys Val Pro Ile Thr Glu Gly Tyr Ala
 50                  55                  60

Glu Arg Leu Gln Leu Glu Pro Met Val Ser His Asn Thr Asp Ser His
 65                  70                  75                  80

His Thr Ala Phe Thr Val Ser Ile Asp His Val Ser Thr Thr Thr Gly
             85                  90                  95

Ile Ser Ala His Glu Arg Ala Thr Thr Ile Gln Glu Leu Leu Asn Pro
            100                 105                 110

Ala Ser Lys Gly Ala Asp Phe Asn Arg Pro Gly His Ile Phe Pro Leu
        115                 120                 125

Ile Ala Lys Glu Gly Gly Val Leu Arg Arg Ala Gly His Thr Glu Ala
        130                 135                 140

Ala Val Asp Leu Ala Lys Leu Cys Gly Ala Glu Pro Ala Gly Val Ile
145                 150                 155                 160

Cys Glu Ile Ile Asn Glu Asp Gly Thr Met Ala Arg Val Pro Asp Leu
                165                 170                 175

Ile Glu Cys Ala Lys Gln Phe Asp Ile Lys Met Ile Thr Ile Glu Asp
            180                 185                 190

Leu Ile Ala Tyr Arg Arg His His Glu Thr Leu Val Thr Arg Glu Ala
        195                 200                 205

Glu Ile Thr Leu Pro Thr Asp Phe Gly Thr Phe His Ala Ile Gly Tyr
    210                 215                 220

Ser Asn Ser Leu Asp Thr Lys Glu His Ile Ala Leu Val Lys Gly Asp
225                 230                 235                 240

Ile Ser Thr Gly Glu Pro Val Leu Val Arg Val His Ser Glu Cys Leu
                245                 250                 255

Thr Gly Asp Val Phe Gly Ser His Arg Cys Asp Cys Gly Pro Gln Leu
            260                 265                 270

His Ala Ala Leu Ala Gln Ile Glu Arg Glu Gly Lys Gly Val Leu Leu
        275                 280                 285

Tyr Met Arg Gln Glu Gly Arg Gly Ile Gly Leu Leu Asn Lys Leu Arg
    290                 295                 300

Ala Tyr Lys Leu Gln Glu Glu Gly Phe Asp Thr Val Glu Ala Asn Glu
305                 310                 315                 320

Lys Leu Gly Phe Pro Ala Asp Leu Arg Asp Tyr Gly Ile Gly Ala Gln
                325                 330                 335

Ile Leu Lys Asp Leu Gly Leu Gln Ser Leu Arg Leu Leu Thr Asn Asn
            340                 345                 350

Pro Arg Lys Ile Ala Gly Leu Gln Gly Tyr Asp Leu Glu Val Val Glu
        355                 360                 365

Arg Val Pro Leu Gln Met Pro Ala Lys Glu Glu Asn Lys Ser Tyr Leu
    370                 375                 380

Gln Thr Lys Val Asn Lys Leu Gly His Leu Leu Asn Leu
385                 390                 395

<210> SEQ ID NO 42
<211> LENGTH: 1215
<212> TYPE: DNA
<213> ORGANISM: Bacillus halodurans

<400> SEQUENCE: 42
atggacaaaa agctatttga tccgattgaa gaagcaatat atgaattaat gcaaggtcga      60
gtcgtgatcg tttgtgatga tgaggatcgg gaaaacgaag gggattttgt agcccttgct     120
```

```
gaaaaagcaa caccagaagt gattaacttc atgatcacgc atggccgtgg tctcgtttgc    180
acgccaatca cggaagagcg ggcaaaggaa ttagatcttg tccccatggt ggaccataat    240
accgatcccc atggtacggc gtttaccgtc agcattgatc atcaaatgac gaccacagga    300
atttctgccc atgaacgggc tatgacgatt caggcgttaa ttgataagaa aacgaaaaag    360
caccacttca aacgaccagg tcacattttc ccctaatag cgaaaaacgg aggagtactc     420
cgacgggccg gtcatacaga agcggccgtt gatctagctc gtttgtcagg cgctgagccg    480
gcaggggtta tttgtgaaat cattaaagaa gatggttcaa tggcacgagt tcctgatttg    540
cgaaaaatcg ccgatcagtt tgaactgaag atgatcacaa ttaaagattt aatcgaatat    600
cgtcaccgta agacaagct tgtcaagcgt gaagtagata tttccttacc gacggatttc    660
ggctcattcc gtgcaatcgg ttatacagat gtcattgatg aaaagagag tgtcgcttta    720
gtgaaaggac agattgttga aggtgaacca acactcgttc gtgttcactc cgaatgttta    780
acaggtgatg tgttcggttc tcaccgttgc gattgtggcc cacaactcca ggcagctctc    840
acacaaatcg agcaacaagg caaagggata ctcctttata tgcgtcaaga gggtcgtggt    900
atcggtctca tgaataagtt gaaggcatac aagcttcaag aagaaggcta tgatactgta    960
gaagcaaatg agaaattagg cttccctgct gatcttcggg actatggaat gggcgcgcaa   1020
attttacgcg acttaggtgt gtcaaaaatg cgcctcctta caacaatcc gcgaaaaatt   1080
acgggcttga aagggtatgg ccttgaagtg gttgaacggg tgccgctcca attacctcat   1140
aacaaagata tgagcgcta tttgaaaaca aagcacgaaa agttaggaca tctgctaaat   1200
tttactcatt cgtaa                                                    1215
```

<210> SEQ ID NO 43
<211> LENGTH: 404
<212> TYPE: PRT
<213> ORGANISM: Bacillus halodurans

<400> SEQUENCE: 43

```
Met Asp Lys Lys Leu Phe Asp Pro Ile Glu Glu Ala Ile Tyr Glu Leu
1               5                   10                  15

Met Gln Gly Arg Val Val Ile Val Cys Asp Asp Glu Asp Arg Glu Asn
            20                  25                  30

Glu Gly Asp Phe Val Ala Leu Ala Glu Lys Ala Thr Pro Glu Val Ile
        35                  40                  45

Asn Phe Met Ile Thr His Gly Arg Gly Leu Val Cys Thr Pro Ile Thr
    50                  55                  60

Glu Glu Arg Ala Lys Glu Leu Asp Leu Val Pro Met Val Asp His Asn
65                  70                  75                  80

Thr Asp Pro His Gly Thr Ala Phe Thr Val Ser Ile Asp His Gln Met
                85                  90                  95

Thr Thr Thr Gly Ile Ser Ala His Glu Arg Ala Met Thr Ile Gln Ala
            100                 105                 110

Leu Ile Asp Lys Lys Thr Lys Lys His His Phe Lys Arg Pro Gly His
        115                 120                 125

Ile Phe Pro Leu Ile Ala Lys Asn Gly Gly Val Leu Arg Arg Ala Gly
    130                 135                 140

His Thr Glu Ala Ala Val Asp Leu Ala Arg Leu Ser Gly Ala Glu Pro
145                 150                 155                 160

Ala Gly Val Ile Cys Glu Ile Ile Lys Glu Asp Gly Ser Met Ala Arg
                165                 170                 175
```

-continued

```
Val Pro Asp Leu Arg Lys Ile Ala Asp Gln Phe Glu Leu Lys Met Ile
            180                 185                 190

Thr Ile Lys Asp Leu Ile Glu Tyr Arg His Arg Lys Asp Lys Leu Val
        195                 200                 205

Lys Arg Glu Val Asp Ile Ser Leu Pro Thr Asp Phe Gly Ser Phe Arg
    210                 215                 220

Ala Ile Gly Tyr Thr Asp Val Ile Asp Gly Lys Glu Ser Val Ala Leu
225                 230                 235                 240

Val Lys Gly Gln Ile Val Glu Gly Glu Pro Thr Leu Val Arg Val His
                245                 250                 255

Ser Glu Cys Leu Thr Gly Asp Val Phe Gly Ser His Arg Cys Asp Cys
            260                 265                 270

Gly Pro Gln Leu Gln Ala Ala Leu Thr Gln Ile Glu Gln Gln Gly Lys
            275                 280                 285

Gly Ile Leu Leu Tyr Met Arg Gln Glu Gly Arg Gly Ile Gly Leu Met
        290                 295                 300

Asn Lys Leu Lys Ala Tyr Lys Leu Gln Glu Glu Gly Tyr Asp Thr Val
305                 310                 315                 320

Glu Ala Asn Glu Lys Leu Gly Phe Pro Ala Asp Leu Arg Asp Tyr Gly
            325                 330                 335

Met Gly Ala Gln Ile Leu Arg Asp Leu Gly Val Ser Lys Met Arg Leu
            340                 345                 350

Leu Thr Asn Asn Pro Arg Lys Ile Thr Gly Leu Lys Gly Tyr Gly Leu
        355                 360                 365

Glu Val Val Glu Arg Val Pro Leu Gln Leu Pro His Asn Lys Asp Asn
    370                 375                 380

Glu Arg Tyr Leu Lys Thr Lys His Glu Lys Leu Gly His Leu Leu Asn
385                 390                 395                 400

Phe Thr His Ser
```

MUTANT GTP CYCLOHYDROLASE II ENZYMES

This application is the National Stage of International Application No. PCT/EP2005/007320, filed Jul. 7, 2005.

The present invention provides modified enzymes with higher GTP cyclohydrolase II activity than the respective wild-type enzymes. The modified enzymes and polynucleotides encoding the same can be used for the production of riboflavin, riboflavin precursors, flavin mononucleotide (FMN), flavin adenine dinucleotide (FAD), and derivatives thereof.

Riboflavin (vitamin B2) is synthesized by all plants and many microorganisms but is not produced by higher animals. Because it is a precursor to coenzymes such as flavin adenine dinucleotide and flavin mononucleotide that are required in the enzymatic oxidation of carbohydrates, riboflavin is essential to basic metabolism. In higher animals, insufficient riboflavin can cause loss of hair, inflammation of the skin, vision deterioration, and growth failure.

Engineering of riboflavin production strains with increased rates and yields of riboflavin has been achieved in the past in a number of different ways. For instance, (1) classical mutagenesis was used to create variants with random mutations in the genome of the organism of choice, followed by selection for higher resistance to purine analogs and/or by screening for increased production of riboflavin. (2) Alternatively, the terminal enzymes of riboflavin biosynthesis, i.e., the enzymes catalyzing the conversion of guanosine triphosphate (GTP) and ribulose-5-phosphate to riboflavin, were overexpressed, resulting also in a higher flux towards the target product. However, in this latter approach, strong overexpression of the riboflavin biosynthesis proteins imposes an additional metabolic burden on the host cells which may, in turn, induce stress response reactions and other undesirable negative effects on the cells' physiology.

The enzymes required catalyzing the biosynthesis of riboflavin from guanosine triphosphate (GTP) and ribulose-5-phosphate are encoded by four genes (ribG, ribB, ribA, and ribH) in *B. subtilis*. These genes are located in an operon, the gene order of which differs from the order of the enzymatic reactions catalyzed by the enzymes. For example, GTP cyclohydrolase II, which catalyzes the first step in riboflavin biosynthesis, is encoded by the third gene in the operon, ribA. The ribA gene also encodes a second enzymatic activity, i.e., 3,4-dihydroxy-2-butanone 4-phosphate synthase (DHBPS), which catalyzes the conversion of ribulose-5-phosphate to the four-carbon unit 3,4-dihydroxy-2-butanone 4-phosphate (DHBP). Deaminase and reductase are encoded by the first gene of the operon, ribG. The penultimate step in riboflavin biosynthesis is catalyzed by lumazine synthase, the product of the last rib gene, ribH. Riboflavin synthase, which controls the last step of the pathway, is encoded by the second gene of the operon, ribB. The function of the gene located at the 3' end of the rib operon is, at present, unclear; however, its gene product is not required for riboflavin synthesis.

Transcription of the riboflavin operon from the ribP1 promoter is controlled by an attenuation mechanism involving a regulatory leader region located between ribP1 and ribG. The ribO mutations within this leader region result in deregulated expression of the riboflavin operon. Deregulated expression is also observed in strains containing missense mutations in the ribC gene. The ribC gene has been shown to encode the flavin kinase/FAD synthase of *B. subtilis* (Mack, M., et al., J. Bacteriol., 180:950-955, 1998). Deregulating mutations reduce the flavokinase activity of the ribC gene product resulting in reduced intracellular concentrations of flavin mononucleotide (FMN), the effector molecule of the riboflavin regulatory system.

Recently, *Bacillus subtilis* was genetically engineered to produce high yields of riboflavin during a short fermentation cycle (U.S. Pat. No. 5,837,528). This approach combined classical genetic mutant selection and fermentation improvement with genetic engineering of the riboflavin biosynthetic genes by deregulating and increasing the level of gene expression. In this system, the expression of the rib genes was increased by mutating the flavokinase encoding ribC gene, by linking the rib genes to strong, constitutive promoters, and by increasing the copy number of the rib genes.

As already discussed above, overexpression of the rib genes poses an additional burden on the production strains which may, potentially, have a negative impact on the production of riboflavin precursors, riboflavin, FMN, FAD, or their derivatives. In order to circumvent this shortcoming, it is a subject of the present invention to describe GTP cyclohydrolase II mutants with increased specific activity. Use of such mutant enzymes in production strains, either alone or combined with improved mutants of the other Rib proteins, will allow higher flux rates with less or no additional burden on the cells' metabolism.

As used herein, the term "GTP cyclohydrolase II" may include any enzyme that is capable of catalyzing the conversion of GTP to 2,5-diamino-6-ribosylamino-4 (3H)-pyrimidinone-5'-phosphate (DRAPP). It is irrelevant whether this enzyme is capable of catalyzing further reactions, as for example the conversion of ribulose-5-phosphate to DHBP. A "GTP cyclohydrolase II" may be homologous to one or more of the enzymes the amino acid sequences of which are shown in Table 4. "Homologous" refers to a GTP cyclohydrolase II that is at least about 50% identical, preferably at least about 60% identical, more preferably at least about 70% identical, even more preferably at least about 80% identical, even more preferably at least about 85% identical, even more preferably at least about 90% or 95% identical, and most preferably at least about 98% identical to one or more of the amino acid sequences as shown in Table 4.

The term "% identity", as known in the art, means the degree of relatedness between polypeptide or polynucleotide sequences, as the case may be, as determined by the match between strings of such sequences. "Identity" can be readily determined by known methods, e.g., with the program BESTFIT (GCG Wisconsin Package, version 10.2, Accelrys Inc., 9685 Scranton Road, San Diego, Calif. 92121-3752, USA) using the following parameters: gap creation penalty 8, gap extension penalty 2 (default parameters).

"Wild-type enzyme" or "wild-type GTP cyclohydrolase II" may include any GTP cyclohydrolase II homologous to any one of the enzymes shown in Table 4 that is used as starting point for designing mutants with increased activity according to the present invention. "Wild-type" in the context of the present invention may include both GTP cyclohydrolase II sequences derivable from nature as well as variants of synthetic GTP cyclohydrolase II enzymes (as long as they are homologous to any one of the sequences shown in Table 4), if they can be made more active by any of the teachings of the present invention. The terms "wild-type GTP cyclohydrolase II" and "non-modified GTP cyclohydrolase II" are used interchangeably herein.

A "mutant", "mutant enzyme", or "mutant GTP cyclohydrolase II" may include any variant derivable from a given wild-type enzyme/GTP cyclohydrolase II (according to the above definition) according to the teachings of the present invention and being more active than the respective wild-type enzyme. For the scope of the present invention, it is not relevant how the mutant(s) are obtained; such mutants may be obtained, e.g., by site-directed mutagenesis, saturation mutagenesis, random mutagenesis/directed evolution, chemical or UV mutagenesis of entire cells/organisms, and other methods which are known in the art. These mutants may also be generated, e.g., by designing synthetic genes, and/or produced by in vitro (cell-free) translation. For testing of specific activity, mutants may be (over-) expressed by methods known to those skilled in the art. The terms "mutant GTP cyclohydrolase II" and "modified GTP cyclohydrolase II" are used interchangeably herein. This also applies to the terms "mutant enzyme" and "modified enzyme".

"Riboflavin precursor" and "derivatives of riboflavin, FMN or FAD" in the context of this patent application may include any and all metabolite(s) requiring GTP cyclohydrolase II as an intermediate enzyme in their (bio-) synthesis. In the context of this patent application, it is irrelevant whether such (bio-) synthesis pathways are natural or non-natural (i.e., pathways not occurring in nature, but engineered biotechnologically). Preferably, the synthesis pathways are biochemical in nature. Riboflavin precursors and derivatives of riboflavin, FMN or FAD include but are not limited to: DRAPP; 5-amino-6-ribosylamino-2,4 (1H,3H)-pyrimidinedione-5'-phosphate; 2,5-diamino-6-ribitylamino-4 (3H)-pyrimidinone-5'-phosphate; 5-amnino-6-ribitylamino-2,4 (1H,3H)-pyrimidinedione-5'-phosphate; 5-amino-6-ribitylamino-2,4 (1H,3H)-pyrimidinedione; 6,7-dimethyl-8-ribityllumazine (DMRL); and flavoproteins. The term "riboflavin" also includes derivatives of riboflavin, such as e.g. riboflavin-5-phosphate and salts thereof, such as e.g. sodium riboflavin-5-phosphate.

It is in general an object of the present invention to provide an enzyme having GTP cyclohydrolase II activity, said enzyme being modified in a way that its catalytic properties are more favorable (i.e., showing higher specific activity) than those of the non-modified GTP cyclohydrolase II enzymes.

The invention relates to a modified GTP cyclohydrolase II which exhibits higher (specific) activity in comparison to the corresponding non-modified GTP cyclohydrolase II wherein (i) the amino acid sequence of the modified GTP cyclohydrolase II contains at least one mutation when compared with the amino acid sequence of the corresponding non-modified GTP cyclohydrolase II, and (ii) the at least one mutation is at one or more amino acid positions selected from the group consisting of amino acid positions corresponding to positions 261, 270, 276, 279, 308 and 347 of the amino acid sequence of *Bacillus subtilis* GTP cyclohydrolase II as shown in SEQ ID NO:2.

Thus, it is an object of the present invention to provide a modified GTP cyclohydrolase II, wherein (i) the specific activity of the modified enzyme is increased in comparison to the corresponding non-modified enzyme, and (ii) the amino acid sequence of the modified enzyme comprises one or more mutation(s) including 1, 2, 3, 4, 5, or 6 mutation(s) on amino acid position(s) corresponding to positions 261, 270, 276, 279, 308 and/or 347 of SEQ ID NO:2.

The term "at least one mutation" means one or more mutation on a position as defined above leading to a modified GTP cyclohydrolase II having an increased specific activity compared to the non-modified enzyme. A modified enzyme as described above may consists of only 1, 2, 3, 4, 5 or 6 mutation(s) on a position as defined above leading to an increased specific activity compared to the non-modified enzyme, but may also include further amino acid mutations on other positions, as long as the resulting modified enzyme has an increased specific activity. Thus, the modified enzyme comprises one or more mutation(s) including 1, 2, 3, 4, 5, or 6 mutation(s) on amino acid position(s) corresponding to positions 261, 270, 276, 279, 308 and/or 347 of the amino acid sequence of *Bacillus subtilis* GTP cyclohydrolase II as shown in SEQ ID NO:2. Examples of such mutations on positions other than the ones defined above are amino acid mutation(s) on a position corresponding to amino acid position 196, 282, and/or 325 of SEQ ID NO:2.

As used herein, the term "specific activity" denotes the reaction rate of the wild-type and mutant GTP cyclohydrolase II enzymes under properly defined reaction conditions as described e.g. in Ritz et al. (J. Biol. Chem. 276, 22273-22277, 2001), Koh et al. (Mol. Gen. Genet. 251, 591-598, 1996), or Schramek et al. (J. Biol. Chem. 276, 44157-44162, 2001) or as described in detail in Example 2. The "specific activity" defines the amount of substrate consumed and/or product produced in a given time period and per defined amount of protein at a defined temperature. Typically, "specific activity" is expressed in µmol substrate consumed or product formed per min per mg of protein. Typically, µmol/min is abbreviated by U (=unit). Therefore, the unit definitions for specific activity of µmol/min/(mg of protein) or U/(mg of protein) are used interchangeably throughout this document. It is understood that in the context of the present invention, specific activity must be compared on the basis of a similar, or preferably identical, length of the polypeptide chain. The invention shall not be circumvented by increasing the size of a given wild-type enzyme through, e.g., formation of a fusion protein, thereby reducing the apparent specific activity of the overall enzyme.

According to the present invention the modified GTP cyclohydrolase II exhibits a specific activity that is higher than that of the corresponding non-modified enzyme. Preferably, the specific activity of the modified GTP cyclohydrolase II of the invention is increased by at least about 5, 10, 25, 40, 60, 70, 80, 85, 90%, more preferably at least about 70% in comparison to the corresponding non-modified GTP cyclohydrolase II (for measurement of specific activity, see below). Preferably, increases in specific activity refer to the experimental conditions described in Example 1 of this application. Approx. 0.004-0.02 U/ml (corresponding to approx. 40 µg/ml of *Bacillus subtilis* GTP cyclohydrolase II or 20 µg/ml for the best mutants described here), preferably approx. 0.004 U/ml of GTP cyclohydrolase II activity, were present in the assay mixture, and the reaction was carried out at 37° C.

The amino acid sequence of the modified GTP cyclohydrolase II of the invention contains at least one mutation as defined above when compared with the amino acid sequence of the corresponding non-modified GTP cyclohydrolase II. Said mutation may be one or more addition, deletion and/or substitution, preferably one or more amino acid substitution wherein a given amino acid present in the amino acid sequence of the non-modified GTP cyclohydrolase II is replaced with a different amino acid in the amino acid sequence of the modified GTP cyclohydrolase II of the invention. The amino acid sequence of the modified GTP cyclohydrolase II may contain at least one amino acid substitution when compared with the amino acid sequence of the corresponding non-modified GTP cyclohydrolase II, i.e. may comprise one or more mutation(s) including 1, 2, 3, 4, 5, or 6 amino acid substitution(s) on amino acid position(s) corresponding to positions 261, 270, 276, 279, 308 and/or 347 of SEQ ID NO:2, preferably 2, 3, 4 or 5 amino acid substitutions. Thus, the modified enzyme preferably contains at least 2, at least 3, at least 4 or at least 5 substitutions when compared with the amino acid sequence of the corresponding non-modified GTP cyclohydrolase II.

In one embodiment, a modified GTP cyclohydrolase II obtainable from *Bacillus*, preferably *Bacillus subtilis*, is provided, wherein (i) the specific activity of the modified enzyme is increased in comparison to the corresponding non-modified enzyme, and (ii) the amino acid sequence of the modified enzyme comprises one or more mutation(s) including 1, 2, 3, 4, 5, or 6 mutation(s) on amino acid position(s) corresponding to positions 261, 270, 276, 279, 308 and/or 347 of SEQ ID NO:2.

In one embodiment the non-modified enzyme corresponds to *Bacillus subtilis* GTP cyclohydrolase II as shown in SEQ ID NO:2. Thus, the modified enzyme having an increased specific activity in comparison to the wild type enzyme comprises one or more mutation(s) including 1, 2, 3, 4, 5, or 6 mutation(s) on amino acid position(s) corresponding to positions 261, 270, 276, 279, 308 and/or 347 of SEQ ID NO:2. In a further embodiment the modified enzyme having increased specific activity as defined above contains amino acid mutation(s) beside the amino acid positions as above, said further mutation(s) being on a position selected from the group consisting of position 196, 282, 235, and any combination thereof, preferably amino acid substitutions, more preferably the substitutions are Y196C (replacement of tyrosine by cysteine), A282T (replacement of alanine by threonine) or F325Y (replacement of phenylalanine by tyrosine).

A non-modified GTP cyclohydrolase II may be any GTP cyclohydrolase II for which increasing the specific activity is desirable. Non-modified GTP cyclohydrolase II enzymes include but are not limited to GTP cyclohydrolase II enzymes derivable from nature, such as enzymes of eukaryotic or prokaryotic origin, preferably fugal or bacterial origin. More preferably the non-modified enzyme is selected from the ones shown in Table 4 or which is homologous to any of the amino acid sequences as shown in Table 4, in particular selected from the group consisting of *Ashbya, Saccharomyces, Eremothecium, Candida, Neurospora, Schizosaccharomyces, Archeoglobus, Streptomyces, Helicobacter, Escherichia, Corynebacterium, Thermotoga, Arabidopsis, Lycopersicum, Oryza, Alcaligenes, Pseudomonas, Dinococcus, Lactobacillus, Photobacterium* and *Bacillus* and preferably selected from the group consisting of *Candida guilliermondii, Ashbya gossypii (Eremothecium ashbyii)* (SEQ ID NO:33), *Saccharomyces cerevisiae, Neurospora crassa, Schizosaccharomyces pombe, Archeoglobus fulgidus, Streptomyces coelicolor, Helicobacter pylori* J99, *Escherichia coli* (SEQ ID NO:35), *Corynebacterium glutamicum* (SEQ ID NO:37), *Bacillus amyloliquefaciens* (SEQ ID NO:39), *Bacillus cereus* (SEQ ID NO:41), *Bacillus halodurans* (SEQ ID NO:43), *Thermotoga maritima, Arabidopsis thaliana, Lycopersicum exculentum, Oryza sativum, Alcaligenes eutrophus, Pseudomonas putida* strain KT2440, *Corynebacterium efficiens, Deinococcus radiodurans, Lactobacillus plantarum, Photobacterium phosphoreum, Pseudomonas putida* strain KT2440 (second gene) and *Bacillus subtilis* (SEQ ID NO:2). Most preferably the non-modified enzyme is obtainable from *Bacillus subtilis*.

The modified GTP cyclohydrolase II of the invention may be obtained by mutating the corresponding non-modified GTP cyclohydrolase II. In one embodiment, the non-modified enzyme corresponds to the *B. subtilis* GTP cyclohydrolase II shown in SEQ ID NO:2 and the modified enzyme comprises one or more amino acid mutation(s) including 1, 2, 3, 4, 5, or 6 mutation(s) on amino acid position(s) 261, 270, 276, 279, 308 and/or 347 of SEQ ID NO:2, wherein the specific activity of said modified enzyme is increased compared to the non-modified enzyme.

Preferably, the at least one mutation is at one or more amino acid positions selected from the group consisting of amino acid positions corresponding to positions 261, 279, 308 and 347 of the amino acid sequence of *Bacillus subtilis* GTP cyclohydrolase II as shown in SEQ ID NO: 2. Thus, in one embodiment the modified GTP cyclohydrolase II comprises one or more mutation(s) including 1, 2, 3 or 4 mutation(s) on amino acid position(s) corresponding to positions 261, 279, 308, and/or 347 of SEQ ID NO:2. In a preferred embodiment, the modified enzyme is obtainable from *B. subtilis* and comprises mutated amino acid positions 261, 279, 308, and/or 347 as shown in SEQ ID NO:2, corresponding to amino acids V261, Q279, K308, and M374, respectively.

In another preferred embodiment the at least one mutation is at one or more amino acid positions selected from the group consisting of amino acid positions corresponding to positions 270, 279, 308 and 347 of the amino acid sequence of *Bacillus subtilis* GTP cyclohydrolase II as shown in SEQ ID NO: 2. Thus, in one embodiment the modified GTP cyclohydrolase II comprises one or more mutation(s) including 1, 2, 3 or 4 mutation(s) on amino acid position(s) corresponding to positions 270, 279, 308, and/or 347 of SEQ ID NO:2. Preferably, the modified enzyme is obtainable from *B. subtilis* and comprises mutated amino acid positions 270, 279, 308, and/or 347 as shown in SEQ ID NO:2, corresponding to amino acids G270, Q279, K308, and M374, respectively.

In a further preferred embodiment the at least one mutation is at one ore more amino acid positions selected from the group consisting of amino acid positions corresponding to positions 276, 279, 308 and 347 of the amino acid sequence of *Bacillus subtilis* GTP cyclohydrolase II as shown in SEQ ID NO: 2. Thus, in a further embodiment the modified GTP cyclohydrolase II comprises one or more mutation(s) including 1, 2, 3 or 4 mutation(s) on amino acid position(s) corresponding to positions 276, 279, 308, and/or 347 of the amino acid sequence of *Bacillus subtilis* GTP cyclohydrolase II as shown in SEQ ID NO:2. Preferably, the modified enzyme is obtainable from *B. subtilis* and comprises mutated amino acid positions 276, 279, 308, and/or 347 as shown in SEQ ID NO:2, corresponding to amino acids A276, Q279, K308, and M374, respectively.

Preferably, the one or more amino acid mutation(s) of the modified GTP cyclohydrolase II is one or more amino acid substitution(s).

A modified GTP cyclohydrolase II may comprise one or more mutation(s) including only one mutation on an amino acid position as defined above, such mutation, particularly an amino acid substitution, may include one mutation on an amino acid position corresponding to position 261, 270, 276, 279, 308, or 347 of the amino acid sequence of *Bacillus subtilis* GTP cyclohydrolase II as shown in SEQ ID NO:2. The amino acid present in the non-modified GTP cyclohydrolase II corresponding to position 261 may be valine, the amino acid present in the non-modified GTP cyclohydrolase II corresponding to position 270 may be glycine, the amino acid present in the non-modified GTP cyclohydrolase II corresponding to position 276 may be alanine, the amino acid present in the non-modified GTP cyclohydrolase II corresponding to position 279 may be glutamine, the amino acid present in the non-modified GTP cyclohydrolase II corresponding to position 308 may be lysine, and the amino acid present in the non-modified GTP cyclohydrolase II corresponding to position 347 may be methionine.

The amino acid in the sequence of the non-modified GTP cyclohydrolase II maybe changed such that the amino acid corresponding to position 261 may be changed to alanine (e.g. V261A), the amino acid corresponding to position 270 may be changed to alanine or arginine (e.g. G270A and G270R), the amino acid corresponding to position 276 may be changed to threonine (e.g. A276T), the amino acid corresponding to position 279 may be changed to arginine (e.g. Q279A), the amino acid corresponding to position 308 may be changed to arginine (e.g. K308R), and the amino acid corresponding to position 347 may be changed to isoleucine (e.g. M374I). In one embodiment, the modified enzyme is obtainable from *B. subtilis* comprising an amino acid substitution in a position of SEQ ID NO:2 which is selected from the group consisting of position 261, 270, 276, 279, 308, and 347. Preferably, the substitution is V261A, G270A, G270R, A276T, Q279R, K308R or M347I.

A modified GTP cyclohydrolase II may comprise one or more mutation(s) including two mutations on amino acid positions as defined above, such mutations, particularly amino acid substitutions, may include mutations on amino acid positions corresponding to two of the positions as defined above, e.g. combinations of positions corresponding to positions 261/270, 261/276, 261/279, 261/308, 261/347, 270/276, 270/279, 270/308, 270/347, 276/279, 276/308, 276/347, 279/308, 279/347, or 308/347 as shown in SEQ ID NO:2. Preferred are amino acid substitutions such as V261A/A276T, V261A/Q279R, V261A/K308R, V261A/M347I, G270A/Q279R, G270A/K308R, G270A/M347I, A276T/Q279R, A276T/K308R, or A276T/M347I, wherein the positions correspond to the amino acid positions of SEQ ID NO:2. In one embodiment, such preferred substitutions are comprised in a modified GTP cyclohydrolase II obtainable from *B. subtilis* wherein the non-modified enzyme corresponds to SEQ ID NO:2. Preferably, the modified *B. subtilis* GTP cyclohydrolase II as of SEQ ID NO:2 comprises substitutions V261A/A276T or A276T/M347I.

A modified GTP cyclohydrolase II may comprise one or more mutation(s) including three mutations on amino acid positions as defined above, such mutations, particularly amino acid substitutions, may include mutations on amino acid positions corresponding to three of the positions as defined above, in particular combinations of positions corresponding to positions 261/279/308, 261/279/347, 261/308/347, 270/279/308, 270/279/347, 270/308/347, 276/279/308, 276/308/347, or 276/279/347 as shown in SEQ ID NO:2. Preferred are amino acid substitutions such as V261A/Q279R/K308R, V261A/K308R/M347I, V261A/Q279R/M347I, G270A/Q279R/K308R, G270A/K308R/M347I, G270A/Q279R/M347I, A276T/Q279R/K308R, A276T/K308R/M347I, or A276T/Q279R/M347I, wherein the positions correspond to the amino acid positions of SEQ ID NO:2. In one embodiment, such preferred substitutions are comprised in a modified GTP cyclohydrolase II obtainable from *B. subtilis* wherein the non-modified enzyme corresponds to SEQ ID NO:2. Preferably, the modified *B. subtilis* GTP cyclohydrolase II as of SEQ ID NO:2 comprises substitutions A276T/Q279R/M347I.

A modified GTP cyclohydrolase II may comprise one or more mutation(s) including four mutations on amino acid positions as defined above, such mutations, particularly amino acid substitutions, may include mutations in amino acid positions corresponding to four of the positions as defined above, in particular combinations of positions corresponding to positions 261/279/308/347, 270/279/308/347, or 276/279/308/347 as shown in SEQ ID NO:2. Preferred are amino acid substitutions such as V261A/Q279R/K308R/M347I, G270A/Q279R/K308R/M347I or A276T/Q279R/K308R/M347I, wherein the positions correspond to the amino acid positions of SEQ ID NO:2. In one embodiment, such preferred substitutions are comprised in a modified GTP cyclohydrolase II obtainable from *B. subtilis* wherein the non-modified enzyme corresponds to SEQ ID NO:2. Preferably, the modified *B. subtilis* GTP cyclohydrolase II as of SEQ ID NO:2 comprises substitutions A276T/Q279R/K308R/M347I.

Most preferred are the combinations of mutations disclosed in Table 1 or 2 (see infra). The amino acid positions identified in these examples may be transferred to GTP cyclohydrolase II enzymes of different origin, as e.g. shown in Table 4.

The modified GTP cyclohydrolase II of the invention may comprise foreign amino acids, preferably at its N- or C-terminus. "Foreign amino acids" mean amino acids which are not present in a native (occurring in nature) GTP cyclohydrolase II, preferably a stretch of at least about 3, at least about 5 or at least about 7 contiguous amino acids which are not present in a native GTP cyclohydrolase II. Preferred stretches of foreign amino acids include but are not limited to "tags" that facilitate purification of the recombinantly produced modified GTP cyclohydrolase II. Examples of such tags include but are not limited to a "His$_6$" tag, a FLAG tag, a myc tag, and the like. For calculation of specific activity, the values need to be corrected for these additional amino acids (see also above).

In another embodiment the modified GTP cyclohydrolase II may contain one or more, e.g. two, deletions when compared with the amino acid sequence of the corresponding non-modified GTP cyclohydrolase II. Preferably, the deletions affect N- or C-terminal amino acids of the corresponding non-modified GTP cyclohydrolase II and do not significantly reduce the functional properties, e.g., the specific activity, of the enzyme.

The polypeptides and polynucleotides of the present invention, including modified GTP cyclohydrolase II enzymes, may be provided in an isolated form, and preferably are purified to homogeneity. As used herein, the term "isolated" means that the material is removed from its original environment (e.g., the natural environment if it is naturally occurring). For example, a naturally-occurring polynucleotide or polypeptide present in a living microorganism is not isolated, but the same polynucleotide or polypeptide, separated from some or all of the coexisting materials in the natural system, is isolated. Such polynucleotides could be part of a vector and/or such polynucleotides or polypeptides may be part of a composition and still be isolated in that such vector or composition is not part of its natural environment. An isolated polypeptide is preferably greater than 80% pure, more preferably greater than 90% pure, even more preferably greater than 95% pure, most preferably greater than 99% pure. Purity may be determined according to methods known in the art, e.g., by SDS-PAGE and subsequent protein staining. Protein bands can then be quantified by densitometry. Further methods for determining the purity are within the level of ordinary skill.

The invention further relates to a polynucleotide comprising a nucleotide sequence which codes for a modified GTP cyclohydrolase II according to the invention. "Polynucleotide" as used herein refers to a polyribonucleotide or polydeoxyribonucleotide that may be unmodified RNA or DNA or modified RNA or DNA. Polynucleotides include but are not limited to single- and double-stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically, double-stranded or a mixture of single- and double-stranded regions. The term "polynucleotide" includes DNA or RNA that comprises one or more unusual bases, e.g., inosine, or one or more modified bases, e.g., tritylated bases.

The polynucleotide of the invention can easily be obtained by modifying a polynucleotide sequence which codes for a non-modified GTP cyclohydrolase II. Examples of such polynucleotide sequences encoding non-modified GTP cyclohydrolase II enzymes include but are not limited to the amino acid sequences in Table 4, in particular to SEQ ID NOs:2, 33, 35, 37, 39, 41, and 43. Non-limiting examples of polynucleotides encoding modified GTP cyclohydrolase II enzymes according to the invention are shown in SEQ ID NOs:6, 8, 10, 12, 14, 16, 18, 20, 22, 24 and 26.

Methods for introducing mutations, e.g., additions, deletions and/or substitutions into the nucleotide sequence coding for the non-modified GTP cyclohydrolase II include but are not limited to site-directed mutagenesis and PCR-based methods.

DNA sequences of the present invention can be constructed starting from genomic or cDNA sequences coding for GTP cyclohydrolase II enzymes known in the state of the art, as are available from, e.g., Genbank (Intelligenetics, California, USA), European Bioinformatics Institute (Hinston Hall, Cambridge, GB), NBRF (Georgetown University, Medical Centre, Washington D.C., USA) and Vecbase (University of Wisconsin, Biotechnology Centre, Madison, Wis., USA) or from the sequence information disclosed in Table 4 by methods of in vitro mutagenesis (see e.g. Sambrook et al., Molecular Cloning, Cold Spring Harbor Laboratory Press, New York). Another possibility of mutating a given DNA sequence which is also preferred for the practice of the present invention is mutagenesis by using the polymerase chain reaction (PCR). DNA as starting material can be isolated by methods known in the art and described, e.g., in Sambrook et al. (Molecular Cloning) from the respective strains/organisms. It is, however, understood that DNA encoding a GTP cyclohydrolase II to be constructed/mutated in accordance with the present invention can also be prepared on the basis of a known DNA sequence, e.g. by construction of a synthetic gene by methods known in the art (as described, e.g., in EP 747483).

The polynucleotide of the invention may be an isolated polynucleotide, i.e. a polynucleotide that is substantially free from other nucleic acid sequences such as but not limited to other chromosomal and extrachromosomal DNA and RNA. Conventional nucleic acid purification methods known to people skilled in the art may be used to obtain isolated polynucleotides. The term also embraces recombinant polynucleotides and chemically synthesized polynucleotides.

In yet another embodiment the invention pertains to a functional polynucleotide in which a promoter, a ribosome-binding site, if necessary as in the case of bacterial cells, and a terminator are operably linked with a polynucleotide according to the invention. In yet a further embodiment the invention pertains to a vector or plasmid comprising such a polynucleotide. The vector or plasmid preferably comprises at least one marker gene. The term "operably linked" as used herein refers to the association of nucleic acid sequences on a single nucleic acid fragment so that the function of one is affected by the other. For example, a promoter is operably linked with a coding sequence when it is capable of affecting the expression of that coding sequence, i.e., the coding sequence is under the transcriptional control of the promoter. Coding sequences may be operably linked to regulatory sequences in sense or anti-sense orientation. The term "expression" denotes the transcription of a DNA sequence into mRNA and/or the translation of mRNA into an amino acid sequence.

The term "over-expression" means the production of a gene product in a modified organism (e.g., modified by transformation or transfection) that exceeds levels of production in the corresponding non-modified organism by deregulating the expression of the gene and/or by multiplying the gene itself inside of the organism.

Once complete DNA sequences of the present invention have been obtained, they may be integrated into vectors or directly introduced into the genome of a host organism by methods known in the art and described in, e.g., Sambrook et al. (s.a.) to (over-) express the encoded polypeptide in appropriate host systems. However, a man skilled in the art knows that also the DNA sequences themselves can be used to transform the suitable host systems of the invention to get (over-) expression of the encoded polypeptide.

Suitable host cells may be eukaryotic or prokaryotic cells. Examples of suitable host cells include but are not limited to bacterial cells such as cells of cyanobacteria, streptococci, staphylococci, enterococci, e.g., *Bacilli* as, e.g., *Bacillus subtilis*, or *Streptomyces*, as, e.g. *Streptomyces lividans* or *Streptococcus pneumoniae*, *E. coli* as, e.g., *E. coli* K12 strains, e.g. M15 or HB 101. The host cells may be a fungal cell including yeast cells, such as cells of *Aspergilli*, e.g. *Aspergillus niger* or *Aspergillus oryzae*, *Trichoderma*, e.g. *Trichoderma reesei*, *Ashbya*, e.g. *Ashbya gossypii*, *Eremothecium*, e.g. *Eremothecium ashbyii*, *Saccharomyces*, e.g. *Saccharomyces cerevisiae*, *Candida*, e.g. *Candida flareri*, *Pichia*, e.g. *Pichia pastoris*, *Hansenula polymorpha*, e.g. *H. polymorpha* (DSM 5215), and *Kluyveromyces*. A suitable host cell may further be selected from animal cells, including mammalian cells, such as for instance CHO, COS, HeLa, 3T3, BHK, 293, CV-1 and insect cells like *Drosophila* S2 and *Spodoptera* Sf9 cells; and plant cells such as cells of a gymnosperm or angiosperm.

Vectors which may be used for expression in fungi are known in the art and described e.g. in EP 420358, or by Cullen et al. (Bio/Technology 5, 369-376, 1987), Ward (in Molecular Industrial Mycology, Systems and Applications for Filamentous Fungi, Marcel Dekker, New York, 1991), Upshall et al. (Bio/Technology 5, 1301-1304, 1987), Gwynne et al. (Bio/Technology 5, 71-79, 1987), or Punt et al. (J. Biotechnol. 17, 19-34, 1991), and for yeast by Sreekrishna et al. (J. Basic Microbiol. 28, 265-278, 1988; Biochemistry 28, 4117-4125, 1989), Hitzemann et al. (Nature 293, 717-722, 1981) or in EP 183070, EP 183071, EP 248227, or EP 263311. Suitable vectors which may be used for expression in *E. coli* are known in the art as described by Sambrook et al. (s.a.). Vectors which may be used for expression in *Bacilli* are known in the art and described, e.g. in EP 207459 or EP 405370, by Yansura and Henner in Proc. Natl. Acad. Sci. USA 81, 439-443 (1984), or by Henner, Le Grice and Nagarajan in Meth. Enzymol. 185, 199-228, 1990. Vectors which maybe used for expression in *H. polymnorpha* are known in the art as described, e.g. in Gellissen et al., Biotechnology 9, 291-295, 1991.

Either such vectors already carry regulatory elements, e.g. promoters, or the polynucleotides of the present invention may be engineered to contain such elements. Suitable promoter elements which may be used are known in the art and are, e.g., for *Trichoderma reesei* the cbh1- or the pki1-promoter, for *Aspergillus oryzae* the amy-promoter, and for *Aspergillus niger* the glaA-, alcA-, aphA-, tpiA-, gpdA- and the pkiA-promoter. Suitable promoter elements which may be used for expression in yeast are known in the art and are, e.g., the pho5- or the gap-promoter for expression in *Saccharomyces cerevisiae*, and e.g. the aox1-promoter for *Pichia pastoris* or the FMD- or MOX promoter for *H. polymorpha*.

Suitable promoters and vectors for bacterial expression include, e.g., a synthetic promoter described by Giacomini et al. (Gene 144, 17-24, 1994), the vegI promoter from *Bacillus subtilis* or the strong bacteriophage T5 promoter. Appropriate teachings for expression of the claimed (mutant) GTP cyclohydrolase II enzymes in bacteria, either by appropriate plasmids or through integration of GTP cyclohydrolase II-encoding DNA sequences into the chromosomal DNA, may be found in many places, e.g., U.S. Pat. No. 6,322,995.

Accordingly, vectors comprising a polynucleotide of the present invention, preferably for the expression of said polynucleotides in bacterial, fungal, animal or plant hosts, and such transformed bacteria or fungal, animal or plant hosts are also an object of the present invention.

The invention further relates to a method for producing riboflavin, a riboflavin precursor, FMN, FAD, or one or more derivatives thereof, comprising:

(a) culturing the host cell of the invention in a suitable medium under conditions that allow expression of the modified GTP cyclohydrolase II in said host cell; and (b) optionally separating the product (riboflavin, a riboflavin precursor, FMN, FAD, or one or more derivatives thereof) from the medium.

Such a method can be used for the biotechnological production of either one or more of the following products: riboflavin, a riboflavin precursor, FMN, FAD, or one or more derivatives thereof. Such derivatives may include flavoproteins.

Methods of genetic and metabolic engineering of suitable host cells according to the present invention are known to the man skilled in the art. Similarly, (potentially) suitable purification methods for riboflavin, a riboflavin precursor, FMN, FAD, or one or more derivatives thereof are well known in the area of fine chemical biosynthesis and production.

It is understood that methods for biotechnological production of riboflavin, a riboflavin precursor, FMN, FAD, or one or more derivatives thereof according to the present invention are not limited to whole-cellular fermentation processes as described above, but may also use, e.g., permeabilized host cells, crude cell extracts, cell extracts clarified from cell remnants by, e.g., centrifugation or filtration, or even reconstituted reaction pathways with isolated enzymes. Also combinations of such processes are in the scope of the present invention. In the case of cell-free biosynthesis (such as with reconstituted reaction pathways), it is irrelevant whether the isolated enzymes have been prepared by and isolated from a host cell, by in vitro transcription/translation, or by still other means.

The invention further relates to a method for producing a modified GTP cyclohydrolase II of the invention comprising:

(a) culturing a host cell of the invention under conditions that allow expression of the modified GTP cyclohydrolase II of the invention; and (b) recovering the modified GTP cyclohydrolase II from the cells or from the media.

The modified GTP cyclohydrolase II enzymes of the invention may be prepared from genetically engineered host cells comprising appropriate expression systems.

For recombinant production of the polypeptides of the invention, host cells may be genetically engineered to incorporate polynucleotides or vectors or plasmids of the invention. Introduction of a polynucleotide or vector into the host cell may be effected by standard methods known in the art such as calcium phosphate transfection, DEAE-dextran mediated transfection, microinjection, cationic lipid-mediated transfection, electroporation, transduction, ballistic introduction and infection.

A great variety of expression systems may be used to produce the modified GTP cyclohydrolase II enzymes of the invention. Such vectors include, among others, those described supra. Generally, any system or vector suitable to maintain, propagate or express polynucleotides and/or to express a polypeptide in a host may be used for expression in this regard.

In recombinant expression systems in eukaryotes, for secretion of a translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

Polypeptides of the invention may be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxyapatite chromatography, and high performance liquid chromatography. Well-known techniques for protein refolding may be employed to regenerate active conformation when the polypeptide is denatured during isolation and/or purification.

GTP cyclohydrolase II enzymes of the present invention may also be expressed in plants according to methods as described, e.g., by Pen et al. in Bio/Technology 11, 811-814, 1994 or in EP 449375, preferably in seeds as described, e.g., in EP 449376. Some suitable examples of promoters and terminators include those from nopaline synthase (nos), octopine synthase (ocs) and cauliflower mosaic virus (CaMV) genes. One type of efficient plant promoter that may be used is a high-level plant promoter. Such promoters, in operable linkage with the genetic sequences of the present invention should be capable of promoting expression of a gene product of the present invention. High-level plant promoters that may be used in this invention include the promoter of the small subunit (ss) of the ribulose-1,5-bisphosphate carboxylase, for example from soybean, and the promoter of the chlorophyll a/b binding protein.

Where commercial production of the instant proteins is desired, a variety of culture methodologies may be applied. For example, large-scale production of a specific gene product, overexpressed from a recombinant microbial host may be achieved by both batch or continuous culture methodologies. Batch and fed-batch culturing methods are common and well known in the art, and examples have been described by Thomas D. Brock in Biotechnology: A Textbook of Industrial Microbiology, Second Edition (1989), Sinauer Associates, Inc., Sunderland, Mass., or Deshpande, Appl. Biochem. Biotechnol. 36, 227-234, 1992. Methods of modulating nutrients and growth factors for continuous culture processes as well as techniques for maximizing the rate of product formation are well known in the art of industrial microbiology, and a variety of methods are detailed by Brock, supra.

Fermentation media may further contain suitable carbon substrates. Suitable substrates may include but are not limited to monosaccharides such as glucose and fructose, oligosaccharides such as lactose or sucrose, polysaccharides such as starch or cellulose or mixtures thereof and unpurified mixtures from renewable feedstocks. It is contemplated that the source of carbon utilized in the present invention may encompass a wide variety of carbon containing substrates and will only be limited by the choice of organism.

The invention further relates to a method for the preparation of a GTP cyclohydrolase II having increased specific activity, comprising the following steps:

(a) providing a polynucleotide encoding a first GTP cyclohydrolase II with a specific activity that, desirably, should be increased;

(b) introducing one or more mutation(s) into the polynucleotide sequence such that the mutated polynucleotide sequence encodes a modified GTP cyclohydrolase II comprising one or more mutation(s) when compared to the first GTP cyclohydrolase II wherein the one or more mutation(s) include 1, 2, 3, 4, 5, or 6 mutation(s) on amino acid position(s) corresponding to positions 261, 270, 276, 279, 308 and/or 347 of SEQ ID NO:2;

(c) optionally inserting the mutated polynucleotide in a vector or plasmid;

(d) introducing the polynucleotide or the vector or plasmid into a suitable host cell; and (e) culturing the host cell under conditions that allow expression of the modified GTP cyclohydrolase II.

The present invention includes further the provision of a method for the preparation of a GTP cyclohydrolase II having increased specific activity, comprising the following steps:

(a) providing a polynucleotide encoding a first GTP cyclohydrolase II with a specific activity that, desirably, should be increased;

(b) providing the positions that have an effect on the specific activity;

(c) defining the optimal amino acid for replacement of a given amino acid of the wild-type GTP cyclohydrolase II as defined in (b) and introducing one or more mutations into the polynucleotide sequence of (a) at the positions defined in (b) such that the mutated polynucleotide sequence encodes a new GTP cyclohydrolase II;

(d) optionally inserting the mutated polynucleotide in a vector or plasmid;

(d) introducing the polynucleotide or the vector or plasmid into a suitable host cell; and (e) culturing the host cell under conditions that allow expression of the modified GTP cyclohydrolase II.

In one embodiment, step (c) or the method described above is performed via saturated mutagenesis. However, it is understood that this may be not the only way to define the amino acid which should replace an amino acid at a given position of the wild-type GTP cyclohydrolase II in order to obtain a modified GTP cyclohydrolase II with increased specific activity.

The preparation of a modified GTP cyclohydrolase II having increased specific activity from a non-modified GTP cyclohydrolase II as described above, e.g., via saturated mutagenesis, includes, but is not limited to, the preparation of mutated GTP cyclohydrolase II proteins from non-modified proteins as in Table 4, in particular those identified by SEQ ID NOs:2, 33, 35, 37, 39, 41, and 43, such as for example non-modified GTP cyclohydrolase II proteins of Bacillus subtilis or Ashbya gossypii. The primers used for the PCR reaction are such that one primer, e.g., the sense primer, may contain a mutated nucleotide sequence and the other primer, e.g., the anti-sense primer, may contain the wild-type nucleotide sequence. PCR with these primer pairs and genomic DNA of the wild-type ribA may result in a PCR product carrying the particular mutation at a given position, depending on the mutated nucleotide sequence of the primer used. After purification of the resulting PCR products using standard methods like, e.g., the QIAquick PCR purification kit (Qiagen), the DNA may be cut with restriction enzymes such as BamHI and EcoRI, ligated into a suitable vector, e.g., pQE60, and transformed into a strain which is negative for GTP cyclohydrolase II. An example for such a strain is the E. coli strain Rib7 (Richter et al., J. Bacteriol. 175, 4045-4051, 1993) containing the plasmid pREP4. After confirmation of the correct sequence by DNA sequencing, the mutated RibA may be purified and characterized as described above. If Ashbya gossypii is used for the generation of a GTP cyclohydrolase II having increased specific activity, saturated mutagenesis has to be performed at amino acid residues/positions T126, G135, A141, L144, N182 and I221 corresponding to the respective residues V261, G270, A276, Q279, K308 and M347 of Bacillus subtilis GTP cyclohydrolase II as of SEQ ID NO:2 that were shown to have an impact on the specific activity of the latter enzyme (see Table 4).

The preferred embodiments of this method correspond to the preferred embodiments of the modified GTP cyclohydrolase II, the polynucleotides encoding them, the vectors and plasmids, the host cells, and the methods described herein. The first and second GTP cyclohydrolase II correspond to the non-modified and modified GTP cyclohydrolase II, respectively (see supra).

It is an object of the present invention to provide a polynucleotide comprising a nucleic acid sequence coding for a modified GTP cyclohydrolase II as described above, a vector, preferably an expression vector, comprising such a polynucleotide, a host cell which has been transformed by such a polynucleotide or vector, a process for the preparation of a GTP cyclohydrolase II of the present invention wherein the host cell as described before is cultured under suitable culture conditions and the GTP cyclohydrolase II is isolated from such host cell or the culture medium by methods known in the art, and a process for the biotechnological production of riboflavin, a riboflavin precursor, FMN, FAD, or one or more derivatives thereof based on a host cell which has been transformed by such a polynucleotide or vector, and/or which may have stably integrated such a polynucleotide into its chromosome(s).

It is also an object of the present invention to provide (i) a DNA sequence which codes for a GTP cyclohydrolase II carrying at least one of the specific mutations of the present invention and which hybridizes under standard conditions with any of the DNA sequences of the specific modified GTP cyclohydrolase II enzymes of the present invention, or (ii) a DNA sequence which codes for a GTP cyclohydrolase II carrying at least one of the specific mutations of the present invention but, because of the degeneracy of the genetic code, does not hybridize but which codes for a polypeptide with exactly the same amino acid sequence as a DNA sequence which hybridizes under standard conditions with any of the DNA sequences of the specific modified GTP cyclohydrolase II enzymes of the present invention, or (iii) a DNA sequence which is a fragment of such DNA sequences which maintains the activity properties of the polypeptide of which it is a fragment.

"Standard conditions" for hybridization mean in the context of the present invention the conditions which are generally used by a man skilled in the art to detect specific hybridization signals and which are described, e.g. by Sambrook et al., "Molecular Cloning", second edition, Cold Spring Harbor Laboratory Press 1989, New York, or preferably so-called stringent hybridization and non-stringent washing conditions or more preferably so-called stringent hybridization and stringent washing conditions a man skilled in the art is familiar with and which are described, e.g., in Sambrook et al. (s.a.). A specific example of stringent hybridization conditions is overnight incubation (e.g., 15 hours) at 42° C. in a solution comprising: 50% fornamide, 5×SSC (150 mM NaCl, 15 mM trisodium citrate), 50 mM sodium phosphate (pH 7.6), 5× Denhardt's solution, 10% dextran sulfate, and 20 µg/ml of denatured, sheared salmon sperm DNA, followed by washing the hybridization support in 0.1×SSC at about 65° C.

It is furthermore an object of the present invention to provide a DNA sequence which can be obtained by the so-called polymerase chain reaction method ("PCR") by PCR primers designed on the basis of the specifically described DNA sequences of the present invention. It is understood that the so obtained DNA sequences code for GTP cyclohydrolase II enzymes with at least the same mutation as the ones from which they are designed and show comparable activity properties.

The various embodiments of the invention described herein may be cross-combined.

Multiple sequence alignment was calculated by the program PILEUP of the GCG program package of 92 GTP cyclohydrolase II sequences found by the program BLASTN using standard databases as SWISS-PROT and TrEMBL (Candida guilliermondii, Ashbya gossypii, Saccharomyces cerevisiae, Neurospora crassa, Schizosaccharomyces pombe, Archaeoglobus fulgidus, Streptomyces coelicolor, Helicobacter pylori J99, Helicobacter pylori, Pyrococcus furiosus, Thermotoga maritima, Chlamydia muridarum, Chlamydia trachomatis, Chlamydia caviae GPIC, Arabidopsis thaliana, Lycopersicum exculentum, Oryza sativa, Alcaligenes eutrophus, Neisseria meningitidis (serogroup A), Neisseria meningitidis (serogroup B, two GTP cyclohydrolase II enzymes), Pseudomonas putida (two GTP cyclohydrolase II enzymes), Pseudomonas syringae (two GTP cyclohydrolase II enzymes), Actinobacillus actinomycetemcomitans (Haemophilus actinomycetemcomitans), Haemophilus influenzae, Pasteurella multocida, Escherichia coli, Escherichia coli O6, Salmonella typhimurium, Yersinia pestis, Buchnera aphidicola (subsp. Acyrthosiphon pisum) (Acyrthosiphon pisum symbiotic bacterium), Buchnera aphidicola (subsp. Schizaphis graminum), Wigglesworthia glossinidia brevipalpis, Buchnera aphidicola (subsp. Baizongia pistaciae), Mycobacterium leprae, Mycobacterium tuberculosis, Corynebacterium efficiens, Corynebacterium glutamicum, Corynebacterium ammoniagenes (Brevibacterium ammoniagenes), Staphylococcus aureus, Staphylococcus epidermidis, Actinobacillus pleuropneumoniae, Lactococcus lactis (Streptococcus lactis), Streptococcus agalactiae, Streptococcus pneumoniae, Clostridium acetobutylicum, Fusobacterium nucleatum, Anabaena spec., Synechocystis spec., Synechococcus elongatus (Thermosynechococcus elongatus), Bacillus amyloliquefaciens, Bacillus subtilis, Bacillus cereus, Bacillus halodurans, Clostridium perfringens, Clostridium tetani, Chlorobium tepidum, Aquifex aeolicus, Leptospira initerrogans, Deiniococcus radiodurans, Bacteroides thetaiotaomicron, Caulobacter crescentus, Coxiella burnetii, Rhizobium etli, Lactobacillus plantarum, Pseudomonas glumae, Streptomyces avermitilis, Photobacterium phosphoreum, Azospirillum brasilense, Agrobacterium tumefaciens, Rhizobium meliloti (Sinorhizobium meliloti), Brucella melitensis, Brucella suis, Rhizobium loti (Mesorhizobium loti), Nitrosomonas europaea, Ralstonia solanacearum (Pseudomonas solanacearum), Xanthomonas axonopodis, Xanthoinonas campestris, Vibrio parahaemolyticus, Vibrio vulnificus, Vibrio cholerae, Vibrio fischeri, Shewanella oneidensis, Photobacterium phosphoreum, Photobacterium leiognathi, Pseudomonas aeruginosa, Dehalospirillum multivorans, Xylella fastidiosa). Numbering relates to the alignment made. Some of the amino acid sequences code for an enzyme that has just GTP cyclohydrolase II activity like the enzymes from Ashbya gossypii, Streptomyces coelicolor, Helicobacter pylori J99, Heliobacter pylori, Arabidopsis thaliana, Alcaligenes eutrophus, Neisseria meningitidis (serogroup A), Neisseria meningitidis (serogroup B), Pseudomonas putida, Pseudomonas syringae, Actinobacillus actinomycetemcomitans (Haemophilus actinomycetemcomitans), Haemophilus influenzae, Pasteurella multocida, Escherichia coli, Escherichia coli O6, Salmonella typhimurium, Yersinia pestis, Buchnera aphidicola (subsp. Acyrthosiphon pisum) (Acyrthosiphon pisum symbiotic bacterium), Buchnera aphidicola (subsp. Schizaphis graminum), Wigglesworthia glossinidia brevipalpis, Buchnera aphidicola (subsp. Baizongia pistaciae), Pseudomonas glumae, Streptomyces avermitilis, or Photobacterium phosphoreum. Other enzymes like the RibA enzyme from B. subtilis contain, in addition, a domain having DHBP synthase activity. Positions that are homologous/equivalent to the amino acid residues found to have a positive effect on specific activity (amino acid residues 261, 270, 276, 279, 308, 347) and on protease sensitivity (196) of RibA from B. subtilis are discussed in one of the following examples. The numbering used for those positions is done according to the B. subtilis wild-type amino acid sequence.

The following non-limiting examples further illustrate the invention.

EXAMPLE 1

Measurement of GTP Cyclohydrolase II Activity and Determination of Specific Activity The enzymatic assay used for measuring GTP cyclohydrolase II activity was adapted from Ritz et al. (J. Biol. Chem. 276, 22273-22277, 2001). The final assay buffer contained 50 mM Tris/HCl, pH 8.5, 10 mM $MgCl_2$, 7.5 mM mercaptoethanol, 2.5 mM GTP and 0.1 mg/ml bovine serum albumin. After purification (see Example 5), the enzyme was kept in a buffer containing 50 mM Tris/HCl, pH 8.5, 10 mM $MgCl_2$, 7.5 mM mercaptoethanol, and 10% glycerol. Substrate was added to the enzyme and the absorption at 310 nm, at which GTP shows no absorption, was followed over 20-30 min. The final reaction mixture contained between 0.02 and 0.04 mg/ml GTP cyclohydrolase II from B. subtilis or one of the mutants as shown in Table 1 or 2. An absorption coefficient of 6.28 [$mM^{-1} cm^{-1}$] for DRAPP was used for the calculation of the activity. Protein determination was done with the Protein Assay from Bio-Rad (Cat. No. 500-0002, Bio-Rad Laboratories AG, Nenzlingerweg 2, CH-4153 Reinach, Switzerland).

According to the definition of "specific activity" given above, one unit is the amount of RibA that catalyzes the formation of 1 μmol DRAPP per minute under the conditions as described above. The specific activity is the amount of DRAPP that is formed by 1 mg of RibA per minute under the conditions as described above. Using the aforementioned definitions, the specific GTP cyclohydrolase II activity of the $His_6$-tagged RibA protein of B. subtilis was 0.115 U/mg.

EXAMPLE 2

Testing of the Quality of the Enzymatic Assay

An optimal assay should fulfill a number of requirements, such as linearity with enzyme concentration and linearity with time. Using the conditions described in Example 1 and 22 μg enzyme, the increase in the absorption at 310 nm was followed over 25 min. To test in which range the assay is linear with the enzyme concentration, the dependence of the assay on increasing enzyme concentration (0-40 μg $His_6$-tagged RibA) was tested. The assay proved to be linear over 25 min and between 0 and 40 μg $His_6$-tagged RibA from B. subtilis.

After this the dependence of the GTP cyclohydrolase II activity of $His_6$-tagged RibA from B. subtilis on GTP concentration was tested. The conditions as described in Example 1 were used. However, the GTP concentration was varied from 0.05 to 2.5 mM final concentration. The data indicate a $K_m$ value for GTP of 0.07 mM and a specific activity of around 115 mU/mg protein at 37° C. for the GTP cyclohydrolase II activity of the $His_6$-tagged RibA enzyme from *B. subtilis*. The experiments of this example showed that the GTP cyclohydrolase II activity assay, in fact, is linear with time and enzyme (GTP cyclohydrolase II) concentration, and that under the given conditions for *Bacillus subtilis* GTP cyclohydrolase II, a GTP concentration of 2.5 mM may be optimal to allow reliable measurements of the specific activity of the enzyme.

EXAMPLE 3

Isolation of Genomic DNA from *Bacillus Subtilis*

*B. subtilis* was grown at 30° C. in Veal Infusion Broth (Becton Dickinson, Sparks, Md. 21152, USA) overnight. 1.5 ml culture was transferred into a 1.5 ml tube and centrifuged.

The cell pellet was resuspended in 0.5 ml suspension buffer (50 mM Tris/HCl, pH 7.5, 50 mM $Na_2EDTA$, 15% sucrose and 1 mg/ml freshly added lysozyme). After 10 min incubation at room temperature 1 μl diethyloxydiformate was added. Then 10 μl of 10% SDS solution was added and the tube was inverted several times. The tube was incubated for 5 min at 70° C. to release the bacterial DNA. 50 μl 5 M potassium acetate was added, the tube was cooled on ice and left there for 45 min. After this, the sample was centrifuged for 30 min at 4° C. The supernatant was transferred into a new 1.5-ml tube, which was filled (up to 1.5 ml) with ethanol at room temperature. After 5 min centrifugation, the supernatant was discarded and the DNA pellet was dried. Then the DNA was washed with 70% and 96% ethanol and dissolved in 10 mM Tris/HCl, pH 7.5, 1 mM EDTA, and 10 μg/ml RNase A.

EXAMPLE 4

Construction of the Expression Plasmids for Expressing RibA Coding for GTP Cyclohydrolase II and DHBP Synthase from *B. Subtilis* and its Mutants Cloning of the ribA gene (SEQ ID NO:1) of *B. subtilis* that codes for the GTP cyclohydrolase II and the DHBP synthase was done by PCR. Genomic DNA of *B. subtilis* was isolated according to Example 3. 100 ng of this DNA or of a template coding for a mutated form of the ribA gene were used for a PCR using primers RibA 1S (SEQ ID NO:27) and RibA 1AS (SEQ ID NO:28). The following PCR conditions were used: 2 μM of each primer, 0.2 mM of each nucleotide, 2.5 U of a proof-reading DNA polymerase (Stratagene, Gebouw Calif., 1101 CB Amsterdam Zuidoost, The Netherlands), and 100 ng genomic DNA in the appropriate buffer as supplied together with the DNA polymerase.

Temperature regulation was as follows:
Step 1: 3 min at 95° C.
Step 2: 30 sec at 95° C.
Step 3: 30 sec at 52° C.
Step 4: 60 sec at 72° C.
Steps 2 to 4 were repeated 30-times.

The PCR product of 1.3 kb was used as template for PCR 2, in which primer RibA 1S was replaced by primer RibA 2S (SEQ ID NO:29). The PCR product of this reaction (SEQ ID NO:3), encoding an N-terminally $His_6$-tagged version of *B. subtilis* RibA (SEQ ID NO:4), was separated by agarose gel electrophoresis, eluted from the gel, digested with EcoRI and BamHI, and ligated into the EcoRI and BamHI digested vector pQE60 (Qiagen AG, Hilden, Germany). The plasmid was called pQE60ribANhis.

EXAMPLE 5

Characterization of the Wild-Type and the Mutant Enzymes

The generation of mutated enzymes was performed using methods described above and which are known to the skilled person. Mutants of RibA from *B. subtilis* that were further investigated are depicted in Table 1. All mutant genes were cloned into a pQE60 vector as described in Example 4. All final constructs contained an N-terminal $His_6$-tag.

TABLE 1

Rib A mutants as defined by the amino acid exchanges compared to the wild-type RibA protein of *B. subtilis* (the numbers define the respective amino acid positions in SEQ ID NO: 2)

| Mutant | SEQ ID NO (DNA) | SEQ ID NO (protein) |
| --- | --- | --- |
| RibA M347I | 9 | 10 |
| RibA G270R | 23 | 24 |
| RibA K220E, G270A | 19 | 20 |
| RibA Y196C, A276T, A282T (PCR III) | 11 | 12 |
| RibA Y196C, A276T | 5 | 6 |
| RibA Y196C, V261A | 7 | 8 |
| RibA Y196C, V261A, A276T | 25 | 26 |
| RibA Y196C, A276T, A282T, M347I | 13 | 14 |
| RibA Y196C, A276T, Q279R, A282T, M347I | 15 | 16 |
| RibA Y196C, A276T, Q279R, A282T, K308R, M347I (construct C) | 17 | 18 |
| RibA Y196C, A276T, Q279R, A282T, K308R, F325Y, M347I (construct E) | 21 | 22 |

The RibA mutant enzymes were expressed from the plasmids of Example 4 and purified as described in "The QiaExpressionist", Qiagen, Hilden, Germany, March 2001, edition 5. The enzymatic properties of the purified enzymes (RibA mutants) were analyzed as described in Examples 1 and 2. Table 2 compares the specific GTP cyclohydrolase II activities of the RibA mutants (see Table 1) to that of the GTP cyclohydrolase II of the wild-type RibA of *B. subtilis*. The activity was measured using the N-terminally $His_6$-tagged enzyme versions of RibA as described in Example 4. The numbers define the respective amino acid positions in SEQ ID NO:2.

TABLE 2

Comparison of the specific GTP cyclohydrolase II activities of mutated and wild-type (WT) *B. subtilis* RibAs (all N-terminally $His_6$-tagged)

| Mutations | specific activity (in % relative to wild-type RibA) |
| --- | --- |
| WT | 100 |
| M347I | 120 |
| G270R | 140 |
| G270A, (K220E) | 160 |
| (Y196C), A276T, (A282T) | 160 |
| (Y196C), A276T | 160 |
| (Y196C), V261A | 160 |
| (Y196C), V261A, A276T | 160 |
| (Y196C), A276T, (A282T), M347I | 180 |
| (Y196C), A276T, Q279R, (A282T), M347I | 185 |
| (Y196C), A276T, Q279R, (A282T), K308R, M347I | 201 |
| (Y196C), A276T, Q279R, (A282T), K308R, (F325Y), M347I | 200 |

The amino acid replacements in parentheses have most probably no effect on GTP cyclohydrolase II activity of the mutants. Amino acid exchange Y196C reduces the protease sensitivity of RibA.

EXAMPLE 6

Construction of Recombinant *B. Subtilis* Strains Over-Expressing RibA Mutants that Show a Higher Specific GTP Cyclohydrolase II Activity In the following example, the mutated ribA polynucleotide sequences of RibA Y196C,A276T,282T (PCR III), RibA Y196C,A276T,Q279R,A282T,K308R,M347I (construct C), and RibA Y196C,A276T,Q279R,A282T,K308R,F325Y, M347I (construct E) were first introduced into a vector containing the strong constitutive promoter $P_{vegI}$, and then further manipulated in *E. coli*. Transformation of a natural competent *B. subtilis* microorganism with the polynucleotide sequence and flanking vector sequences resulted in a *B. subtilis* strain over-expressing the mutated ribA. Standard recombinant DNA techniques were used for the construction of the polynucleotide sequence and the *B. subtilis* strains. See, for example, Sambrook et al., Molecular Cloning. A Laboratory Manual ($2^{nd}$ Ed.), Cold Spring Harbor Laboratory Press (1989), and Harwood and Cutting, Molecular Biology Methods for *Bacillus*, John Wiley and Sons (1990).

To amplify the mutated ribA, a 1.2-kb DNA fragment containing the entire ribA coding sequence was amplified by PCR using DNA from a plasmid containing mutants PCR III, construct C or construct E, and RibANde+1 (SEQ ID NO:30) and RibA4AS (SEQ ID NO:31) as primers.

The reaction conditions for the PCR reaction consisted of 30 cycles of denaturation at 95° C. for 1 min, annealing at 52° C. for 1 min, and extension at 72° C. for 2 min. The Pfu Turbo DNA polymerase (Stratagene, Gebouw Calif., 1101 CB Amsterdam Zuidoost, The Netherlands) was used to minimize PCR-generated errors. The PCR products were purified using the QIAquick PCR purification kit (Qiagen), and doubly digested using NdeI and BamHI. The digested PCR products were cloned into the pXI16 vector (Huembelin et al., J. Ind. Microbiol. Biotechnol. 22, 1-7, 1999), which consists of suitable restriction sites for the cloning of polynucleotide sequences immediately downstream of the strong constitutive $P_{vegI}$ promoter from *B. subtilis*. The pXI16 vector also contains the cryT transcriptional terminator from *B. thuringiensis*, the sacB flanking sequences for homologous recombination into the *B. subtilis* genome by a double-crossover event, and an erythromycin-resistance marker. That each plasmid contained the mutated ribA was confirmed by DNA sequencing.

Each plasmid was digested with ApaI to remove the spacer region from the $P_{vegI}$ promoter, re-ligated and digested again with FspI, and transformed into natural competent *B. subtilis* 1012 cells. Transformants were selected on TBAB plates (Tryptose Blood Agar Base, Becton Dickinson, Sparks, Md. 21152, USA) containing erythromycin to a final concentration of 2 µg/ml. DNA sequencing verified that the mutated ribA polynucleotide sequences were correct in these strains. Overproduction of riboflavin was tested according to Example 7.

The mutated ribA polynucleotide sequences driven by the $P_{vegI}$ promoter were introduced into riboflavin over-producing *B. subtilis* strain RB50::(pRF69)$_n$::(pRF93)$_m$, which has been described in Perkins et al., J. Ind. Microbiol. Biotechnol. 22:8-18 (1999), by generalized transduction. Standard techniques using bacteriophage PBS1 were employed according to Harwood and Cutting, Molecular Biology Methods for *Bacillus*, John Wiley and Sons (1990). Transductants were selected for on TBAB plates containing erythromycin to a final concentration of 2 µg/ml. Transformants were checked by PCR analysis and DNA sequencing to verify correct insertion of the mutated ribA polynucleotide sequence.

EXAMPLE 7

Improved Production of Riboflavin Using a GTP Cyclohydrolase II with Increased Specific Activity To test the in vivo effect of mutations affecting the specific activity of GTP cyclohydrolase II, the *Bacillus subtilis* GTP cyclohydrolase II (RibA) mutants PCR III, construct C, or construct E were introduced into riboflavin over-producing *B. subtilis* strains, such as strain RB50::(pRF69)$_n$::(pRF93)$_m$ (Perkins et al, J. Ind. Microbiol. Biotechnol. 22, 8-18, 1999), e.g. in the sacB locus. The production of riboflavin was compared directly in two recombinant strains of *B. subtilis* that differ only by the presence or absence of the mutations in the ribA gene. Culturing of the *Bacillus* strains was done as described in Example 8.

EXAMPLE 8

Culture Conditions for Evaluating Riboflavin Production

Riboflavin production was tested in fed-batch cultivations of riboflavin-overproducing *B. subtilis* strain RB50:: (pRF69)$_n$::(pRF93)$_m$ in which the GTP cyclohydrolase II mutants PCR III, construct C, or construct E driven by the $P_{vegI}$ promoter were integrated in the sacB locus (see Example 6). Fermentation of the strains was done as described in EP 405370.

EXAMPLE 9

Analytical Methods for Determination of Riboflavin

For determination of riboflavin, the following analytical method can be used (Bretzel et al, J. Ind. Microbiol. Biotechnol. 22, 19-26, 1999).

The chromatographic system was a Hewlett-Packard 1100 System equipped with a binary pump, a column thermostat and a cooled autosampler. Both a diode array detector and a fluorescence detector were used in line. Two signals were recorded, UV at 280 nm and a fluorescence trace at excitation 446 nm, emission 520 nm.

A stainless-steel Supelcosil LC-8-DB column (150×4.6 mm, 3 µm particle size) was used, together with a guard cartridge. The mobile phases were 100 mM acetic acid (A) and methanol (B). A gradient elution according to the following scheme was used:

| Time [min] | % A | % B |
|---|---|---|
| 0 | 98 | 2 |
| 6 | 98 | 2 |
| 15 | 50 | 50 |
| 25 | 50 | 50 |

The column temperature was set to 20° C., and the flow rate was 1.0 ml/min. The run time was 25 min.

Fermentation samples were diluted, filtered and analyzed without further treatment. Riboflavin was quantitated by comparison with an external standard. The calculations were based on the UV signal at 280 nm. Riboflavin purchased from Fluka (9471 Buchs, Switzerland) was used as standard material (purity≧99.0%).

EXAMPLE 10

Identification of Corresponding Residues in GTP Cyclohydrolase II Enzymes that are Homologous to *Bacillus subtilis* GTP Cyclohydrolase II A multiple amino acid sequence alignment of 92 different GTP cyclohydrolase II enzymes found by the program BLASTN using standard databases such as SWISS-PROT and TrEMBL was calculated with the program "PILEUP" (GCG Wisconsin Package, version 10.2, Accelrys Inc., 9685 Scranton Road, San Diego, Calif. 92121-3752, USA) using the following parameters: gap creation penalty 8, gap extension penalty 2, and blosum62.cmp matrix (default parameters).

A homologous GTP cyclohydrolase II in the context of the present invention may show sequence similarity with any of the GTP cyclohydrolase II amino acid sequences shown in Table 4, which. serves as an example and is not meant to be a complete collection of all known GTP cyclohydrolase II enzymes. Homologous residues, i.e. residues of the different GTP cyclohydrolase II enzymes that are located at the same position in the amino acid sequence alignment, are expected to be similarly positioned in the 3D structure of each protein and to fulfill in each protein a comparable function structure-wise and function-wise. Amino acid residues homologous to the amino acid residues of the GTP cyclohydrolase II from *B. subtilis* are discussed in the Examples.

Amino acid residues of 92 different organisms corresponding to specific amino acid positions, i.e. positions that are homologous/equivalent to the amino acid residues found to have a positive effect on specific activity (amino acid residues 261, 270, 276, 279, 308, 347) of the amino acid sequence of *Bacillus subtilis* GTP cyclohydrolase II (SEQ ID NO:2) are summarized in Table 4, wherein the number in the left column defines the organism, starting with the name of the sequence used, the database accession number, and in parenthesis the source organism of the sequence:

(1) gch2_bacsu: SWISS-PROT: gch2_bacsu (*Bacillus subtilis*)
(2) gch2_cangu: geneseqp:aay69776 (*Candida guilliermondii*)
(3) gch2_ashgo: TrEMBL: CAA02912: (*Ashbya gossypii* (*Eremothecium gosypii*))
(4) gch2_yeast: SWISS-PROT: gch2_yeast (*Saccharomyces cerevisiae*)
(5) gch2_neucr: TrEMBL: Q871B3 (*Neurospora crassa*)
(6) gch2_schpo: TrEMBL: Q9P7M9 (*Schizosaccharomyces pombe*)
(7) gch2_arcfu: SWISS-PROT: gch2_arcfu (*Archaeoglobus fulgidus*)
(8) gch2_strco: SWISS-PROT: gch2_strco (*Streptomyces coelicolor*)
(9) gch2_helpj: SWISS-PROT: gch2_helpj (*Helicobacter pylori* J99)
(10) gch2_helpy: SWISS-PROT: gch2_helpy (*Heliobacter pylori*)
(11) gch2_pyrfu: TrEMBL: Q8U4L7 (*Pyrococcus furiosus*)
(12) gch2_thema: SWISS-PROT: gch2_thema (*Thermotoga maritima*)
(13) gch2_chlmu: SWISS-PROT: gch2_chlmu (*Chlamydia muridarum*)
(14) gch2_chltr: SWISS-PROT: gch2_chltr (*Chlamydia trachomatis*)
(15) gch2_chlca: TrEMBL: AAP05635 (*Chlamydia caviae* GPIC)
(16) gch2_chlpn: SWISS-PROT: gch2_chlpn (*Chlamydia pneumoniae*)
(17) gch2_arath: SWISS-PROT: gch2_arath (*Arabidopsis thaliana*)
(18) gch2_lyces: TrEMBL: CAC09119 (*Lycopersicum esculentum*)
(19) gch2_orysa: TrEMBL: AAO72560 (*Oryza sativum*)
(20) gch2_alceu: TrEMBL: Q9F184 (*Alcaligenes eutrophus*)
(21) gch2_neima: SWISS-PROT: gch2_neima (*Neisseria meningitidis* (serogroup A))
(22) gch2_neimb: SWISS-PROT: gch2_neimb (*Neisseria meningitidis* (serogroup B))
(23) gch2_psepk: SWISS-PROT: gch2_psepk (*Pseudomonas putida* (strain KT2440))
(24) gch2_psesm: SWISS-PROT: gch2_psesm (*Pseudomonas syringae* (pv. tomato))
(25) gch2_actac: TrEMBL: Q9JRR0 (*Actinobacillus actinomycetemcomitans* (*Haemophilus actinomycetemcomitans*))
(26) gch2_haein: SWISS-PROT: gch2_pasmu gch2_haein (*Haemophilus influenzae*)
(27) gch2_pasmu: SWISS-PROT: (*Pasteurella multocida*)
(28) gch2_ecO6: TrEMBL: Q8FHU5 (*Escherichia coli* O6)
(29) gch2_ecoli: SWISS-PROT: gch2_ecoli (*Escherichia coli*)
(30) gch2_salty: TrEMBL: Q8XFY7 (*Salmonella typhimurium*)
(31) gch2_yerpe: TrEMBL: Q8ZEF0 (*Yersinia pestis*)
(32) gch2_bucai: SWISS-PROT: gch2_bucai (*Buchnera aphidicola* (subsp. *Acyrthosiphon pisum*) (*Acyrthosiphon pisum* symbiotic bacterium))
(33) gch2_bucap: SWISS-PROT: gch2_bucap (*Buchnera aphidicola* (subsp. *Schizaphis graminum*))
(34) gch2_wigbr: SWISS-PROT: gch2_wigbr (*Wigglesworthia glossinidia brevipalpis*)
(35) gch2_bucbp: SWISS-PROT: gch2_wigbr (*Buchnera aphidicola* (subsp. *Baizongia pistaciae*))
(36) gch2_mycle: TrEMBL: Q9CCP4 (*Mycobacterium leprae*)
(37) gch2_myctu: SWISS-PROT: gch2_myctu (*Mycobacterium tuberculosis*)
(38) gch2_coref: TrEMBL: Q8FT57 (*Corynebacterium efficiens*)
(39) gch2_corgl: GENESEQP: AAB79913 (*Corynebacterium glutamicum*)
(40) gch2_coram: SWISS-PROT: gch2_coram (*Corynebacterium ammoniagenes* (*Brevibacterium ammoniagenes*))
(41) gch2_staau: TrEMBL: Q8NW14 (*Staphylococcus aureus* (strain MW2))
(42) gch2_staep: GENESEQP: ABP40248 (*Staphylococcus epidermidis*)
(43) gch2_actpl: SWISS-PROT: gch2_actpl (*Actinobacillus pleuropneumoniae*)
(44) gch2_lacla: TrEMBL: Q9CGU7 (*Lactococcus lactis* (subsp. *lactis*) (*Streptococcus lactis*))
(45) gch2_stcag: TrEMBL: Q8E658 (*Streptococcus agalactiae* (serotype III))

(46) gch2_stcpn: TrEMBL: Q8DRF1 (*Streptococcus pneumoniae* (strain ATCC BAA-255/R6))
(47) gch2_cloac: TrEMBL: Q97LG9 (*Clostridium acetobutylicum*)
(48) gch2_fusnu: TrEMBL: Q8RIR1 (*Fusobacterium nucleatum* (subsp. *nucleatum*))
(49) gch2_anasp: TrEMBL: Q8RIR1 (*Anabaena* sp. (strain PCC 7120))
(50) gch2_syny3: SWISS-PROT: gch2_syny3 (*Synechocystis* sp. (strain PCC 6803))
(51) gch2_synel: TrEMBL: Q8DI64 *Synechococcus elongatus* (*Thermosynechococcus elongatus*)
(52) gch2_bacam: SWISS-PROT: gch2_bacam (*Bacillus amyloliquefaciens*)
(53) gch2_bacce: TrEMBL: AAP11030 (*Bacillus cereus* ATCC 14579)
(54) gch2_bacha: TrEMBL: Q9KCL5 (*Bacillus halodurans*)
(55) gch2_clope: TrEMBL: Q8XMX0 (*Clostridium perfringens*)
(56) gch2_clote: TrEMBL: Q897Q8 (*Clostridium tetani*)
(57) gch2_chlte: TrEMBL: Q8KC35 (*Chlorobium tepidum*)
(58) gch2_aquae: SWISS-PROT: gch2_aquae (*Aquifex aeolicus*)
(59) gch2_lepin: TrEMBL: Q8F701 (*Leptospira interrogans*)
(60) gch2_deira: TrEMBL: Q9RXZ9 (*Deinococcus radiodurans*)
(61) gch2_bacth: TrEMBL: Q8A528 (*Bacteroides thetaiotaomicron*)
(62) gch2_caucr: TrEMBL: Q9A9S5 (*Caulobacter crescentus*)
(63) gch2_coxbu: TrEMBL: AAO90191 (*Coxiella burnetii* RSA 493)
(64) gch2_rhiet: TrEMBL: Q8KL38 (*Rhizobium etli*)
(65) gch2_lacpl: TrEMBL: Q88X17 (*Lactobacillus plantarum*)
(66) gch2_psegl: TrEMBL: Q8RS38 (*Pseudomonas glumae*)
(67) gch2_strav: TrEMBL: BAC71833 (*Streptomyces avermitilis*)
(68) gch2_phopo: SWISS-PROT: gch2_phopo (*Photobacterium phosphoreum*)
(69) gch2_azobr: SWISS-PROT: gch2_azobr (*Azospirillum brasilense*)
(70) gch2_agrtu: TrEMBL: Q8UHC9 (*Agrobacterium tumefaciens* (strain C58/ATCC 33970))
(71) gch2_rhime: TrEMBL: Q92RH2 (*Rhizobium meliloti* (*Sinorhizobium meliloti*))
(72) gch2_brume: TrEMBL: Q8YFL5 (*Brucella melitensis*)
(73) gch2_brusu: TrEMBL: Q8G298 (*Brucella suis*)
(74) gch2_rhilo: TrEMBL: Q985Z3 (*Rhizobium loti* (*Mesorhizobium loti*))
(75) gch2_braja: TrEMBL: Q89RZ7 (*Bradyrhizobium japonicum*)
(76) gch2_niteu: TrEMBL: CAD86468 (*Nitrosomonas europaea* ATCC 19718)
(77) gch2_ralso: TrEMBL: Q8Y1H7 (*Ralstonia solanacearum* (*Pseudomonas solanacearum*))
(78) gch2_neime: TrEMBL: Q9JZ77 (*Neisseria meningitidis* (serogroup B, second enzyme found))
(79) gch2_xanax: TrEMBL: Q8PPD7 (*Xanthomonas axonopodis* (pv. citri))
(80) gch2_xanca: TrEMBL: Q8PCM8 (*Xanthomonas campestris* (pv. campestris))
(81) gch2_vibpa: TrEMBL: Q87RU5 (*Vibrio parahaemolyticus*)
(82) gch2_vibvu: TrEMBL: Q8DF98 (*Vibrio vulnificus*)
(83) gch2_vibch: TrEMBL: Q9KPU3 (*Vibrio cholerae*)
(84) gch2_vibfi: TrEMBL: Q8G9G5 (*Vibrio fischeri*)
(85) gch2_sheon: TrEMBL: Q8EBP2 (*Shewanella oneidensis*)
(86) gch2_phoph: TrEMBL: Q8G9H7 (*Photobacterium phosphoreum*)
(87) ribb_phole: TrEMBL: Q93E93 (*Photobacterium leiognathi*)
(88) gch2_psepu: TrEMBL: Q88GB1 (*Pseudomonas putida* (strain KT2440, second enzyme found))
(89) gch2_psesy: TrEMBL: Q882G0 (*Pseudomonas syringae* (pv. Tomato, second enzyme found))
(90) gch2_pseae: TrEMBL: Q9HWX4 (*Pseudomonas aeruginosa*)
(91) ribb_dehmu: SWISS-PROT: ribb_dehmu (*Dehalospirillum multivorans*)
(92) gch2_xylfa: TrEMBL: Q87D69 (*Xylella fastidiosa* (strain Temecula1/ATCC 700964))

TABLE 4

Positions/amino acid residues corresponding to positions V261, G270, A276, Q279, K308, and M347 of RibA of *B. subtilis* as of SEQ ID NO: 2. The numbers in the left column refer to the different organisms (see above).

|  |  |  |  |  |  |  | SEQ ID NO DNA; protein |
|---|---|---|---|---|---|---|---|
| (1) | V261 | G270 | A276 | Q279 | K308 | M347 | 1; 2 |
| (2) | T181 | G190 | A196 | L199 | N228 | I267 | |
| (3) | T126 | G135 | A141 | L144 | N182 | I221 | 32; 33 |
| (4) | N153 | G162 | A168 | L171 | N211 | V250 | |
| (5) | T255 | G264 | A270 | L273 | N305 | I344 | |
| (6) | T176 | G185 | A191 | L194 | N223 | I262 | |
| (7) | V139 | G248 | A254 | M257 | K287 | I326 | |
| (8) | A73 | G82 | A88 | Q91 | A121 | V160 | |
| (9) | A60 | G69 | A75 | R78 | A106 | M145 | |
| (10) | A60 | G69 | A75 | R78 | A106 | M145 | |
| (11) | T151 | G160 | A166 | T169 | E297 | I336 | |
| (12) | V245 | G254 | F260 | Y263 | S291 | V330 | |
| (13) | V267 | G276 | A282 | Y285 | A315 | V354 | |
| (14) | I267 | G276 | A282 | Y285 | A315 | V354 | |
| (15) | I272 | G281 | A287 | Y290 | A320 | I359 | |
| (16) | I272 | G281 | A287 | Y290 | A320 | I359 | |
| (17) | I91 | G100 | S106 | Q109 | N139 | M178 | |
| (18) | I299 | G308 | A314 | Q317 | N347 | M386 | |
| (19) | I295 | G304 | A310 | L313 | N343 | M382 | |
| (20) | V61 | G70 | A76 | K79 | R109 | V148 | |
| (21) | A60 | G69 | A75 | A78 | H107 | V146 | |
| (22) | A60 | G69 | A75 | A78 | H107 | V146 | |
| (23) | A59 | G68 | A74 | A77 | E106 | L145 | |
| (24) | A59 | G68 | A74 | A77 | E106 | L145 | |
| (25) | A61 | G70 | A76 | A79 | S108 | I147 | |
| (26) | A61 | G70 | A76 | A79 | S108 | V147 | |
| (27) | A61 | G70 | A76 | A79 | S108 | V147 | |
| (28) | A80 | G89 | A95 | Q98 | A127 | V166 | |
| (29) | A59 | G68 | A74 | Q77 | A106 | V145 | 34; 35 |
| (30) | A59 | G68 | A74 | H77 | A106 | V145 | |
| (31) | A59 | G68 | A74 | R77 | A106 | V145 | |
| (32) | A57 | G66 | S72 | R75 | A104 | I143 | |
| (33) | A59 | G68 | A74 | R77 | S106 | I145 | |
| (34) | A59 | G68 | A74 | H77 | S106 | I145 | |
| (35) | A60 | G69 | A75 | E78 | A107 | I146 | |
| (36) | V279 | G288 | A294 | M297 | Q327 | M366 | |
| (37) | V269 | G278 | A284 | M287 | Q317 | M356 | |
| (38) | V281 | G290 | S296 | M299 | Q329 | I368 | |
| (39) | V273 | G282 | S288 | L291 | Q321 | L360 | 36; 37 |
| (40) | V274 | G283 | S289 | I292 | S322 | A361 | |
| (41) | I259 | G268 | S274 | Y277 | E305 | I344 | |
| (42) | I263 | G272 | S276 | Y279 | E309 | I348 | |
| (43) | A264 | G273 | A279 | Q282 | E311 | I350 | |
| (44) | A262 | G271 | A277 | K280 | S309 | L348 | |

TABLE 4-continued

Positions/amino acid residues corresponding to positions V261, G270, A276, Q279, K308, and M347 of RibA of B. subtilis as of SEQ ID NO: 2. The numbers in the left column refer to the different organisms (see above).

| | | | | | | | SEQ ID NO DNA; protein |
|---|---|---|---|---|---|---|---|
| (45) | V261 | G270 | A276 | Q279 | H308 | I347 | |
| (46) | V261 | G270 | A276 | M279 | H308 | L347 | |
| (47) | V264 | G273 | A279 | A282 | M311 | V350 | |
| (48) | I261 | G270 | A276 | R279 | N308 | I347 | |
| (49) | A301 | R310 | A316 | M319 | S348 | I387 | |
| (50) | A265 | R274 | A280 | M283 | S312 | I351 | |
| (51) | A267 | R276 | A282 | M285 | S315 | I353 | |
| (52) | V261 | G270 | A276 | Q279 | R308 | M347 | 38; 39 |
| (53) | V260 | G269 | A275 | Q278 | K307 | L346 | 40; 41 |
| (54) | V264 | G273 | A279 | Q282 | K311 | M350 | 42; 43 |
| (55) | V244 | G253 | A259 | K262 | K291 | I330 | |
| (56) | A265 | G274 | A280 | A283 | N312 | I351 | |
| (57) | T267 | G276 | A282 | M285 | N314 | M353 | |
| (58) | V270 | R279 | A285 | M288 | E317 | M356 | |
| (59) | I263 | G272 | A278 | M281 | N310 | M349 | |
| (60) | A269 | G278 | A284 | A287 | A316 | L355 | |
| (61) | I265 | G274 | A281 | M283 | K314 | M351 | |
| (62) | A260 | G269 | S276 | Q278 | A307 | V346 | |
| (63) | V265 | G274 | A280 | E283 | A311 | I350 | |
| (64) | A283 | G292 | A298 | A301 | S330 | V369 | |
| (65) | V262 | G271 | A277 | K280 | A309 | V348 | |
| (66) | V70 | G79 | S85 | L88 | R117 | V156 | |
| (67) | V66 | G75 | A81 | R84 | A112 | L151 | |
| (68) | G61 | G70 | T76 | I79 | K108 | I147 | |
| (69) | L250 | G259 | A265 | E268 | R297 | V336 | |
| (70) | V264 | — | Y274 | K277 | K304 | I340 | |
| (71) | V264 | — | I274 | R277 | K304 | I340 | |
| (72) | V264 | — | I275 | R278 | R305 | I345 | |
| (73) | V264 | — | I275 | R278 | R305 | I345 | |
| (74) | V264 | — | I274 | A277 | — | I340 | |
| (75) | I261 | — | V271 | H274 | — | I330 | |
| (76) | L262 | S271 | A277 | V280 | D303 | M338 | |
| (77) | L285 | S294 | A300 | A303 | Q327 | M362 | |
| (78) | F263 | S271 | A277 | H280 | D303 | L336 | |
| (79) | L262 | G271 | A277 | A280 | R304 | L339 | |
| (80) | L262 | G271 | A277 | A280 | R304 | L339 | |
| (81) | V261 | S271 | A277 | R280 | R303 | M343 | |
| (82) | L261 | S271 | A277 | R280 | R303 | M343 | |
| (83) | L261 | S271 | A277 | R280 | R303 | M343 | |
| (84) | I261 | S271 | A277 | R280 | R303 | M343 | |
| (85) | L260 | S270 | A276 | R279 | K302 | M343 | |
| (86) | I262 | — | A275 | R278 | K301 | M341 | |
| (87) | I262 | — | A275 | R278 | Q301 | I339 | |
| (88) | L262 | N272 | A278 | K281 | R305 | L342 | |
| (89) | L262 | N272 | A278 | R281 | R305 | L342 | |
| (90) | L262 | R270 | A276 | K279 | H303 | M339 | |
| (91) | L269 | Y276 | A282 | Y285 | — | I324 | |
| (92) | L230 | G239 | S245 | T248 | G277 | I316 | |

The examples shown in Table 4 serve as illustration of the principle. Corresponding residues can be determined for all other GTP cyclohydrolase II amino acid sequences that are homologous to any one of the sequences shown in Table 4.

The invention claimed is:

1. A method for producing riboflavin, a riboflavin precursor, FMN, FAD, or a derivative thereof comprising:
culturing a host cell in a suitable medium, the host cell comprising a polynucleotide comprising a nucleotide sequence which codes for a modified GTP cyclohydrolase II from *Bacillus subtilis*, wherein (i) the specific activity of the modified enzyme is increased in comparison to the corresponding non-modified enzyme and (ii) the amino acid sequence of the modified enzyme comprises one or more mutations(s) on amino acid position(s) corresponding to positions 261, 270, 276, 279, 308, and/or 347 of SEQ ID NO: 2 and combinations of the one or more mutations(s) thereof such that said modified enzyme includes from 1 to 6 position substitutions selected from: Alanine at an amino acid position corresponding to the position 261, Alanine or Arginine at an amino acid position corresponding to the position 270, Threonine at an amino acid position corresponding to the position 276, Arginine at an amino acid position corresponding to the position 279, Arginine at an amino acid position corresponding to the position 308, and Isoleucine at an amino acid position corresponding to the position 347; said modified enzyme exhibiting at least 98% identity to SEQ ID NO: 2, and
optionally separating riboflavin, a riboflavin precursor, FMN, FAD, or a derivative thereof from the medium.

2. A method for increasing the production of riboflavin, a riboflavin precursor, FMN, FAD, or a derivative thereof by introducing into a host cell a modified GTP cyclohydrolase II from *Bacillus subtilis*, wherein (i) the specific activity of the modified enzyme is increased in comparison to the corresponding non-modified enzyme, and (ii) the amino acid sequence of the modified enzyme comprises one or more mutations(s) on amino acid position(s) corresponding to positions 261, 270, 276, 279, 308, and/or 347 of SEQ ID NO: 2 and combinations of the one or more mutation(s) thereof such that said modified enzyme includes from 1 to 6 position substitutions selected from: Alanine at an amino acid position corresponding to the position 261, Alanine or Arginine at an amino acid position corresponding to the position 270, Threonine at an amino acid position corresponding to the position 276, Arginine at an amino acid position corresponding to the position 279, Arginine at an amino acid position corresponding to the position 308, and a sixth mutation comprises an Isoleucine at an amino acid position corresponding to the position 347, said modified enzyme exhibiting at least 98% identity to SEQ ID NO: 2.

3. A method for increasing the production of riboflavin, a riboflavin precursor, FMN, FAD, or a derivative thereof by introducing into a host cell a polynucleotide comprising a nucleotide sequence which codes for a modified GTP cyclohydrolase II from *Bacillus subtilis*, wherein (i) the specific activity of the modified enzyme is increased in comparison to the corresponding non-modified enzyme, and
(ii the amino acid sequence of the modified enzyme comprises one or more mutations(s) on amino acid position(s) corresponding to positions 261, 270, 276, 279, 308, and/or 347 of SEQ ID NO: 2 and combinations of the one or more mutation(s) thereof such that said modified enzyme includes from 1 to 6 position substitutions selected from: Alanine at an amino acid position corresponding to the position 261, Alanine or Arginine at an amino acid position corresponding to the position 270, Threonine at an amino acid position corresponding to the position 276, Arginine at an amino acid position corresponding to the position 279, Arginine at an amino acid position corresponding to the position 308, and a sixth mutation comprises an Isoleucine at an amino acid position corresponding to the position 347, said modified enzyme exhibiting at least 98% identity to SEQ ID NO: 2.

4. A method for producing riboflavin, a riboflavin precursor, FMN, FAD, or a derivative thereof comprising:
culturing a host cell in a suitable medium, the host cell comprising a polynucleotide comprising a nucleotide sequence which codes for a modified GTP cyclohydrolase II from *Bacillus subtilis*, wherein (i) the specific activity of the modified enzyme is increased in comparison to the corresponding non-modified enzyme and (ii) the amino acid sequence of the modified enzyme consisting of one or more mutations(s) on amino acid position(s) corresponding to positions 261, 270, 276, 279, 308, and/or 347 of SEQ ID NO: 2 and combinations of the one or more mutations(s) thereof such that said modified enzyme includes from 1 to 6 position substitutions selected from: Alanine at an amino acid position corresponding to the position 261; Alanine or Arginine at an amino acid position corresponding to the position 270; Threonine at an amino acid position corresponding to the position 276; Arginine at an amino acid position corresponding to the position 279; Arginine at an amino acid position corresponding to the position 308, and Isoleucine at an amino acid position corresponding to the position 347; said modified enzyme exhibiting at least 98% identity to SEQ ID NO: 2, and
optionally separating riboflavin, a riboflavin precursor, FMN, FAD, or a derivative thereof from the medium.

* * * * *